(12) United States Patent
Muller et al.

(10) Patent No.: US 8,906,864 B2
(45) Date of Patent: Dec. 9, 2014

(54) BINDING DOMAINS OF PROTEINS OF THE REPULSIVE GUIDANCE MOLECULE (RGM) PROTEIN FAMILY AND FUNCTIONAL FRAGMENTS THEREOF, AND THEIR USE

(75) Inventors: Bernhard K. Muller, Neustadt (DE); Gregor Schaffar, Mannheim (DE); Reinhold Mueller, Schifferstadt (DE)

(73) Assignee: AbbVie Deutschland GmbH & Co. KG, Wiesbaden (DE)

( * ) Notice: Subject to any disclaimer, the term of this patent is extended or adjusted under 35 U.S.C. 154(b) by 652 days.

(21) Appl. No.: 11/992,720

(22) PCT Filed: Sep. 29, 2006

(86) PCT No.: PCT/EP2006/009497
§ 371 (c)(1),
(2), (4) Date: May 16, 2009

(87) PCT Pub. No.: WO2007/039256
PCT Pub. Date: Apr. 12, 2007

(65) Prior Publication Data
US 2009/0297527 A1 Dec. 3, 2009

Related U.S. Application Data

(60) Provisional application No. 60/722,565, filed on Oct. 1, 2005.

(30) Foreign Application Priority Data

Sep. 30, 2005 (EP) ..................... 05021451

(51) Int. Cl.
*A61K 38/18* (2006.01)
*A61K 38/17* (2006.01)
*C07K 14/475* (2006.01)
*C07K 14/435* (2006.01)
*C07K 16/28* (2006.01)
*C07K 14/705* (2006.01)
*A61K 38/00* (2006.01)

(52) U.S. Cl.
CPC .............. *C07K 14/705* (2013.01); *C07K 16/28* (2013.01); *C07K 2317/34* (2013.01); *A61K 38/00* (2013.01)
USPC .......... 514/21.3; 514/21.2; 530/300; 530/350

(58) Field of Classification Search
None
See application file for complete search history.

(56) References Cited

U.S. PATENT DOCUMENTS

| | | |
|---|---|---|
| 4,394,448 A | 7/1983 | Szoka, Jr. et al. |
| 4,399,216 A | 8/1983 | Axel et al. |
| 4,510,245 A | 4/1985 | Cousens et al. |
| 4,526,938 A | 7/1985 | Churchill et al. |
| 4,554,101 A | 11/1985 | Hopp |
| 4,634,665 A | 1/1987 | Axel et al. |
| 4,704,692 A | 11/1987 | Ladner |
| 4,816,397 A | 3/1989 | Boss et al. |
| 4,816,567 A | 3/1989 | Cabilly et al. |
| 4,873,316 A | 10/1989 | Meade et al. |
| 4,880,078 A | 11/1989 | Inoue et al. |
| 4,946,778 A | 8/1990 | Ladner et al. |
| 4,968,615 A | 11/1990 | Koszinowski et al. |
| 4,980,286 A | 12/1990 | Morgan et al. |
| 5,006,309 A | 4/1991 | Khalil et al. |
| 5,063,081 A | 11/1991 | Cozzette et al. |
| 5,089,424 A | 2/1992 | Khalil et al. |
| 5,128,326 A | 7/1992 | Balazs et al. |
| 5,135,875 A | 8/1992 | Meucci et al. |
| 5,168,062 A | 12/1992 | Stinski |
| 5,179,017 A | 1/1993 | Axel et al. |
| 5,223,409 A | 6/1993 | Ladner et al. |
| 5,225,539 A | 7/1993 | Winter |
| 5,241,070 A | 8/1993 | Law |
| 5,258,498 A | 11/1993 | Huston et al. |
| 5,290,540 A | 3/1994 | Prince et al. |
| 5,294,404 A | 3/1994 | Grandone et al. |

(Continued)

FOREIGN PATENT DOCUMENTS

| | | |
|---|---|---|
| DE | 102008014880 A1 | 9/2009 |
| EA | 008253 B1 | 4/2007 |
| EP | 321201 A2 | 6/1989 |
| EP | 360257 A2 | 3/1990 |
| EP | 0368684 A1 | 5/1990 |
| EP | 404097 A2 | 12/1990 |
| EP | 0471293 A2 | 2/1992 |
| EP | 0519596 A1 | 12/1992 |
| EP | 229246 B1 | 8/1993 |
| EP | 592106 A1 | 4/1994 |

(Continued)

OTHER PUBLICATIONS

Wells, J.A. (1990). Additivity of mutational effects in proteins. Biochemistry. 29(37):8509-8517.*

(Continued)

*Primary Examiner* — Christine J Saoud
*Assistant Examiner* — Jon M Lockard
(74) *Attorney, Agent, or Firm* — Lisa V. Mueller; Michael Best & Friedrich LLP

(57) ABSTRACT

The invention concerns the identification and use of neogenin receptor-binding domains of members of the repulsive guidance molecule (RGM) protein family as well as polypeptide fragments derived therefrom. The inventive domains, i.e. peptide fragments are suited as agents for the active or passive immunization of individuals as well as diagnostic and therapeutic agents for use with diseases or pathological conditions in whose origin or progression, a member of the RGM family and a cellular receptor assigned to this molecule are involved. The invention also concerns monoclonal and polyclonal antibodies directed against the inventive binding domains and against the polypeptides derived therefrom, and to method for producing the inventive domains, polypeptides and antibodies.

6 Claims, 9 Drawing Sheets

(56) References Cited

U.S. PATENT DOCUMENTS

| | | |
|---|---|---|
| 5,304,489 A | 4/1994 | Rosen |
| 5,352,803 A | 10/1994 | Mattingly |
| 5,359,093 A | 10/1994 | Adamczyk et al. |
| 5,403,484 A | 4/1995 | Ladner et al. |
| 5,427,908 A | 6/1995 | Dower et al. |
| 5,468,646 A | 11/1995 | Mattingly et al. |
| 5,480,792 A | 1/1996 | Buechler et al. |
| 5,496,925 A | 3/1996 | Mattingly |
| 5,516,637 A | 5/1996 | Huang et al. |
| 5,525,490 A | 6/1996 | Erickson et al. |
| 5,525,524 A | 6/1996 | Buechler et al. |
| 5,530,101 A | 6/1996 | Queen et al. |
| 5,541,109 A | 7/1996 | Searfoss, III et al. |
| 5,543,524 A | 8/1996 | Mattingly et al. |
| 5,545,806 A | 8/1996 | Lonberg et al. |
| 5,565,332 A | 10/1996 | Hoogenboom et al. |
| 5,565,352 A | 10/1996 | Hochstrasser et al. |
| 5,565,362 A | 10/1996 | Rosen |
| 5,569,825 A | 10/1996 | Lonberg et al. |
| 5,571,698 A | 11/1996 | Ladner et al. |
| 5,573,904 A | 11/1996 | Mattingly |
| 5,580,717 A | 12/1996 | Dower et al. |
| 5,580,859 A | 12/1996 | Felgner et al. |
| 5,585,089 A | 12/1996 | Queen et al. |
| 5,593,896 A | 1/1997 | Adamczyk et al. |
| 5,624,821 A | 4/1997 | Winter et al. |
| 5,625,126 A | 4/1997 | Lonberg et al. |
| 5,627,052 A | 5/1997 | Schrader |
| 5,633,425 A | 5/1997 | Lonberg et al. |
| 5,648,260 A | 7/1997 | Winter et al. |
| 5,658,727 A | 8/1997 | Barbas et al. |
| 5,661,016 A | 8/1997 | Lonberg et al. |
| 5,679,377 A | 10/1997 | Bernstein et al. |
| 5,679,526 A | 10/1997 | Buechler et al. |
| 5,693,762 A | 12/1997 | Queen et al. |
| 5,698,426 A | 12/1997 | Huse |
| 5,714,350 A | 2/1998 | Co et al. |
| 5,714,352 A | 2/1998 | Jakobovits |
| 5,723,323 A | 3/1998 | Kauffman et al. |
| 5,733,743 A | 3/1998 | Johnson et al. |
| 5,747,262 A | 5/1998 | Hinck et al. |
| 5,750,753 A | 5/1998 | Kimae et al. |
| 5,763,192 A | 6/1998 | Kauffman et al. |
| 5,766,886 A | 6/1998 | Studnicka et al. |
| 5,770,429 A | 6/1998 | Lonberg et al. |
| 5,780,225 A | 7/1998 | Wigler et al. |
| 5,783,699 A | 7/1998 | Mattingly et al. |
| 5,807,715 A | 9/1998 | Morrison et al. |
| 5,814,318 A | 9/1998 | Lonberg et al. |
| 5,814,476 A | 9/1998 | Kauffman et al. |
| 5,817,483 A | 10/1998 | Kauffman et al. |
| 5,821,047 A | 10/1998 | Garrard et al. |
| 5,824,514 A | 10/1998 | Kauffman et al. |
| 5,824,799 A | 10/1998 | Buechler et al. |
| 5,827,690 A | 10/1998 | Meade et al. |
| 5,833,985 A | 11/1998 | Ball et al. |
| 5,837,243 A | 11/1998 | Deo et al. |
| 5,837,500 A | 11/1998 | Ladner et al. |
| 5,849,992 A | 12/1998 | Meade et al. |
| 5,851,776 A | 12/1998 | Valkirs |
| 5,855,913 A | 1/1999 | Hanes et al. |
| 5,874,064 A | 2/1999 | Edwards et al. |
| 5,877,397 A | 3/1999 | Lonberg et al. |
| 5,885,527 A | 3/1999 | Buechler |
| 5,885,793 A | 3/1999 | Griffiths et al. |
| 5,912,015 A | 6/1999 | Bernstein et al. |
| 5,916,597 A | 6/1999 | Lee et al. |
| 5,916,771 A | 6/1999 | Hori et al. |
| 5,922,615 A | 7/1999 | Nowakowski et al. |
| 5,922,845 A | 7/1999 | Deo et al. |
| 5,934,272 A | 8/1999 | Lloyd et al. |
| 5,939,272 A | 8/1999 | Buechler et al. |
| 5,939,598 A | 8/1999 | Kucherlapati et al. |
| 5,947,124 A | 9/1999 | Buechler et al. |
| 5,969,108 A | 10/1999 | McCafferty et al. |
| 5,976,862 A | 11/1999 | Kauffman et al. |
| 5,985,309 A | 11/1999 | Edwards et al. |
| 5,985,320 A | 11/1999 | Edwards et al. |
| 5,985,579 A | 11/1999 | Buechler et al. |
| 5,985,615 A | 11/1999 | Jakobovits et al. |
| 5,989,463 A | 11/1999 | Tracy et al. |
| 5,994,616 A | 11/1999 | Rosen |
| 5,994,619 A | 11/1999 | Stice et al. |
| 5,998,209 A | 12/1999 | Jokobovits et al. |
| 6,004,746 A | 12/1999 | Brent et al. |
| 6,017,517 A | 1/2000 | Park |
| 6,019,944 A | 2/2000 | Buechler |
| 6,019,968 A | 2/2000 | Platz et al. |
| 6,075,181 A | 6/2000 | Kucherlapati et al. |
| 6,087,326 A | 7/2000 | Hinck et al. |
| 6,091,001 A | 7/2000 | Jakobovits et al. |
| 6,096,311 A | 8/2000 | Fanger et al. |
| 6,111,166 A | 8/2000 | Van De Winkel |
| 6,113,855 A | 9/2000 | Buechler |
| 6,114,598 A | 9/2000 | Kucherlapati et al. |
| 6,130,364 A | 10/2000 | Jakobovits et al. |
| 6,143,576 A | 11/2000 | Buechler |
| 6,180,370 B1 | 1/2001 | Queen et al. |
| 6,204,023 B1 | 3/2001 | Robinson et al. |
| 6,270,765 B1 | 8/2001 | Deo et al. |
| 6,303,755 B1 | 10/2001 | Deo et al. |
| 6,350,861 B1 | 2/2002 | Co et al. |
| 6,365,116 B1 | 4/2002 | Barham et al. |
| 6,410,690 B1 | 6/2002 | Deo et al. |
| 6,632,926 B1 | 10/2003 | Chen et al. |
| 6,660,843 B1 | 12/2003 | Feige et al. |
| 6,682,928 B2 | 1/2004 | Keler et al. |
| 6,699,658 B1 | 3/2004 | Wittrup et al. |
| 6,864,239 B2 | 3/2005 | Peri et al. |
| 6,890,763 B2 | 5/2005 | Jackowski et al. |
| 6,914,128 B1 | 7/2005 | Salfeld et al. |
| 6,925,389 B2 | 8/2005 | Hitt et al. |
| 6,984,720 B1 | 1/2006 | Korman et al. |
| 6,989,100 B2 | 1/2006 | Norton |
| 7,094,761 B2 | 8/2006 | Peri et al. |
| 7,265,212 B2 | 9/2007 | Babcook et al. |
| 7,288,253 B2 | 10/2007 | Roskos et al. |
| 7,368,531 B2 | 5/2008 | Rosen et al. |
| 7,439,063 B2 | 10/2008 | Digicaylioglu et al. |
| 7,498,034 B2 | 3/2009 | Bicknell et al. |
| 7,504,225 B2 | 3/2009 | Ring et al. |
| 7,524,492 B2 | 4/2009 | Sharma |
| 7,582,440 B2 | 9/2009 | Bicknell et al. |
| 7,612,181 B2 | 11/2009 | Wu et al. |
| 7,612,183 B2 | 11/2009 | Ellis et al. |
| 7,659,370 B2 | 2/2010 | Woolf et al. |
| 7,696,155 B2 * | 4/2010 | Woolf et al. ............... 514/17.7 |
| 7,696,156 B2 | 4/2010 | Woolf et al. |
| 7,771,952 B2 | 8/2010 | Strittmatter et al. |
| 7,951,369 B2 | 5/2011 | Goldenberg et al. |
| 7,968,091 B2 | 6/2011 | Woolf et al. |
| 7,968,520 B2 | 6/2011 | Woolf et al. |
| 7,981,415 B2 | 7/2011 | Staunton et al. |
| 7,981,416 B2 | 7/2011 | Hardy et al. |
| 7,981,420 B2 | 7/2011 | Mueller et al. |
| 7,999,072 B2 | 8/2011 | Plouet et al. |
| 8,017,115 B2 | 9/2011 | Irving et al. |
| 2002/0110804 A1 | 8/2002 | Stanton et al. |
| 2002/0136725 A1 | 9/2002 | Blackburn et al. |
| 2002/0137134 A1 | 9/2002 | Gerngross |
| 2003/0009152 A1 | 1/2003 | O'hara et al. |
| 2003/0087394 A1 | 5/2003 | Sharma |
| 2003/0170881 A1 | 9/2003 | Davis et al. |
| 2003/0186374 A1 | 10/2003 | Hufton et al. |
| 2003/0212001 A1 | 11/2003 | Peri et al. |
| 2003/0235584 A1 | 12/2003 | Kloetzer et al. |
| 2004/0009491 A1 | 1/2004 | Birse et al. |
| 2004/0018577 A1 | 1/2004 | Emerson et al. |
| 2004/0018590 A1 | 1/2004 | Gerngross et al. |
| 2004/0038292 A1 | 2/2004 | Burslem et al. |
| 2004/0071711 A1 | 4/2004 | Bicknell et al. |
| 2004/0092444 A1 | 5/2004 | Digicaylioglu et al. |
| 2004/0102376 A1 | 5/2004 | Mueller et al. |
| 2005/0013809 A1 | 1/2005 | Owens et al. |

(56) References Cited

U.S. PATENT DOCUMENTS

| | | |
|---|---|---|
| 2005/0042664 A1 | 2/2005 | Wu et al. |
| 2005/0054078 A1 | 3/2005 | Miller et al. |
| 2005/0058649 A1 | 3/2005 | Landes et al. |
| 2005/0059604 A1 | 3/2005 | Peri et al. |
| 2005/0142137 A1 | 6/2005 | Gallo et al. |
| 2005/0197284 A9 | 9/2005 | Digicaylioglu et al. |
| 2006/0003391 A1 | 1/2006 | Ring et al. |
| 2006/0063208 A1 | 3/2006 | Woolf et al. |
| 2006/0104968 A1 | 5/2006 | Bookbinder et al. |
| 2006/0160164 A1 | 7/2006 | Miller et al. |
| 2006/0252101 A1 | 11/2006 | Strittmatter et al. |
| 2006/0292613 A1 | 12/2006 | Peri et al. |
| 2007/0025913 A1 | 2/2007 | Bicknell et al. |
| 2007/0071675 A1 | 3/2007 | Wu et al. |
| 2007/0122491 A1 | 5/2007 | Lyons et al. |
| 2007/0155687 A1 | 7/2007 | Lyons et al. |
| 2007/0166711 A1 | 7/2007 | Samuels et al. |
| 2007/0253946 A1 | 11/2007 | Yamashita et al. |
| 2008/0004255 A1 | 1/2008 | Lyons et al. |
| 2008/0008692 A1 | 1/2008 | Lyons et al. |
| 2008/0020401 A1 | 1/2008 | Grenier et al. |
| 2008/0081337 A1 | 4/2008 | Sharma |
| 2008/0105705 A1 | 5/2008 | Schmidt |
| 2008/0135582 A1 | 6/2008 | Schmidt |
| 2008/0145359 A1 | 6/2008 | Bicknell et al. |
| 2008/0160034 A1 | 7/2008 | Brennan et al. |
| 2008/0181897 A1 | 7/2008 | Ni et al. |
| 2008/0213791 A1 | 9/2008 | Freije et al. |
| 2008/0219924 A1 | 9/2008 | Bicknell et al. |
| 2008/0248493 A1 | 10/2008 | Mattingly et al. |
| 2008/0274045 A9 | 11/2008 | Bicknell et al. |
| 2008/0279859 A1 | 11/2008 | Mezler et al. |
| 2009/0012628 A1 | 1/2009 | Shortkroff et al. |
| 2009/0017039 A1 | 1/2009 | Mi et al. |
| 2009/0028852 A1 | 1/2009 | Herrera et al. |
| 2009/0054984 A1 | 2/2009 | Shortkroff et al. |
| 2009/0069903 A1 | 3/2009 | Shortkroff et al. |
| 2009/0093409 A1 | 4/2009 | Digicaylioglu et al. |
| 2009/0123413 A1 | 5/2009 | Hardy et al. |
| 2009/0191118 A1 | 7/2009 | Young et al. |
| 2009/0191572 A1 | 7/2009 | Bicknell et al. |
| 2009/0220588 A1 | 9/2009 | Edelman et al. |
| 2009/0220589 A1 | 9/2009 | Trieu et al. |
| 2009/0227502 A1 | 9/2009 | Goldberg et al. |
| 2009/0252742 A1 | 10/2009 | Bergstein |
| 2009/0252748 A1 | 10/2009 | Mi et al. |
| 2009/0269356 A1 | 10/2009 | Epstein et al. |
| 2009/0280116 A1 | 11/2009 | Smith et al. |
| 2009/0304693 A1 | 12/2009 | Ghayur et al. |
| 2009/0311253 A1 | 12/2009 | Ghayur et al. |
| 2010/0004431 A1 | 1/2010 | Bernett et al. |
| 2010/0015665 A1 | 1/2010 | Latham et al. |
| 2010/0028340 A1 | 2/2010 | Mueller et al. |
| 2010/0036091 A1 | 2/2010 | Robinson et al. |
| 2010/0036502 A1 | 2/2010 | Svrluga et al. |
| 2010/0041139 A1 | 2/2010 | Goldberg |
| 2010/0047239 A1 | 2/2010 | Wu et al. |
| 2010/0068803 A1 | 3/2010 | Goldberg |
| 2010/0099103 A1 | 4/2010 | Hsieh et al. |
| 2010/0105569 A1 | 4/2010 | Hsieh et al. |
| 2010/0111967 A1 | 5/2010 | Baehner et al. |
| 2010/0150918 A1 | 6/2010 | Kufer et al. |
| 2010/0168393 A1 | 7/2010 | Clube et al. |
| 2010/0183588 A1 | 7/2010 | Plouet et al. |
| 2010/0183608 A1 | 7/2010 | Woolf et al. |
| 2010/0183631 A1 | 7/2010 | Rothe et al. |
| 2010/0184033 A1 | 7/2010 | West et al. |
| 2010/0249039 A1 | 9/2010 | Zangemeister-Wittke et al. |
| 2010/0254979 A1 | 10/2010 | Staunton et al. |
| 2010/0286048 A1 | 11/2010 | Rosen et al. |
| 2010/0297121 A1 | 11/2010 | Mi |
| 2010/0310573 A1 | 12/2010 | Nakagawa et al. |
| 2010/0322948 A1 | 12/2010 | Mueller et al. |
| 2011/0003971 A1 | 1/2011 | Strittmatter et al. |
| 2011/0020221 A1 | 1/2011 | Berman et al. |
| 2011/0070156 A1 | 3/2011 | Govindan et al. |
| 2011/0110852 A1 | 5/2011 | Miller et al. |
| 2011/0110936 A1 | 5/2011 | Nam et al. |
| 2011/0112280 A1 | 5/2011 | Mueller et al. |
| 2011/0117085 A1 | 5/2011 | Rotem-Yehudar et al. |
| 2011/0135657 A1 | 6/2011 | Hu et al. |
| 2011/0135664 A1 | 6/2011 | Mueller |
| 2011/0171126 A1 | 7/2011 | Burton et al. |
| 2011/0183924 A1 | 7/2011 | Mintz et al. |
| 2011/0195021 A1 | 8/2011 | Deckert et al. |
| 2011/0206671 A1 | 8/2011 | Yamashita et al. |
| 2011/0212107 A1 | 9/2011 | Goldberg et al. |
| 2011/0243841 A1 | 10/2011 | Chang et al. |
| 2011/0263827 A1 | 10/2011 | Ghayur et al. |
| 2011/0293526 A1 | 12/2011 | Plikus et al. |

FOREIGN PATENT DOCUMENTS

| | | |
|---|---|---|
| EP | 239400 B1 | 8/1994 |
| EP | 291533 B1 | 10/1995 |
| EP | 0963376 A1 | 12/1999 |
| EP | 1176195 A1 | 1/2002 |
| EP | 1347046 | 9/2003 |
| EP | 1396543 A2 | 3/2004 |
| EP | 1440981 A2 | 7/2004 |
| EP | 1677113 A1 | 7/2006 |
| EP | 1733737 A1 | 12/2006 |
| EP | 2033971 A1 | 3/2009 |
| EP | 2260055 A1 | 12/2010 |
| GB | 8901334 | 5/1990 |
| GB | 9101134 | 1/1992 |
| GB | 9201755 | 4/1993 |
| GB | 2456390 A | 7/2009 |
| JP | 2010065045 A | 3/2010 |
| JP | 2011512806 A | 4/2011 |
| JP | 4986370 B2 | 7/2012 |
| KR | 20080058021 A | 6/2008 |
| RU | 2212241 C2 | 9/2003 |
| RU | 2362780 C2 | 7/2009 |
| WO | 9002809 A1 | 3/1990 |
| WO | 9005144 A1 | 5/1990 |
| WO | 9005370 A1 | 5/1990 |
| WO | 9014424 A1 | 11/1990 |
| WO | 9014430 A1 | 11/1990 |
| WO | 9014443 A1 | 11/1990 |
| WO | 9105548 A1 | 5/1991 |
| WO | 9105939 A1 | 5/1991 |
| WO | 9109630 A1 | 7/1991 |
| WO | 9109967 A1 | 7/1991 |
| WO | 9110737 A1 | 7/1991 |
| WO | 9110741 A1 | 7/1991 |
| WO | 9117271 A1 | 11/1991 |
| WO | 9201047 A1 | 1/1992 |
| WO | 9202551 A1 | 2/1992 |
| WO | 9209690 A2 | 6/1992 |
| WO | 9215679 A1 | 9/1992 |
| WO | 9218619 A1 | 10/1992 |
| WO | 9219244 A2 | 11/1992 |
| WO | 9220791 A1 | 11/1992 |
| WO | 9222324 A1 | 12/1992 |
| WO | 9301288 A1 | 1/1993 |
| WO | 9306213 A1 | 4/1993 |
| WO | 9311236 A1 | 6/1993 |
| WO | 9401234 A2 | 1/1994 |
| WO | 9402602 A1 | 2/1994 |
| WO | 9429469 A2 | 12/1994 |
| WO | 9515982 A2 | 6/1995 |
| WO | 9520401 A1 | 8/1995 |
| WO | 96/13518 A1 | 5/1996 |
| WO | 9618978 A1 | 6/1996 |
| WO | 9620698 A2 | 7/1996 |
| WO | 9633735 A1 | 10/1996 |
| WO | 9634096 A1 | 10/1996 |
| WO | 9700957 A1 | 1/1997 |
| WO | 9708320 A1 | 3/1997 |
| WO | 9729131 A1 | 8/1997 |
| WO | 9732572 A2 | 9/1997 |
| WO | 9744013 A1 | 11/1997 |
| WO | 9816280 A1 | 4/1998 |

(56) References Cited

FOREIGN PATENT DOCUMENTS

| | | |
|---|---|---|
| WO | 9816654 A1 | 4/1998 |
| WO | 9824893 A2 | 6/1998 |
| WO | 9825947 A1 | 6/1998 |
| WO | 9831346 A1 | 7/1998 |
| WO | 9831700 A1 | 7/1998 |
| WO | 9847343 A2 | 10/1998 |
| WO | 9849286 A2 | 11/1998 |
| WO | 9850433 A2 | 11/1998 |
| WO | 9901047 A1 | 1/1999 |
| WO | 9911274 A1 | 3/1999 |
| WO | 9915154 A1 | 4/1999 |
| WO | 9920253 A1 | 4/1999 |
| WO | 9925044 A1 | 5/1999 |
| WO | 9936569 A1 | 7/1999 |
| WO | 9945031 A2 | 9/1999 |
| WO | 9945962 A1 | 9/1999 |
| WO | 9951741 A2 | 10/1999 |
| WO | 9953049 A1 | 10/1999 |
| WO | 9954342 A1 | 10/1999 |
| WO | 9966903 A2 | 12/1999 |
| WO | 0002911 A2 | 1/2000 |
| WO | 0005410 A2 | 2/2000 |
| WO | 0009560 A2 | 2/2000 |
| WO | 0014271 A1 | 3/2000 |
| WO | 0017221 A1 | 3/2000 |
| WO | 0037504 A2 | 6/2000 |
| WO | 00037504 A2 | 6/2000 |
| WO | 0056772 A1 | 9/2000 |
| WO | WO 00/73801 | 12/2000 |
| WO | 0154708 A1 | 8/2001 |
| WO | 0158956 A2 | 8/2001 |
| WO | 0183525 A2 | 11/2001 |
| WO | 0190304 A2 | 11/2001 |
| WO | 0202773 A2 | 1/2002 |
| WO | WO 02/051438 | 7/2002 |
| WO | 02072636 A2 | 9/2002 |
| WO | 03004615 A2 | 1/2003 |
| WO | 03016466 A2 | 2/2003 |
| WO | WO 03/031462 | 4/2003 |
| WO | 03035835 A2 | 5/2003 |
| WO | WO 03/089608 | 10/2003 |
| WO | 2004005457 A2 | 1/2004 |
| WO | WO 2004/003150 | 1/2004 |
| WO | 2004067561 A1 | 8/2004 |
| WO | 2004078140 A2 | 9/2004 |
| WO | WO 2004/092405 | 10/2004 |
| WO | 2005016955 A2 | 2/2005 |
| WO | 2005061554 A1 | 7/2005 |
| WO | 2005087268 A1 | 9/2005 |
| WO | 2005100584 A2 | 10/2005 |
| WO | 2006054000 A2 | 5/2006 |
| WO | 06066171 A1 | 6/2006 |
| WO | 2006088972 A2 | 8/2006 |
| WO | 2006094724 A2 | 9/2006 |
| WO | 2006127861 A2 | 11/2006 |
| WO | 2007024715 A2 | 3/2007 |
| WO | 2007058671 A1 | 5/2007 |
| WO | 2007062852 A2 | 6/2007 |
| WO | 2007106507 A2 | 9/2007 |
| WO | 2007141258 A2 | 12/2007 |
| WO | 2008013492 A1 | 1/2008 |
| WO | 2008038599 A1 | 4/2008 |
| WO | 2008073919 A2 | 6/2008 |
| WO | 2008073923 A2 | 6/2008 |
| WO | 2008082651 A2 | 7/2008 |
| WO | 2008085797 A2 | 7/2008 |
| WO | 2008087224 A2 | 7/2008 |
| WO | 2009002386 A2 | 12/2008 |
| WO | 2009006543 A1 | 1/2009 |
| WO | 2009026392 A1 | 2/2009 |
| WO | 2009030500 A1 | 3/2009 |
| WO | 2009092032 A1 | 7/2009 |
| WO | 2009094592 A2 | 7/2009 |
| WO | 2009106356 A1 | 9/2009 |
| WO | 2009140383 A2 | 11/2009 |
| WO | 2009149185 A2 | 12/2009 |
| WO | 2010006060 A2 | 1/2010 |
| WO | 2010006184 A2 | 1/2010 |
| WO | 2010006189 A2 | 1/2010 |
| WO | 2010007144 A2 | 1/2010 |
| WO | 2010017451 A2 | 2/2010 |
| WO | 2010021696 A1 | 2/2010 |
| WO | 2010044506 A2 | 4/2010 |
| WO | 2010062914 A1 | 6/2010 |
| WO | 2010088688 A2 | 8/2010 |
| WO | 2010105298 A1 | 9/2010 |
| WO | 2010127284 A2 | 11/2010 |
| WO | 2011039289 A1 | 4/2011 |
| WO | 2011039734 A2 | 4/2011 |
| WO | 2011068839 A1 | 6/2011 |
| WO | 2011070045 A1 | 6/2011 |
| WO | 2011071059 A1 | 6/2011 |

OTHER PUBLICATIONS

Ngo et al. (1994). Computational complexity, protein structure prediction, and the Levinthal paradox. In Merz and Le Grand (Eds.) The Protein Folding Problem and Tertiary Structure Prediction. Birkhauser:Boston, pp. 491-495.*

Skolnick et al. (2000). From genes to protein structure and function: novel applications of computational approaches in the genomic era, Trends in Biotech. 18(1):34-39.*

Matsunaga, E., et al., "RGM and its receptor neogenin regulate neuronal survival", Nature Cell Biology, Aug. 2004, vol. 6, No. 8, pp. 749-755.

Matsunaga, E., et al., "Repulsive guidance molecule/neogenin: a novel ligand-receptor system playing multiple roles in neural development", Development, Growth & Differentiation, Dec. 2004, vol. 46, No. 6, pp. 481-486.

Rajagopalan, S., et al., "Neogenin mediates the action of repulsive guidance molecule", Nature Cell Biology, Aug. 2004, vol. 6, No. 8, pp. 756-762.

Oldekamp, J., et al., "Expression pattern of the repulsive guidance molecules RGM A, B and C during mouse development", Gene Expression Patters, Elsevier, vol. 4, No. 3, May 2004, pp. 283-288.

International Search Report from International Patent Application No. WO2007/039256 dated Apr. 3, 2007.

Kyoto, et al. "Synapse formation of the cortico-spinal axons is enhanced by RGMa inhibition after spinal cord injury," Brain Research (2007).

GenomeQuest—Sequence Search Report result Feb. 15 11:32 am dated Feb. 15, 2010.

FTO RGM-A Sequence search dated Feb. 15, 2010.

RGM-A human isoform 1 NP_001159755 Blast search dated Feb. 15, 2010.

Mueller, B. et al., "RGM, a repulsive guidance molecule, is involved in retinal axon guidance in vitro." Taniguchi Symposia on Brain Sciences, vol. 20 Mol. Basis of Axon Growth & Nerve Pattern Form 1997, pp. 215-229.

Frisen, J. et al., "Ephrin-A5 (AL-1/RAGS) is essential for proper retinal axon guidance and topographic mapping in the mammalian visual system" Neuron, vol. 20, No. 2, Feb. 1998, pp. 235-243.

Tassew, N.G., et al. "Sustained in vivo inhibition of protein domains using single-chain Fv recombinant antibodies and its application to dissect RGMa activity on axonal outgrowth," The Journal of Neuroscience, Jan. 28, 2009, 29 (4): 1126-1131.

Matsunaga, E., et al., "Repulsive guidance molecule plays multiple roles in neuronal differentiation and axon guidance," The Journal of Neuroscience, May 31, 2006, 26(22): 6082-6088.

Fitzgerald, D.P., et al., Neogenin is expressed on neurogenic and gliogenic progenitors in gene expr. pattern (2007).

Fitzgerald, D.P., et al., "Characterization of neogenin-expressing neural progenitor populations and migrating neuroblasts in the embryonic mouse forebrain," Neuroscience (2006).

Muller, B.K., et al., "Chromophore-assisted laser inactivation of a repulsive axonal guidance molecule," Current Biology 1996, vol. 6, No. 11:1497-1502.

Muller, B.K., et al., "In vitro experiments on axonal guidance and growth-cone collapse," J. esp. Biol. 153, 29-46 (1990).

(56) References Cited

OTHER PUBLICATIONS

Kuby, 1997, Immunology, Third Edition, pp. 131-134.
Alberts, et al., 1994, Molecular Biology of the Cell, Third Edition, pp. 1216-1220.
Beaud M.L., et al., 2008, BMC Neurosci. 9:5.
Giger, R.J., et al., 2008, Restorative Neuroi. Neurosci. 26: 97-115.
Hunt, D., et al. 2002. J. Neurocytol. 31: 93-120.
Iseda, T., et al., 2008. J. Neurotrauma. 25: 334-349.
Muller, B.K., et al. Curr. Biol. 1996, 6(11): 1497-1502.
Steward, O., et al., 2008. Exp. Neurol. 209: 446-468.
Hata, et al., 2006, Journal of Cell Biology, 173(1): 47-58.
Stokes, et al. "Experimental modeling of human spinal cord injury: a model that crosses the species barrier and mimic the spectrum of human cytopathology," Spinal Cord 40: 101-109, 2002.
Talac, et al., "Animal models of spinal cord injury for evaluation of tissue engineering treatment strategies," . Biomaterials 25: 1505-1510, 2004.
Mills, et al., "Strain and model differences in behavior outcomes after spinal cord injury in rat," J. Neurotrauma Aug.; 18(8): 743-756, 2001.
Mautes, et al., "Vascular events after spinal cord injury: contribution to secondary pathogenesis," Phys. Ther. Jul. 2000; 80(7): 673-687.
Letter dated Dec. 23, 1998 from Bernhard Mueller to Dr. Thomas Hesse reporting on the results of research performed during a sabbatical relating to RGM during Jul. 29, 1998 to Sep. 6, 1998. (English translation).
RGM and Retinal Neuronal Regeneration Search—Jan. 25, 2010.
RGM or RGMA or Neogenin Search—Feb. 16, 2010.
Brinks H., et al., "The Repulsive Guidance Molecule RGMa is Involved in the Formation of Afferent Connections in the Dentate Gyrus," The Journal of Neuroscience, 2004, vol. 24 (15), pp. 3862-3869.
Casadevall A., et al., "Immunoglobulin Isotype Influences Affinity and Specificity," Proceedings of the National Academy of Sciences, 2012, vol. 109 (31), pp. 12272-12273.
Genbank Accession No. CAK97872.1, Jun. 30, 2006.
Non-Final Office Action mailed Jul. 19, 2013 for U.S. Appl. No. 13/493,005, filed Jun. 11, 2012.
Birse C.E., et al. Humanpolypeptide, SEQ ID No. 1934 XP002476351.
International Search Report and Written Opinion for Application No. PCT/US2013/023277, mailed on Jun. 5, 2013, 21 pages.
Bowie J.U., et al., "Deciphering the Message in Protein Sequences: Tolerance to Amino Acid Substitutions," Science, 1990, vol. 247 (4948), pp. 1306-1310.
Burgess W.H., et al., "Possible dissociation of the heparin-binding and mitogenic activities of heparin-binding (acidic fibroblast) growth factor-1 from its receptor-binding activities by site-directed mutagenesis of a single lysine residue," Journal of Cell Biology, 1990, vol. 111 (5 Pt 1), pp. 2129-2138.
Frohman E.M., et al., "Modeling Axonal Degeneration within the Anterior Visual System: Implications for Demonstrating Neuroprotection in Multiple Sclerosis," Archives of neurology, 2008, vol. 65 (1), pp. 26-35.
Non-Final Office Action mailed Sep. 18, 2013 for U.S. Appl. No. 13/547,109, filed Jul. 12, 2012.
Non-Final Office Action mailed Aug. 21, 2013 for U.S. Appl. No. 12/963,461, filed Dec. 8, 2010.
Pawson T., et al., "Assembly of Cell Regulatory Systems through Protein Interaction Domains," Science, 2003, vol. 300 (5618), pp. 445-452.
Non-Final Office Action mailed Nov. 22, 2013 for U.S. Appl. No. 14/033,707, filed Sep. 23, 2013.
Final Office Action mailed Jan. 16, 2014 for U.S. Appl. No. 12/677,054, filed Jan. 25, 2013.
Hamilton R.G., "Molecular Engineering: Applications to the Clinical Laboratory," Clinical Chemistry, 1993, vol. 39 (9), pp. 1988-1997.
Notice of Allowance mailed Oct. 31, 2013 for U.S. Appl. No. 13/493,005, filed Jun. 11, 2012.
Osada N., et al., EMBL Accession No. AB046024, Oct. 1, 2000.
Winter G., et al., "Humanized Antibodies," Immunology Today, 1993, vol. 14 (6), pp. 243-246.
Abstracts of the XIIth International Symposium on Bioluminescence and Chemiluminescence to be Held at Robinson College, University of cambridge, England, Apr. 5-9, 2002, Luminescence, 2002, vol. 17, pp. 77-115.
Adamczyk M., et al., "Chemiluminescence Quenching of Pteroic Aacid-N-sulfonyl-acridinium-9-carboxamide Conjugates by Folate Binding Protein," Bioorganic and Medicinal Chemistry Letters, 2004, vol. 14 (9), pp. 2313-2317.
Adamczyk M., et al., "Chemiluminescent Acridinium-9-Carboxamide Boronic Acid Probes: Application to a Homogeneous Glycated Hemoglobin Assay," Bioorganic & Medicinal Chemistry Letters, 2006, vol. 16 (5), pp. 1324-1328.
Adamczyk M., et al., "Chemiluminescent N-Sulfonylacridinium-9-Carboxamides and Their Application in Clinical Assays ," Luminescence Biotechnology: Instruments and Applications , 2002, pp. 77-105.
Adamczyk M., et al., "Homogeneous Chemiluminescent Assays for Free Choline in Human Plasma and Whole Blood ," Analytica Chimica Acta, 2006, vol. 579 (1), pp. 61-67.
Adamczyk M., et al., "Intrinsic Factor-Mediated Modulation of Cyanocobalamin-N-sulfonyl-acridinium-9-carboxamide Chemiluminescence," Bioorganic and Medicinal Chemistry Letters, 2004, vol. 14 (15), pp. 3917-3921.
Adamczyk M., et al., "Linker-Medicated Modulation of the Cheiluminescent Signal from N10-(3-Sulfopropyl)-N-Sulfonylacridinium-9-carboxamide Tracers ," Bioconjugate Chemistry, 2000, vol. 11 (5), pp. 714-724.
Adamczyk M., et al., "Modulation of the Chemiluminescent Signal from N10-(3-Sulfopropyl)-N-Sulfonylacridinium-9-carboxamides ," Tetrahedron, 1999, vol. 55, pp. 10899-10914.
Adamczyk M., et al., "Neopentyl 3-Triflyloxypropanesulfaonate Areactive Sulfopropylation Reagent for the Preparation of Chemiluminescent Labels ," Journal of Organic Chemistry, 1998, vol. 63, pp. 5636-5639.
Adamczyk M., et al., "Regiodependent Luminescence Quenching of Biotinylated N-Sulfonyl-acridinium-9-carboxamides by Avidin ," Organic Letters, 2003, vol. 5 (21), pp. 3779-3782.
Adamczyk M., et al., "Synthesis of a Chemiluminescent Acridinium Hydroxylamine (AHA) for the Direct Detection of Abasic Sites in DNA," Organic Letters , 1999, vol. 1 (5), pp. 779-781.
Albert S.E., et al., "Time-Dependent Induction of Protective Anti-Influenza Immune Responses in Human Peripheral Blood Lymphocyte/SCID Mice," Journal of Immunology, 1997, vol. 159 (3), pp. 1393-1403.
Amann E., et al., "Tightly Regulated Tac Promoter Vectors Useful for the Expression of Unfused and Fused Proteins in *Escherichia coli*," Gene, 1988, vol. 69 (2), pp. 301-315.
Ames R.S., et al., "Conversion of Murine Fabs Isolated from a Combinatorial Phage Display Library to Full Length Immunoglobulins," Journal of Immunological Methods , 1995, vol. 184 (2), pp. 177-186.
Anderson W.F., "Human Gene Therapy," Science, 1992, vol. 256 (5058), pp. 808-813.
Ara J., et al., "Bone Morphogenetic Proteins 4, 6, and 7 are Up-Regulated in Mouse Spinal Cord during Experimental Autoimmune Encephalomyelitis," Journal of Neuroscience Research, 2008, vol. 86 (1), pp. 125-135.
Arai K., et al., "An ELISA to Determine the Biodistribution of Human Monoclonal Antibody in Tumor-Xenografted SCID Mice," Journal of Immunological Methods , 1998, vol. 217 (1-2), pp. 79-85.
Ausubel, et al., Current Protocols in Molecular Biology, 1993, 6.3.1-6.3.6,2.10.1-2.10.1-2.10.16.
Ausubel F.M., et al., "A Compendium of Methods from Current Protocols in Molecular Biology" in: Short Protocols in Molecular Biology, John Wiely & Sons, 1989, Table of Contents.
Ausubel F.M., et al., eds., Current Protocols in Molecular Biology, 1994-1998, vol. 1, John Wiley & Sons Inc, Table of Contents.
Ausubel F.M., et al., in: Current Protocols in Molecular Biology, Greene Publishing Associates and Wiley-interscience, 1987.

(56) References Cited

OTHER PUBLICATIONS

Azzazy H.M., et al., "Phage Display Technology: Clinical Applications and Recent Innovations," Clinical Biochemistry, 2002, vol. 35 (6), pp. 425-445.
Babcook J.S., et al., "A Novel Strategy for Generating Monoclonal Antibodies from Single, Isolated Lymphocytes Producing Antibodies of Defined Specificities," Proceedings of the National Academy of Sciences, 1996, vol. 93 (15), pp. 7843-7848.
Babitt J.L., et al. "Bone Morphogenetic Protein Signaling by Hemojuvelin Regulates Hepcidin Expression, XP002476347," Nature Genetics, 2006, vol. 38 (5), pp. 531-539.
Babitt J.L., et al., "Modulation of Bone Morphogenetic Protein Signaling in Vivo Regulates Systemic Iron Balance," The Journal of Clinical Investigation, 2007, vol. 117 (7), pp. 1933-1939.
Babitt J.L., et al. "Repulsive Guidancemolecule (RGMa), a Dragon Homologue, is Abone Morphogenetic Protein Co-receptor," Journal of Biological Chemistry, 2005, vol. 280 (33), pp. 29820-29827.
Bagnard D., et al., "Semaphorins act as Attractive and Repulsive Guidance Signals during the Development of Cortical Projections," Development, 1998, vol. 125 (24), pp. 5043-5053.
Baldari C., et al., "A Novel Leader Peptide Which Allows Efficient Secretion of a Fragment of Human Interleukin 1 Beta in *Saccharomyces cerevisiae*," The EMBO Journal, 1987, vol. 6 (1), pp. 229-234.
Barbas C.F., et al., "In Vitro Evolution of a Neutralizing Human Antibody to Human Immunodeficiency Virus Type 1 to Enhance Affinity and Broaden Strain Cross-Reactivity," Proceedings of the National Academy of Sciences, 1994, vol. 91 (9), pp. 3809-3813.
Barbas C.F., et al., "Assembly of Combinatorial Antibody Libraries on Phage Surfaces: The Gene III Site," Proceedings of the National Academy of Sciences, 1991, vol. 88 (18), pp. 7978-7982.
Becker D., et al., "New Plant Binary Vectors with Selectable Markers Located Proximal to the Left T-DNA Border," Plant Molecular Biology, 1992, vol. 20 (6), pp. 1195-1197.
Berrar D., et al., "Survival Trees for Analyzing Clinical Outcome in Lung Adenocarcinomas Based on Gene Expression Profiles: Identification of Neogenin and Diacylglycerol Kinase Alpha Expression as Critical Factors," Journal of Computational Biology, 2005, vol. 12 (5), pp. 534-544.
Berzofsky J.A., "Intrinsic and Extrinsic Factors in Protein Antigenic Structure," Science, 1985, vol. 229 (4717), pp. 932-940.
Beschorner R., et al., "Long-term Expression of Heme Oxygenase-1 (HO-1, HSP-32) Following Focal Cerebral Infarctions and Traumatic Brain Injury in Humans," Acta Neuropathologica, 2000, vol. 100 (4), pp. 377-384.
Better M., et al. "*Escherichia coli* Secretion of an Active Chimeric Antibody Fragment," Science, 1988, vol. 240 (4855), pp. 1041-1043.
Bevan M., "Binary Agrobacterium Vectors for Plant Transformation," Nucleic Acids Research, 1984, vol. 12 (22), pp. 8711-8721.
Bird R.E., et al., "Single-Chain Antigen-Binding Proteins," Science, 1988, vol. 242 (4877), pp. 423-426.
Birse, CE and Rosen, CA.: "Humanpolypeptide SEQ ID No. 1934" XP002476351, 2001.
Blomer U., et al., "Highly Efficient and Sustained Gene Transfer in Adult Neurons with a Lentivirus Vector," Journal of Virology, 1997, vol. 71 (9), pp. 6641-6649.
Bocher W.O., et al, "Antigen-specific B and T cells in Human/mouse Radiation Chimera Following Immunization in Vivo," Immunology, 1999, vol. 96 (4), pp. 634-641.
Bodanszky M., et al., "Active Esters and Resins in Peptide Synthesis," Chemistry and Industry, 1966, vol. 38, pp. 1597-1598.
Bombil F., et al., "A Promising Model of Primary Human Immunization in Human-Scid Mouse," Immunobiology, 1996, vol. 195 (3), pp. 360-375.
Bonhoeffer F., et al., "How do Retinal Axons Find their Targets on the Tectum," Trends in Neurosciences, 1984, vol. 7, pp. 378-381.
Bork P., et al., "Go Hunting in Sequence Databases but Watch out for the Traps," Trends in Genetics, 1996, vol. 12 (10), pp. 425-427.
Bork P., "Powers and Pitfalls in Sequence Analysis: The 70% Hurdle," Genome Research, 2000, vol. 10 (4), pp. 398-400.
Boss M.A., et al., "Genetically Engineered Antibodies," Immunology Today, 1985, vol. 6 (1), pp. 12-13.
Bossers K., et al., "Analysis of Gene Expression in Parkinson's Disease: Possible Involvement of Neurotrophic Support and Axon Guidance in Dopaminergic Cell Death," Brain Pathology, 2009, vol. 19 (1), pp. 91-107.
Braisted J.E., et al., "Netrin-1 Promotes Thalamic Axon Growth and is Required for Proper Development of the Thalamocortical Projection," The Journal of Neuroscience, 2000, vol. 20 (15), pp. 5792-5801.
Brawn A., et al., "Topographic Mapping From the Retina to the Midbrain is Controlled by Relative but not Absolute Levels of EphA Receptor Signaling," Cell, 2000, vol. 102 (1), pp. 77-88.
Brenner S.E., "Errors in Genome Annotation," Trends in Genetics, 1999, vol. 15 (4), pp. 132-133.
Brinkmann U., et al., "Phage Display of Disulfide-stabilized Fv Fragments," Journal of Immunological Methods, 1995, vol. 182 (1), pp. 41-50.
Brown J.P., et al., "Protein Antigens of Normal and Malignant Human Cells Identified by Immunoprecipitatin with Monoclonal Antibodies," The Journal of Biological Chemistry, 1980, vol. 255 (11), pp. 4980-4983.
Brown J.P., et al., "Structural Characterization of Human Melanoma-Associated Antigen p97 with Monoclonal Antibodies," The Journal of Immunology, 1981, vol. 127 (2), pp. 539-546.
Buchwald H., et al., "Long-term, Continuous Intravenous Heparin Administration by an Implantable infusion Pump in Ambulatory Patients with Recurrent venous Thrombosis," Surgery, 1980, vol. 88 (4), pp. 507-516.
Burton D.R., et al., "Human Antibodies from Combinatorial Libraries," Advances in Immunology, 1994, vol. 57, pp. 191-280.
Burtrum D., et al., "A Fully Human Monoclonal Antibody to the Insulin-Like Growth Factor I Receptor Blocks Ligand-Dependent Signaling and Inhibits Human Tumor Growth in Vivo," Cancer Research, 2003, vol. 63 (24), pp. 8912-8921.
Camus L., et al., "Molecular Evolution of Hemojuvelin and the Repulsive Guidance Molecule Family," Journal of Molecular Evolution, 2007, vol. 107 (2), pp. 428-431.
Camus L.M., et al., "Molecular Evolution of Hemojuvelin and the Repulsive Guidance Molecule Family," Journal of Molecular Evolution, 2007, vol. 65 (1), pp. 68-81.
Capelli L.P., et al., "Deletion of the RMGA and CHD2 Genes in a Child with Epilepsy and Mental Deficiency," European Journal of Medical Genetics, 2012, pp. 1-3.
Caroni P., et al., "Antibody Against Myelin-associated Inhibitor of Neurite Growth Neutralizes Nonpermissive Substrate Properties of CNS White Matter," Neuron, 1988, vol. 1 (1), pp. 85-96.
Caroni P., et al., "Two Membrane Protein Fractions from Rat Central Myelin with Inhibitory Properties for Neurite Growth and Fibroblast Spreading," Journal of Cell Biology, 1988, vol. 106 (4), pp. 1281-1288.
Carter P., et al., "Humanization of an Anti-p185 HER2 Antibody for Human Cancer Therapy," Proceedings of the National Academy of Sciences, 1992, vol. 89 (10), pp. 4285-4289.
Casset, F., et al., "A Peptie Mimetic of an Anti-CD4 Monoclonal Antibody by Rational Design," Biochemical and Biophysical Research Communications, 2003, vol. 307 (1), pp. 198-205.
Chamat S., et al., "Human Monoclonal Antibodies Isolated from Spontaneous Epstein-Barr Virus-Transformed Tumors of Hu-SPL-SCID Mice and Specific for Fusion Protein Display Broad Neutralizing Activity Toward Respiratory Syncytial Virus," The Journal of Infectious Diseases, 1999, vol. 180 (2), pp. 268-277.
Charron G., et al., "Neuron Specificity of the Neurofilament Light Promoter in Transgenic Mice Requires the Presence of DNA Unwinding Elements," The Journal of Biological Chemistry, 1995, vol. 270 (43), pp. 25739-25745.
Chen M.S., et al., "Nogo-A is a Myelin-associated Neurite Outgrowth Inhibitor and an Antigen for Monoclonal Antibody IN-1," Nature, 2000, vol. 403 (6768), pp. 434-439.
Chen Y., et al., "Selection and Analysis of an Optimized Anti-VEGF Antibody: Crystal Structure of an Affinity-Matured Fab in Complex with Antigen," Journal of Molecular Biology, 1999, vol. 293 (4), pp. 865-881.

(56) References Cited

OTHER PUBLICATIONS

Cheng H.J., et al., "Identification and Cloning of ELF-1, a Developmentally Expressed Ligand for the Mek4 and Sek Receptor Tyrosine Kinases ," Cell, 1994, vol. 79 (1), pp. 157-168.
Cheng P.P., et al., "Hepcidin Expression in Anemia of Chronic Disease and Concomitant Iron deficiency Anemia," Clinical and Experimental Medicine, 2011, vol. 11 (1), pp. 33-42.
Chothia C., et al., "Canonical Structures for the Hypervariable Regions of Immunoglobulins," Journal of Molecular Biology , 1987, vol. 196 (4), pp. 901-917.
Chothia C., et al., "Conformations of Immunoglobulin Hypervariable Regions," Nature, 1989, vol. 342 (6252), pp. 877-883.
Chothia C., et al., "Structural Repertoire of the Human VH Segments," Journal of Molecular Biology , 1992, vol. 227 (3), pp. 799-817.
Clackson T., et al., "Making Antibody Fragments Using Phage Display Libraries," Nature, 1991, vol. 352 (6336), pp. 624-628.
Cleek R.L., et al., "Biodegradable Polymeric Carriers for a bFGF Antibody for Cardiovascular Application," Proc. Intl. Symp. Control. Rel. Bioact. Mater., 1997, vol. 24, pp. 853-854.
Co M.S., et al., "Genetically Engineered Deglycosylation of the Variable Domain Increases the Affinity of an Anti-CD33 Monoclonal Antibody," Molecular Immunology, 1993, vol. 30 (15), pp. 1361-1367.
Conrad S., et al., "Neogenin-RGMa Signaling at the Growth Cone is Bone Morphogenetic Protein-independent and Involves RhoA, ROCK, and PKC," The Journal of Biological Chemistry, 2007, vol. 282 (22), pp. 16423-16433.
Conrad U., et al., "Compartment-specific Accumulation of Recombinant Immunoglobulins in Plant Cells: An Essential Tool for Antibody Production and Immunomodulation of Physiological Functions and Pathogen Activity," Plant Molecular Biology, 1998, vol. 38 (1-2), pp. 101-109.
Co-pending U.S. Appl. No. 60/126,603, filed Mar. 25, 1999.
Co-pending U.S. Appl. No. 61/142,048, filed Dec. 31, 2008.
Corder E.H., et al., "Gene Dose of Apolipoprotein E Type 4 Allele and the Risk of Alzheimer'S Disease in Late Onset Families," Science, 1993, vol. 261 (5123), pp. 921-923.
Cox E.C., et al., "Axonal Guidance in the Chick Visual System: Posterior Tectal Membranes Induce Collapse of Growth Cones from the Temporal Retina," Neuron, 1990, vol. 4 (1), pp. 31-37.
Cramer C.L., et al., "Transgenic Plants for Therapeutic Proteins: Linking Upstream and Downstream Strategies," Current Topics in Microbiology and Immunology, 1999, vol. 240, pp. 95-118.
David S., et al., "Axonal Elongation into Peripheral Nervous System "Bridges" After Central Nervous System Injury in Adult Rats," Science, 1981, vol. 214 (4523), pp. 931-933.
Davis S., et al., "Ligands for EPH-Related Receptor Tyrosine Kinases that Require Membrane Attachment or Clustering for Activity," Science, 1994, vol. 266 (5186), pp. 816-819.
De Pascalis R., et al., "Grafting of "Abbreviated" Complementarity-Determining Regions Containing Specificity-Determining Residues Essential for Ligand Contact to Engineer a Less Immunogenic Humanized Monoclonal Antibody," Journal of Immunological Methods, 2002, vol. 169 (6), pp. 3076-3084.
Divry P., "Histochemical Study of the Senile Plates," Journal De Neurologie Et De Psychiatrie, 1927, vol. 27, pp. 643-657.
Doerks T., et al., "Protein Annotation: Detective work for Function Prediction," Trends in Genetics, 1998, vol. 14 (6), pp. 248-250.
Drescher U., et al., "In Vitro Guidance of Retinal Ganglion Cell Axons by Rags, a 25 kDa Tectal Protein Related to Ligands for EPH Receptor Tyrosine Kinases," Cell, 1995, vol. 82 (3), pp. 359-370.
During M. J., et al., "Controlled Release of Dopamine from a Polymeric Brain Implant: In Vivo Characterization," Annals of Neurology, 1989, vol. 25 (4), pp. 351-356.
Elmer L.W., et al., "The Increasing Role of Monoamine Oxidase Type B Inhibitors in Parkinson's Disease Therapy," Expert Opinion on Pharmacotherapy, 2008, vol. 9 (16), pp. 2759-2772.

Eren R., et al., "Human Monoclonal Antibodies Specific to Hepatitis B Virus Generated in a Human/mouse Radiation Chimera: the Trimera System," Immunology, 1998, vol. 93 (2), pp. 154-161.
European Search Report for Application No. EP07115856, mailed on Apr. 15, 2008, 8 pages.
Famulok M., et al., "Oligonucleotide Libraries—Variatio Delectat," Current Opinion in Chemical Biology, 1998, vol. 2 (3), pp. 320-327.
Fanger M.W., et al., "Production and Use of Anti-FcR Bispecific Antibodies," Immunomethods, 1994, vol. 4 (1), pp. 72-81.
Fazeli A., et al., "Phenotype of Mice Lacking Functional Deleted in Colorectal Cancer (Dcc) Gene," Nature, 1997, vol. 386 (6627), pp. 796-804.
Feldheim D.A., et al., "Genetic Analysis of Ephrin-A2 and Ephrin-A5 Shows their Requirement in Multiple Aspects of Retinocollicular Mapping," Neuron, 2000, vol. 25 (3), pp. 563-574.
Feldheim D.A., et al., "Topographic Guidance Labels in a Sensory Projection to the Forebrain," Neuron, 1998, vol. 21 (6), pp. 1303-1313.
Feys T., et al., "A Detailed Inventory of DNA Copy Number Alterations in Four Commonly used Hodgkin's Lymphoma Cell Lines," Haematologica, 2007, vol. 92 (7), pp. 913-920.
Final Office Action mailed Dec. 22, 2011 for U.S. Appl. No. 12/939,823, filed Nov. 4, 2010.
Final Office Action mailed Oct. 28, 2011 for U.S. Appl. No. 12/389,927, filed Feb. 20, 2009.
Fishwild D.M., et al., "High-Avidity Human IgGK Monoclonal Antibodies from a Novel Strain of Minilocus Transgenic Mice," Nature Biotech, 1996, vol. 14 (7), pp. 845-851.
Fitzgerald D.P., et al., "Characterization of Neogenin-expressing Neural Progenitor Populations and Migrating Neuroblasts in the Embryonic Mouse Forebrain," Neuroscience, 2006, vol. 142 (3), pp. 703-716.
Fitzgerald D.P., et al., "Neogenin is Expressed on Neurogenic and Gliogenic Progenitors in the Embryonic and Adult Central Nervous System," Gene Expression Patterns, 2007, vol. 7 (7), pp. 784-792.
Flanagan J.G., et al., "The Ephrins and Eph Receptors in Neural Development," Annual Review Neuroscience, 1998, vol. 21, pp. 309-345.
Foote J., et al., "Antibody Framework Residues Affecting the Conformation of the Hypervariable Loops," Journal of Molecular Biology, 1992, vol. 224 (2), pp. 487-499.
Fournier A.E., et al., "Identification of a Receptor Mediating Nogo-66 Inhibition of Axonal Regeneration," Nature, 2001, vol. 409 (6818), pp. 341-346.
Fuchs P., et al., "Targeting Recombinant Antibodies to the Surface of *Escherichia coli*: Fusion to a Peptidoglycan Associated Lipoprotein," BioTechnology, 1991, vol. 9 (12), pp. 1369-1372.
Funaro A., et al., "Generation of Potent Neutralizing Human Monoclonal Antibodies Against Cytomegalovirus Infection from Immune B Cells," BMC Biotechnol, 2008, vol. 8:85, 10 pages.
Galfre G., et al., "Antibodies to Major Histocompatibility Antigens Produced by Hybrid Cell Lines," Nature, 1977, vol. 266 (5602), pp. 550-552.
Gallo M.L., et al., "The Human Immunoglobulin Loci Introduced into Mice: V (D) and J Gene Segment Usage Similar to that of Adult Humans," European Journal of Immunology , 2000, vol. 30 (2), pp. 534-540.
Ganz T., "Hepcidin and Iron Regulation, 10 Years Later," Blood, 2011, vol. 117 (17), pp. 4425-4433.
Garrard L.J., et al., "Fab Assembly and Enrichment in a Monovalent Phage Display System," BioTechnology, 1991, vol. 9 (12), pp. 1373-1377.
Gavilondo J.V., et al., "Antibody Engineering at the Millennium," Biotechniques, 2000, vol. 29 (1), pp. 128-145.
Geddes B.J., et al., "Assessing Viral Gene Therapy in Neuroendocrine Models," Front in Neuroendocrinology, 1999, vol. 20 (4), pp. 296-316.
Geddes B.J., et al., "Long-term Gene Therapy in the CNS: Reversal of Hypothalamic Diabetes Insipidus in the Brattleboro Rat by using an Adenovirus Expressing Arginine Vasopressin," Nature Medicine, 1997, vol. 3 (12), pp. 1402-1404.

(56) References Cited

OTHER PUBLICATIONS

Gefter M.L., et al., "A Simple Method for Polyethylene Glycol-Promoted Hybridization of Mouse Myeloma Cells," Somatic Cell Genetics, 1997, vol. 3 (2), pp. 231-236.
Geisbrecht B.V., et al., "Netrin Binds Discrete Subdomains of DCC and UNC5 and Mediates Interactions between DCC and Heparin," The Journal of Biological Chemistry, 2003, vol. 278 (35), pp. 32561-32568.
Genbank Accession No. AK080819, Mar. 3, 2004.
Genbank Accession No. BC023870, Feb. 24, 2004.
Genbank Accession No. BCO22603, Jan. 3, 2005.
Genbank Accession No. BI769500, Sep. 25, 2001.
Genbank Accession No. BI818609, Oct. 4, 2001.
Genbank Accession No. NM008684, Feb. 28, 2005.
Genbank Accession No. NT039474, Aug. 31, 2004.
Genbank, "Hemojuvelin Isoform a Precursor [*Homo sapiens*]", Accession No. NP_998818.1, Jun. 30, 2012.
Genbank, "*Homo sapiens* RGM Domain Family, Member A (RGMA), Transcript Variant 4, mRNA", Accession No. NM_020211.2, Jun. 29, 2012.
Genbank, "Repulsive Guidance Molecule A Isoform 3 [*Homo sapiens*]", Accession No. NP_064596.2, 29 Jun. 2012.
Genbank, "RGM Domain Family Member B [*Homo sapiens*]", Accession No. NP_001012779.2, Jul. 1, 2012.
Gennaro A.R., ed., Remington: The Science and Practice of Pharmacy, 19th Edition, Mack Publishing, 1995, Table of Contents.
GenomeQuest—Sequence Search Report result Feb. 15 11:32 am (redo 1) dated Feb. 15, 2010.
Gheith M.E., et al., "Managing Refractory Glaucoma with a Fixed Combination of Bimatoprost (0.03%) and Timolol (0.5%)," Clinical Ophthalmology, 2008, vol. 2 (1), pp. 15-20.
Giege R., et al., "An Introduction to the Crystallogenesis of Biological Macromolecules" in: Crystallization of Nucleic Acids and Proteins, Chapter 1, 2nd Edition, Ducruix A., et al., Eds., Oxford University Press, 1999, pp. 1-16.
Gierer A., "Directional Cues for Growing Axons Forming the Retinotectal Projection," Development, 1987, vol. 101 (3), pp. 479-489.
Gillies S.D., et al., "High-Level Expression of Chimeric Antibodies Using Adapted cDNA Variable Region Cassettes," Journal of Immunological Methods, 1989, vol. 125 (1-2), pp. 191-202.
Giordano F.J., et al., "Intracoronary Gene Transfer of Fibroblast Growth Factor-5 Increases Blood Flow and Contractile Function in an Ischemic Region of the Heart," Nature Medicine, 1996, vol. 2 (5), pp. 534-539.
Gisin, Helvetica Chimica Acta, 1973, vol. 56, pp. 1467.
Glenner G.G., "Amyloid Deposits and Amyloidosis. The Beta-Fibrilloses (First of Two Parts)," The New England Journal of Medicine, 1980, vol. 302 (23), pp. 1283-1292.
Gnana-Prakasam J.P., et al., "Iron-mediated Retinal Degeneration in Haemojuvelin-knockout Mice," The Biochemical Journal, 2012, vol. 441 (2), pp. 599-608.
Goeddel D.V., "Systems for Heterologous Gene Expression," Methods in Enzymology, 1990, vol. 185, pp. 3-7.
Gold L., et al., "Diversity of Oligonucleotide Functions," Annual Review of Biochemistry, 1995, vol. 64, pp. 763-797.
Goldspiel B.R., et al., "Human Gene therapy," Clinical Pharmacy, 1993, vol. 12 (7), pp. 488-505.
Goodhill G.J., "Dating Behavior of the Retinal Ganglion Cell," Neuron, 2000, vol. 25 (3), pp. 501-503.
Goodman C.S., "Mechanisms and Molecules that Control Growth Cone Guidance," Annual Review of Neuroscience, 1996, vol. 19, pp. 341-377.
Goodson J.M., "Dental Applications" in: Medical Applications of Controlled Release, vol. 2, Chapter 6, Langer R.S., et al., eds., CRC Press, 1984, pp. 115-138.
Graham D.I., et al., Trauma, Chapter 5, 1996, pp. 197-248.
Gram H., et al., "In Vitro Selection and Affinity Maturation of Antibodies from a Naïve Combinatorial Immunoglobulin Library," Proceedings of the National Academy of Sciences, 1992, vol. 89 (8), pp. 3576-3580.
Grandpre T., et al., "Identification of the Nogo Inhibitor of Axon Regeneration as a Reticulon Protein," Nature, 2000, vol. 403 (6768), pp. 439-444.
Gray F., et al., "Secretion Capture and Report Web: use of Affinity Derivatized Agarose Microdroplets for the Selection of Hybridoma Cells," Journal of Immunological Methods, 1995, vol. 182 (2), pp. 155-163.
Green L. L., et al., "Regulation of B Cell Development by Variable Gene Complexity in Mice Reconstituted with Human Immunoglobulin Yeast Artificial Chromosomes," Journal of Experimental Medicine, 1998, vol. 188 (3), pp. 483-495.
Green L.L., "Antibody Engineering via Genetic Engineering of the Mouse: XenoMouse Strains are a Vehicle for the Facile Generation of Therapeutic Human Monoclonal Antibodies," Journal of Immunological Methods, 1999, vol. 231 (1-2), pp. 11-23.
Green L.L., et al., "Antigen-Specific Human Monoclonal Antibodies from Mice Engineered with Human Ig Heavy and Light Chain YACs," Nature Genetics, 1994, vol. 7 (1), pp. 13-21.
Griffiths A.D., et al., "Human Anti-Self Antibodies with High Specificity from Phage Display Libraries," European Molecular Biology Organization, 1993, vol. 12 (2), pp. 725-734.
Halbrooks P.J., et al., "Role of RGM Coreceptors in Bone Morphogenetic Protein Signaling," Journal of Molecular Signaling, 2007, vol. 2:4, 10 pages.
Hall A.K., et al., "Emerging Roles for Bone Morphogenetic Proteins in Central Nervous System Glial Biology," Journal of Neuroscience Research, 2004, vol. 76 (1), pp. 1-8.
Hammerling G.J., et al., Eds., Monoclonal Antibodies and T-Cell Hybridomas : Perspectives and Technical Advances, Elsevier/North-Holland Biomedical Press, 1981, Appendix, pp. 563-587.
Hanes J., et al., "In Vitro Selection and Evolution of Functional Proteins by using Ribosome Display," Proceedings of the National Academy of Sciences, 1997, vol. 94 (10), pp. 4937-4942.
Hanes J., et al., "Ribosome Display Efficiently Selects and Evolves High-Affinity Antibodies in Vitro from Immune Libraries," Proceedings of the National Academy of Sciences, 1998, vol. 95 (24), pp. 14130-14135.
Hanson L.R., et al., "Intranasal Delivery Bypasses the Blood-Brain Barrier to Target Therapeutic Agents to the Central Nervous System and Treat Neurodegenerative Disease," BMC Neuroscience, 2008, vol. 9 (Suppl 3), pp. S5.
Harding F.A., et al., "Class Switching in Human Immunoglobulin Transgenic Mice," Annals New York Academy of Sciences, 1995, vol. 764, pp. 536-546.
Harel N.Y., et al., "Can Regenerating Axons Recapitulate Developmental Guidance During Recovery from Spinal Cord Injury," Nature Reviews Neuroscience, 2006, vol. 7 (8), pp. 603-616.
Harlow E., et al., Antibodies: A Laboratory Manual, Cold Spring Harbor Laboratory Press, 1988, pp. 555-561, 578-582 and 591-592.
Harlow, et al., "Production of Antibody-Producing Hybridomas in the Rodent Systems," Monoclonal Antibod. And T-Cell Hybrid., pp. 563-681, 1989.
Haugland., et al., "Handbook of Fluorescent Probes and Research Chemicals," Molecular Probes, 1996, Table of Contents.
Hawkins R.E., et al., "Selection of Phage Antibodies by Binding Affinity Mimicking Affinity Maturation," Journal of Molecular Biology, 1992, vol. 226 (3), pp. 889-896.
Hay B.N., et al., "Bacteriophage Cloning and *Escherichia coli* Expression of a Human IgM Fab," Human Antibodies and Hybridomas, 1992, vol. 3 (2), pp. 81-85.
Heard C., et al., "Two Neutralizing Human Anti-RSV Antibodies: Cloning, Expression, and Characterization," Molecular Medicine, 1999, vol. 5 (1), pp. 35-45.
Hentze M.W., et al., "Two to Tango: Regulation of Mammalian Iron Metabolism," Cell, 2010, vol. 142 (1), pp. 24-38.
Herz U. et al., "The Humanized (Hu-Pbmc) Scid Mouse as an in vivo Model for Human Ige Production and Allergic Inflammation of the Skin," International Archives of Allergy and Immunology, 1997, vol. 113 (1-3), 150-152.

(56) References Cited

OTHER PUBLICATIONS

Heukeshoven J., et al., "Improved Silver Staining Procedure for Fast Staining in Phastsystem Development Unit .I. Staining of Sodium Dodecyl Sulfate Gels," Electrophoresis, 1988, vol. 9 (1), pp. 28-32.
Heukeshoven J., et al., "Increased Sensitivity for Coomassie Staining of Sodium Dodecyl Sulfate-Polyacrylamide Gels Using Phastsystem Development Unit," Electrophoresis, 1988, vol. 9 (1), pp. 60-61.
Higgins D.G., et al., "Fast and Sensitive Multiple Sequence Alignments on a Microcomputer," Computer Applications in the Biosciences, 1989, vol. 5 (2), pp. 151-153.
Holliger P., et al., ""Diabodies": Small Bivalent and Bispecific Antibody Fragments," Proceedings of the National Academy of Sciences, 1993, vol. 90 (14), pp. 6444-6448.
Hong K., et al., "A Ligand-Gated Association Between Cytoplasmic Domains of Unc5 and Dcc Family Receptors Converts Netrin-Induced Growth Cone Attraction to Repulsion," Cell, 1999, vol. 97 (7), pp. 927-941.
Hood E.E., et al., "Molecular Farming of industrial Proteins from Transgenic Maize," Advances in Experimental Medicine and Biology, 1999, vol. 464, pp. 127-147.
Hoogenboom H.R., et al., "Designing and Optimizing Library Selection Strategies for Generating High-Affinity Antibodies," Trends in Biotechnology, 1997, vol. 15 (2), pp. 62-70.
Hoogenboom H.R., et al., "Multi-Subunit Proteins on the Surface of Filamentous Phage: Methodologies for Displaying Antibody (Fab) Heavy and Light Chains," Nucleic Acids Research, 1991, vol. 19 (15), pp. 4133-4137.
Hoogenboom H.R., et al., "Natural and Designer Binding Sites Made by Phage Display Technology," Immunology Today, 2000, vol. 21 (8), pp. 371-378.
Horsley M.B., et al., "Retinal Nerve Fiber Layer Thickness in Patients Receiving Chronic Anti-Vascular Endothelial Growth Factor Therapy," American Journal of Ophthalmology, 2010, vol. 150 (4), pp. 558-561.
Howard M.A., et al., "Intracerebral Drug Delivery in Rats with Lesion-Induced Memory Deficits," Journal of Neurosurgery, 1989, vol. 71 (1), pp. 105-112.
Hu Y.C., et al., "Identification of Differentially Expressed Genes in Esophageal Squamous Cell Carcinoma (Escc) by Cdna Expression Array: Overexpression of Fra-1, Neogenin, Id-1, and Cdc25b Genes in Escc," Clinical Cancer Research, 2001, vol. 7 (8), pp. 2213-2221.
Huang Fw., et al., "A Mouse Model of Juvenile Hemochromatosis," The Journal of Clinical Investigation, 2005, vol. 115 (8), pp. 2187-2191.
Hurrell., G.R., ed., "Monoclonal Hybridoma Antibodies" in: Techniques and Applications, CRC Press Inc., Boco Raron, FL, 1982, Table of Contents.
Huse W.D., et al., "Generation of a Large Combinatorial Library of the Immunoglobulin Repertoire in Phage Lambda," Science, 1989, vol. 246 (4935), pp. 1275-1281.
Huston J.S., et al., "Protein Engineering of Antibody Binding Sites: Recovery of Specific Activity in an Anti-Digoxin Single-Chain Fv Analogue Produced in *Escherichia coli*," Proceedings of the National Academy of Sciences, 1988, vol. 85 (16), pp. 5879-5883.
Huston J.S., et al., "Protein Engineering of Single-Chain Fv Analogs and Fusion Proteins," Methods in Enzymology, 1991, vol. 203, pp. 46-88.
Hutchins W.A., et al., "Human Immune Response to a Peptide Mimic of Neisseria meningititis Serogroup C in hu-PBMC-SCID Mice," Hybridoma, 1999, vol. 18 (2), pp. 121-129.
Ike Y., et al., "Solid Phase Synthesis of Polynucleotides. VIII. Synthesis of Mixed Oligodeoxyribonucleotides by the Phosphotriester Solid Phase Method", Nucleic Acids Research, 1983, vol. 11 (2), pp. 477-488.
Ilan E., et al., "The Hepatitis B Virus-Trimera Mouse: A Model for Human HBV Infectoin and Evaluation of Anti-HBV Therapeutic Agents," Hepatology, 1999, vol. 29 (2), pp. 553-562.
International Search Report for Application No. PCT/EP2001/015289, mailed on May 13, 2003, 6 pages.
International Search Report and Written Opinion for Application No. PCT/EP2008/007339, mailed on Feb. 9, 2009, 12 pages.
International Search Report and Written Opinion for Application No. PCT/EP2010/69120, mailed on May 4, 2011.
International Search Report for Application No. PCT/EP2009/001437, mailed on Jun. 18, 2009, 3 pages.
International Search Report for Application No. PCT/US2003/020147, mailed on Jun. 21, 2004, 1 page.
Isner J.M., et al., "Clinical Evidence of Angiogenesis after Arterial Gene Transfer of phVEGF165 in Patient with Ischaemic Limb," Lancet, 1996, vol. 348 (9024), pp. 370-374.
Isogai, T. et al., "Novel protein sequence#944, XP002476349,", 2004.
Itakura K., et al., "Expression in *Escherichia coli* of a Chemically Synthesized Gene for the Hormone Somatostatin", Science, 1984, vol. 198 (4321), pp. 1056-1063.
Itakura K., et al., "Synthesis and Use of Synthetic Oligonucleotides," Annual Review of Biochemistry, 1984, vol. 53, pp. 323-356.
Itokazu T., et al., "Identification of the Neogenin-Binding Site on the Repulsive Guidance Molecule A," PLoS One, 2012, vol. 7 (3), pp. e32791.
Jackson J.R., et al., "In Vitro Antibody Maturation Improvement of a High Affinity, Neutralizing Antibody Against IL-1β," The Journal of Immunology, 1995, vol. 154 (7), pp. 3310-3319.
Jefferis R., "Glycosylation of Recombinant Antibody Therapeutics," Biotechnology Program, 2005, vol. 21 (1), pp. 11-16.
Johnsson B., et al., "Comparison of Methods for Immobilization to Carboxymethyl Dextran Sensor Surfaces by Analysis of the Specific Activity of Monoclonal Antibodies," Journal of Molecular Recognition, 1995, vol. 8 (1-2), pp. 125-131.
Johnsson B., et al., "Immobilization of Proteins to a Carboxymethyldextran-Modified Gold Surface for Biospecific Interaction Analysis in Surface Plasmon Resonance Sensors," Analytical Biochemistry, 1991, vol. 198 (2), pp. 268-277.
Joliot A., et al., "Antennapedia Homeobox Peptide Regulates Neural Morphogenesis," Proceedings of the National Academy of Sciences, 1991, vol. 88 (5), pp. 1864-1868.
Jones P.T., et al., "Replacing the Complementarity-Determining Regions in a Human Antibody with those from a Mouse," Nature, 1986, vol. 321 (6069), pp. 522-525.
Jonsson U., et al., "Introducing a Biosensor Based Technology for Real-Time Biospecific Interaction Analysis," Annales de Biologie Clinique, 1993, vol. 51 (1), pp. 19-26.
Jonsson U., et al., "Real-Time Biospecific Interaction Analysis Using Surface Plasmon Resonance and a Sensor Chip Technology," Biotechniques, 1991, vol. 11 (5), pp. 620-627.
Jost W.H., et al., "Initial Experience with Ropinirole PR (Prolonged Release)," Journal of Neurology, 2008, vol. 255 (Suppl 5), pp. 60-63.
Kabat E.A., et al., "Attempts to Locate Complementarity-Determining Residues in the variable Positions of Light and Heavy Chains," Annals New York Academy of Sciences, 1971, vol. 190, pp. 382-393.
Kabat E.A., et al., "Sequences of Proteins of Immunological Interest," 1991, 5th Edition, National Institutes of Health Publication, Table of Contents.
Kabat E.A., et al., in: Sequence of Proteins of Immunological Interest, 4th Edition, 1987, Table of Contents.
Kalimo H., et al., "Vascular Diseases", in: Greenfield's Neuropathology, Chapter 7, Graham D.I., et al., eds., Oxford University Press, 1997, pp. 315-396.
Kasus-Jacobi A., et al., "Evidence for an Interaction Between the Insulin Receptor and Grb7. A Role for Two of Its Binding Domains, PIR and SH2," Oncogene, 2000, vol. 19 (16), pp. 2052-2059.
Kato H., et al., "The Initiation of the Microglial Response," Brain Pathology, 2000, vol. 10 (1), pp. 137-143.
Kaufman R. J., et al., Translational Efficiency of Polycistronic mRNAs and their Utilization to Express Heterologous Genes in Mammalian Cells, EMBO, 1987, vol. 6 (1), pp. 187-193.
Kaufman R.J., et al., "Amplification and Expression of Sequences Cotransfected with a Modular Dihydrofolate Reductase Complementary Dna Gene," Journal of Molecular Biology, 1982, vol. 159 (4), pp. 601-621.

(56) References Cited

OTHER PUBLICATIONS

Keeling S.L., et al., "Mouse Neogenin, a DCC-like molecule, has Four Splice Variants and is Expressed widely in the Adult Mouse and during Embryogenesis," Oncogene, 1997, vol. 15 (6), pp. 691-700.
Keino-Masu K., et al., "Deleted in Colorectal Cancer (DCC) Encodes a Netrin Receptor," Cell, 1996, vol. 87 (2), pp. 175-185.
Kellermann S.A., et al., "Antibody Discovery: The Use of Transgenic Mice to Generate Human Monoclonal Antibodies for Therapeutics," Current Opinion in Biotechnology, 2002, vol. 13 (6), pp. 593-597.
Kennett R.H., et al., eds., "Monoclonal Antibodies" in: A New Dimension in Biological Analyses, Plenum Press, 1980, Table of Contents.
Kenney J.S., et al., "Production of Monoclonal Antibodies using a Secretion Capture Report Web," Biotechnology, 1995, vol. 13 (8), pp. 787-790.
Kettleborough C.A., et al., "Isolation of Tumor Cell-specific Single-chain Fv from Immunized Mice using Phage-antibody Libraries and the Re-construction of Whole Antibodies from these Antibody Fragments," European Journal of Immunology, 1994, vol. 24 (4), pp. 952-958.
Khachaturian Z.S., "Diagnosis of Alzheimer's Disease," Archives of Neurology, 1985, vol. 42, pp. 1097-1105.
Khor S.P., et al., "The Pharmacokinetics and Pharmacodynamics of Levodopa in the Treatment of Parkinson's Disease," Current Clinical Pharmacology, 2007, vol. 2 (3), pp. 234-243.
Kipriyanov S.M., et al., "Single-Chain Antibody Streptavidin Fusions: Tetrameric Bifunctional scFv-Complexes with Biotin Binding Activity and Enhanced Affinity to Antigen," Human Antibodies and Hybridomas, 1995, vol. 6 (3), pp. 93-101.
Kipriyanov S.M., et al., "Recombinant Single-Chain Fv Fragments Carrying C-Terminal Cysteine Residues: Production of Bivlent and Biotinylated Miniantibodies," Molecular Immunology, 1994, vol. 31 (14), pp. 1047-1058.
Kirschner D.A., et al., "X-Ray Diffraction from Intraneuronal Paired Helical Filaments and Extraneuronal Amyloid Fibers in Alzheimer Disease Indicates Cross-Beta Conformation," Proceedings of the National Academy of Sciences, 1986, vol. 83 (2), pp. 503-507.
Kitayama M., et al., "Activated Microglia Inhibit Axonal Growth through RGMa," PLoS One, 2011, vol. 6 (9), pp. e25234.
Knappik A., et al., "Fully Synthetic Human Combinatorial Antibody Libraries (hUCAL)Based on Modular Consensus Frameworks and CDRs Randomized with Trinucleotides," Journal of Molecular Biology, 2000, vol. 296 (1), pp. 57-86.
Knoll B., et al., "Stripe Assay to Examine Axonal Guidance and Cell Migration," Nature Protocols, 2007, vol. 2 (5), pp. 1216-1224.
Koeberle P.D., et al., "The Repulsive Guidance Molecule, RGMa, Promotes Retinal Ganglion Cell Survival in Vitro and in Vivo," Neuroscience, 2010, vol. 169 (1), pp. 495-504.
Kohler G., et al., "Continuous Cultures of Fused Cells Secreting Antibody of Predefined Specificity ," Nature, 1975, vol. 256 (5517), pp. 495-497.
Kolodkin A.L., et al., "The Semaphorin Genes Encode a Family of Transmembrane and Secreted Growth Cone Guidance Molecules," Cell, 1993, vol. 75 (7), pp. 1389-1399.
Konig K., et al., "The Axonal Guidance Receptor Neogenin Promotes Acute Inflammation," PLoS One, 2012, vol. 7 (3), pp. e32145.
Kontermann R., et al., eds., Antibody Engineering, Springer-Verlag Berlin Heidelberg, 2001, Table of Contents.
Korchynskyi O., et al., "Identification and Functional Characterization of Distinct Critically Important Bone Morphogenetic Protein-Specific Response Elements in the Id1 Promoter," Journal of Biological Chemistry, 2002, vol. 277 (7), pp. 4883-4891.
Kriegler M., Gene Transfer and Expression: A Laboratory Manual, Stockton Press, 1990, Table of Contents.
Kubo T., et al., "Crosstalk Between the Immune and Central Nervous Systems with Special Reference to Drug Development", Chapter 14, 2011, pp. 365-380.
Kurjan J., et al., "Structure of a Yeast Pheromone Gene (MF Alpha): A Putative Alpha-Factor Precursor Contains Four Tandem Copies of Mature Alpha-Factor," Cell, 1982, vol. 30 (3), pp. 933-943.

Kyte J., et al., "A Simple Method for Displaying the Hydropathic Character of a Protein," Journal of Molecular Biology, 1982, vol. 157 (1), pp. 105-132.
Lah G.J., et al., "Dual Roles of the Chemorepellent Axon Guidance Molecule RGMA in Establishing Pioneering Axon Tracts and Neural Fate Decisions in Embryonic Vertebrate Forebrain," Developmental Neurobiology, 2012.
Lah G.J., et al., "Novel Roles of the Chemorepellent Axon Guidance Molecule Rgma in Cell Migration and Adhesion," Molecular and Cellular Biology, 2012, vol. 32 (5), pp. 968-980.
Lai M., et al., "Focal Brain Injury Increases Activin BetaA mRNA Expression in Hippocampal Neurons," Neuroreport, 1997, vol. 8 (12), pp. 2691-2694.
Lam X.M., et al., "Microencapsulation of Recombinant Humanized Monoclonal Antibody for Local Delivery," Proceedings of the 24th International Symposium on Controlled Release of Bioactive Materials, 1997, vol. 24, pp. 759-760.
Lamminmaki U., et al., "Crystal Structure of a Recombinant Anti-Estradiol Fab Fragment in Complex with 17beta-Estradiol," The Journal of Biological Chemistry, 2001, vol. 276 (39), pp. 36687-36694.
Langer R., et al., "Chemical and Physical Structure of Polymers as Carriers for Controlled Rlease of Bioactive Agents: A Review," Journal of Macromolecular Science—Reviews in Macromolecular Chemistry & Physics, 1983, vol. C23 (1), pp. 61-126.
Langer R., "New Methods of Drug Delivery," Science, 1990, vol. 249 (4976), pp. 1527-1533.
Langer R.S., et al., eds., Medical Applications of Controlled Release: Applications and Evaluation, vol. 2, CRC Press, 1984, pp. 113-138.
Leader K.A., et al., "Antibody Responses to the Blood Group Antigen D in SCID Mice Reconstituted with Human Blood Mononuclear Cells," Immunology, 1992, vol. 76 (2), pp. 229-234.
Lerner E.A., "How to Make a Hybridoma," The Yale Journal of Biology & Medicine, 1981, vol. 54 (5), pp. 387-402.
Levy R.D., et al., "Inhibition of Calcification of Bioprosthetic Heart Valves by Local Controlled Release Diphosphonate," Science, 1985, vol. 228 (4696), pp. 190-192.
Li J., et al., "Potential Prognostic Value of Repulsive Guidance Molecules in Breast Cancer," Anticancer Research, 2011, vol. 31 (5), pp. 1703-1711.
Li J., et al., "Repulsive Guidance Molecule B (RGMB) Plays Negative Roles in Breast Cancer by Coordinating BMP Signaling," Journal of Cellular Biochemistry , 2012, vol. 113 (7), pp. 2523-2531.
Li J., et al., "Repulsive Guidance Molecules, Novel Bone Morphogenetic Protein Co-Receptors, are Key Regulators of the Growth and Aggressiveness of Prostate Cancer Cells," International Journal of Oncology, 2012, vol. 40 (2), pp. 544-550.
Liang B.A., et al., "Review of Tissue Plasminogen Activator, Ischemic Stroke, and Potential Legal Issues," Archives of Neurology, 2008, vol. 65 (11), pp. 1429-1433.
Lingor P., et al., "Inhibition of Rho Kinase (Rock) Increases Neurite Outgrowth on Chondroitin Sulphate Proteoglycan in Vitro and Axonal Regeneration in the Adult Optic Nerve in Vivo," Journal of Neurochemistry, 2007, vol. 103 (1), pp. 181-189.
Little M., et al., "Of Mice and Men: Hybridoma and Recombinant Antibodies," Immunology Today, 2000, vol. 21 (8), pp. 364-370.
Logeart-Avramoglou D., et al., "An Assay for the Determination of Biologically Active Bone Morphogenetic Proteins Using Cells Transfected with an Inhibitor of Differentiation Promoter-luciferase Construct," Analytical Biochemistry, 2006, vol. 349 (1), pp. 78-86.
Lonberg N., et al., "Antigen-Specific Human Antibodies From Mice Comprising Four Distinct Genetic Modifications," Nature, 1994, vol. 368, pp. 856-859.
Lonberg N., et al., "Human Antibodies from Transgenic Mice," International Reviews of Immunology, 1995, vol. 13 (1), pp. 65-93.
Lories R.J., et al., "Bone Morphogenetic Protein Signaling in Joint Homeostasis and Disease," Cytokine and Growth Factor, 2005, vol. 16 (3), pp. 287-298.
Luciani N., et. al., "Hemojuvelin: A New Link Between Obesity and Iron Homeostasis," Obesity, 2011, vol. 19 (8), pp. 1545-1551.
Luckow V. A., et al., "High Level Expression of Nonfused Foreign Genes with Autographa Californica Nuclear Polyhedrosis Virus Expression Vectors," Virology, 1989, vol. 170 (1), pp. 31-39.

(56) References Cited

OTHER PUBLICATIONS

Lund J., et al., "Human Fc Gamma RI and Fc Gamma RII Interact with Distinct but Overlapping Sites on Human IgG," Journal of Immunology, 1991, vol. 147 (8), pp. 2657-2662.

Lunn M.P., et al., "High-Affinity Anti-Ganglioside IgG Antibodies Raised in Complex Ganglioside Knockout Mice: Reexamination of GDIa Immunolocalization," Journal of Neurochemistry, 2000, vol. 75 (1), pp. 404-412.

Ma C.H., et al., "The BMP Coreceptor RGMb Promotes While the Endogenous BMP Antagonist Noggin Reduces Neurite Outgrowth and Peripheral Nerve Regeneration by Modulating BMP Signaling," The Journal of Neuroscience, 2011, vol. 31 (50), pp. 18391-18400.

MacCallum R.M., et al., "Antibody-Antigen Interactions: Contact Analysis and Binding Site Topography," Journal of Molecular Biology, 1996, vol. 262 (5), pp. 732-745.

MacQuitty J.J., et al., "GenPharm's Knockout Mice," Science, 1992, vol. 257 (5074), pp. 1188.

Mann D.M., et al., "The Pattern of Acquisition of Plaques and Tangles in the Brains of Patients Under 50 Years of Age with Down's Syndrome.," Journal of the Neurological Sciences, 1989, vol. 89 (2-3), pp. 169-179.

Mann D.M, "The Neuropathology of Alzheimer's Disease: A Review with Pathogenetic, Aetiological and Therapeutic Considerations," Mechanisms of Ageing and Development, 1985, vol. 31 (3), pp. 213-255.

Marchalonis J.J., et al., "Evolutionary Factors in the Emergence of the Combinatorial Germline Antibody Repertoire," Advances in Experimental Medicine and Biology, 2001, vol. 484, pp. 13-30.

Marks J.D., et al., "By-Passing Immunization: Building High Affinity Human Antibodies by Chain Shuffling," Biotechnology, 1992, vol. 10 (7), pp. 779-783.

Martinez G., et al., "Expression of Bone Morphogenetic Protein-6 and Transforming Growth Factor-Beta1 in the Rat Brain after a Mild and Reversible Ischemic Damage," Brain Research, 2001, vol. 894 (1), pp. 1-11.

Matsuura I., et al., "BMP Inhibits Neurite Growth by a Mechanism Dependent on LIM-Kinase," Biochemical and Biophysical Research Communications, 2007, vol. 360 (4), pp. 868-873.

Mattingly P.G., "Chemiluminescent 10-Methyl-Acridinium-9(N-Sulphonylcarboxamide) Salts. Synthesis and Kinetics of Light Emission ," Journal of Bioluminescence and Chemiluminescence, 1991, vol. 6 (2), pp. 107-114.

Mattingly P.G., et al., In Instruments and Applications Luminescence: Instruments and Applications, Dyke K.V., Ed., CRC Press, 2002, pp. 77-105.

McCafferty J., et al., "Phage Antibodies: Filamentous Phage Displaying Antibody Variable Domains," Nature, 1990, vol. 348 (6301), pp. 552-554.

McCapra F., et al., "Chemiluminescence Involving Peroxide Decompositions ," Photochemistry and Photobiology, 1965, vol. 4 (6), pp. 1111-1121.

McNamara J.O., "Emerging Insights into the Genesis of Epilepsy.," Nature, 1999, vol. 399 (6738 Suppl.), pp. A15-A22.

Meier J., et al., "Extra Neruofilament NF-L Submits Rescue Motor Neuron Disease Caused by Overexpression of the Human NF-H Gene in Mice," Journal of Neuropathology and Experimental neurology, 1999, vol. 58 (10), pp. 1099-1110.

Mendez M.J., et al., "Functional Transplant of Megabase Human Immunoglobulin Loci Recapitulates Human Antibody Response in Mice," Nature Genetics, 1997, vol. 15 (2), pp. 146-156.

Merrfield R.B., et al., "Solid Phase Peptide Synthesis. I. The Synthesis of a Tetrapeptide," Journal of the American Chemical Society, 1963, vol. 85, pp. 2149-2154.

Mey J., et al., "Development of the Visual System of the Chick-A Review," Journal Fur Hirnforschung, 1992, vol. 33 (6), pp. 673-702.

Meyerhardt J.A., et al., "Identification and Characterization of Neogenin, a DCC-Related Gene," Oncogene, 1997, vol. 14 (10), pp. 1129-1136.

Milstein C., et al, "Hybrid Hybridomas and their use in Immunohistochemistry," Nature, 1983, vol. 305 (5934), pp. 537-540.

Mimms L.T., et al., "Discrimination of Hepatitis B Virus (HBV) Subtypes using Monoclonal Antibodies to the PreS1 and PreS2 Domains of the Viral Envelope," Virology, 1990, vol. 176 (2), pp. 604-619.

Ming G.L., et al., "cAMP-Dependent Growth Cone Guidance by Netrin-1," Neuron, 1997, vol. 19 (6), pp. 1225-1235.

Mirakaj et al., Supporting Information [online], Retrieved from the Internet< URL: http://www.pnas.org/cgi/content/short/1015605108>, 2011.

Mirakaj V., et al., "Repulsive Guidance Molecule-A (Rgm-A) Inhibits Leukocyte Migration and Mitigates Inflammation," Proceedings of the National Academy of Sciences, 2011, vol. 108 (16), pp. 6555-6560.

Mirakaj V., et al., "The Guidance Receptor Neogenin Promotes Pulmonary inflammation During Lung Injury," The FASEB Journal, 2012, vol. 26 (4), pp. 1549-1558.

Monahan M.W., et al., "A Rapid Method for the Preparation of Amino Acid Resin Esters for Merrifield Solid-phase Peptide Synthesis," Biopolymers, 1973, vol. 12 (11), pp. 2513-2519.

Monnier P.P., et al., "Rgm is a Repulsive Guidance Molecule for Retinal Axons," Nature, 2002, vol. 419 (6905), pp. 392-395.

Monschau B., et al., "Shared and Distinct Functions of RAGS and ELF-1 in Guiding Retinal Axons," EMBO Journal, 1997, vol. 16 (16), pp. 1258-1267.

Morgan R.A., et al., "Human Gene Therapy," Annual Review of Biochemistry , 1993, vol. 62, 191-217.

Mori H., et al., "Mass Spectrometry of Purified Amyloid Beta Protein in Alzheimer's Disease," The Journal of Biological Chemistry, 1992, vol. 267 (24), pp. 17082-17086.

Morrison S.L., "Transfectomas Provide Novel Chimeric Antibodies," Science, 1985, vol. 229 (4719), pp. 1202-1207.

Mueller B.K., et al., "The Role of Repulsive Guidance Molecules in the Embryonic and Adult Vertebrate Central Nervous System," Philosophical Transactions of the Royal Society, 2006, vol. 361 (1473), pp. 1513-1529.

Mueller B.K., "Growth Cone Guidance: First Steps Towards a Deeper Understanding," Annual Review of Neuroscience, 1999, vol. 22 , pp. 351-388.

Muhlhauser J., et al., "VEGF165 Expressed by a Replication-Deficient Recombinant Adenovirus vector induces Angiogenesis in Vivo," Circulation Research, 1995, vol. 77 (6), pp. 1077-1086.

Muller B.K., et al., "Molecular Inactivation. Spatially and Temporally Defined Molecular Knockouts," Current Biology, 1995, vol. 5 (11), pp. 1255-1256.

Muller B.K., et al., "Novel Gene Families Involved in Neural Pathfinding," Current Opinion in Genetics & Development, 1996, vol. 6 (4), pp. 469-474.

Mulligan R.C., "The Basic Science of Gene Therapy," Science, 1993, vol. 260 (5110), pp. 926-932.

Mullinax R.L., et al., "Expressoin of a Heterodimeric Fab Antibody Protein in One Cloning Step," Bio Techniques 1992, vol. 12 (6), pp. 864-869.

Muramatsu R, "Rgma Modulates T Cell Responses and is Involved in Autoimmune Encephalomyelitis," Nature Medicine, 2011, vol. 17 (4), pp. 488-494.

Murphy W.J., et al., "CD40 Stimulation Promotes Human Secondary Immunoglobulin Responses in HuPBL-SCID Chimeras," Clinical Immunology, 1999, vol. 90 (1), pp. 22-27.

Murphy W.J., et al., "The HuPBL-Scid Mouse as a Means to Examine Human Immune Function in Vivo," Seminars in Immunology, 1996, vol. 8 (4), pp. 233-241.

Nagata A., et al., "In Vivo Quantitative Evaluation of the Rat Retinal Nerve Fiber Layer with Pptical Coherence Tomography," Investigative Ophthalmology & Visual Science, 2009, vol. 50 (6), pp. 2809-2815.

Nakamoto M., et al., "Topographically Specific Effects of Elf-1 on Retinal Axon Guidance in Vitro and Retinal Axon Mapping in Vivo," Cell, 1996, vol. 86 (5), pp. 755-766.

Narang S.A., Tetrahedron, 1983, vol. 39 (1), pp. 3-22.

Nemeth E., et al., "Hepcidin, a Putative Mediator of Anemia of Inflammation, is a Type Ii Acute-Phase Protein," Blood, 2003, vol. 101 (7), pp. 2461-2463.

(56) References Cited

OTHER PUBLICATIONS

Neuberger M.S., et al., "Recombinant Antibodies Possessing Novel Effector Functions," Nature, 1984, vol. 312 (5995), pp. 604-608.
Nguyen H., et al., "Production of Human Monoclonal Antibodies in SCID Mouse," Microbiology and Immunology, 1997, vol. 41 (12), pp. 901-907.
Niederkofler V., et al., "Hemojuvelin is Essential for Dietary Iron Sensing, and its Mutation Leads to Severe Iron Overload," The Journal of Clinical Investigation, 2005, vol. 115 (8), pp. 2180-2186.
Niederkofler V., et al., "Repulsive Guidance Molecule (RGM) Gene Function is Required for Neural Tube Closure but not Retinal Topography in the Mouse Visual System," The Journal of Neuroscience : The Official Journal of the Society for Neuroscience, 2004, vol. 24 (4), pp. 808-818.
Nielsen P.E., et al., "Sequence-Selective Recognition of DNA by Strand Displacement with a Thymine-substituted Polyamide," Science, vol. 254 (5037), pp. 1497-1500, 1991.
Ning S., et al., "Intratumoral Radioimmunotherapy of a Human Colon Cancer Xenograft Using a Sustained-Release Gel," Radiotherapy & Oncology: The Journal of the European Society for Therapeutic Radiology and Oncology, 1996, vol. 39 (2), pp. 179-189.
Non-Final Office Action mailed Jan. 13, 2012 for U.S. Appl. No. 12/758,445, filed Apr. 12, 2010.
Notice of Allowance mailed Mar. 2, 2012 for U.S. Appl. No. 12/389,927 filed Feb. 20, 2009.
Notice of Allowance mailed Jun. 18, 2012 for U.S. Appl. No. 12/389,927, filed Feb. 20, 2009.
Office Action mailed Aug. 9, 2012 for Chinese Application No. 200880103451.
Office Action mailed Feb. 2, 2011 for European Application No. 08801915 filed Sep. 8, 2008.
Office Action mailed Feb. 7, 2011 for Canadian Application No. 2542171 filed Jun. 26, 2003.
Office Action mailed Mar. 7, 2012 for Japanese Application No. 2008532684 filed Sep. 29, 2006.
Office Action mailed Jan. 12, 2012 for Mexican Application No. MX2008020005 filed Sep. 29, 2006.
Office Action mailed Apr. 13, 2012 for Canadian Application No. 2542171 filed Jun. 26, 2003.
Office Action mailed Feb. 16, 2012 for Chinese Application No. 2006800363460. 1.
Office Action mailed Aug. 17, 2012 for Isreal Application No. 207787 filed Feb. 27, 2009.
Office Action mailed May 25, 2012 for Chinese Application No. 200880103451 filed Sep. 8, 2008.
Office Action mailed Feb. 28, 2012 for Japanese Application No. 2009250440 filed Oct. 30, 2009.
Office Examination Report mailed Mar. 11, 2011 for New Zealand Application No. 587198.
OI V.T., et al., "Chimeric Antibodies," BioTechniques, 1986, vol. 4 (3), pp. 214-221.
Opposition mailed Aug. 22, 2011 for Colombian Application No. 10117825 filed Sep. 23, 2010.
Opposition mailed Aug. 22, 2011 for Colombian Application No. 10117825, pp. 1-6.
Ota, T. et al., "Human protein encoded byfull length cDNA clone SEQ ID No. 3867,XP002476348,", 2004.
Padlan E.A., "A Possible Procedure for Recucing the Immunogenicity of Antibody Variable Domains While Preserving Their Ligand-Binding Properties," Molecular Immunology, 1991, vol. 28 (4-5), pp. 489-498.
Padlan E.A., et al., "Identification of Specificity-determining Residues in Antibodies," FASEB Journal, 1995, vol. 9 (1), pp. 133-139.
Padlan E.A., et al., "Structure of an Antibody-antigen Complex: Crystal Structure of the HyHEL-10 Fab-lysozyme Complex," Proceedings of the National Academy of Sciences, 1989, vol. 86 (15), pp. 5938-5942.
Papanikolaou G., et al., "Hepcidin in Iron Overload Disorders," Blood, 2005, vol. 105 (10), pp. 4103-4105.
Papanikolaou G., et al., "Mutations in Hfe2 Cause Iron Overload in Chromosome 1q-Linked Juvenile Hemochromatosis," Nature Genetics, 2004, vol. 36 (1), pp. 77-82.
Pauwels R., "Pharmacokinetics of Inhaled Drugs" in: Aerosols in Medicine: Principles, Diagnosis and Therapy, Moren F., et al., eds., Elsevier, 1985.
Pearson W.R., et al., "Improved Tools for Biological Sequence Comparison," Proceedings of the National Academy of Sciences, 1988, vol. 85 (8), pp. 2444-2448.
Persic L., et al., "An Integrated Vector System for the Eukaryotic Expression of Antibodies or their Fragments After Selection from Phage Display Libraries," Gene, 1997, vol. 187 (1), pp. 9-18.
Picker A., et al., "Requirement for the Zebrafish Mid-Hindbrain Boundary in Midbrain Polarisation, Mapping and Confinement of the Retinotectal Projection," Development, 1999, vol. 26 (13), pp. 2967-2978.
Pietrangelo A., "Hepcidin in Human Iron Disorders: Therapeutic Implications," Journal of Hepatology, 2011, vol. 54 (1), pp. 173-181.
Pietta P.G., et al., "Amide Protection and Amide Supports in Solid-phase Peptide Synthesis," Chemical Communications, 1970, pp. 650-651.
Polak J.M., et al., Introduction to Immunocytochemistry, 2nd Edition, Springer-Verlag, 1997, Table of Contents.
Poljak R.J., "Production and Structure of Diabodies," Structure, 1994, vol. 2 (12), pp. 1121-1123.
Postler E., et al., "Expression of the S-100 Proteins MRP-8 and -14 in Ischemic Brain Lesions," Glia, 1997, vol. 19 (1), pp. 27-34.
Powell K.T., et al., "Gel Microdroplets and Flow Cytometry Rapid Determination of Antibody Secretion by Individual Cells within a Cell Population," Biotechnology, 1990, vol. 8 (4), pp. 333-337.
Presta L.G., et al., "Humanization of an Antibody Directed Against IgE," Journal of Immunology, 1993, vol. 151 (5), pp. 2623-2632.
Puchtler H., et al., Journal of Histochemistry & Cytochemistry, 1962, vol. 10, pp. 365.
Puschel A.W., et al., "Murine Semaphorin D/collapsin is a Member of a Diverse Gene Family and Creates Domains Inhibitory for Axonal Extension," Neuron, 1995, vol. 14 (5), pp. 941-948.
Raper J.A., et al., "The Enrichment of a Neuronal Growth Cone Collapsing Activity from Embryonic Chick Brain," Neuron, vol. 4 (1), pp. 21-29, 1990.
Razavi Z., et al., "Stable and Versatile Active Acridinium Esters I ," Luminescence, 2000, vol. 15 (4), pp. 239-244.
Razavi Z., et al., "Stable and Versatile Active Acridinium Esters II ," Luminescence, 2000, vol. 15, pp. 245-249.
Reifers F., et al., "FGF8 is Mutated in Zebrafish Acerebellar (ACE) Mutants and is Required for Maintenance of Midbrain-Hindbrain Boundary Development and Somitogenesis," Development, 1998, vol. 125 (13), pp. 2381-2395.
Reisner Y., et al., "The Trimera Mouse: Generating Human Monoclonal Antibodies and an Animal Model for Human Diseases," Trends in Biotechnology, 1998, vol. 16 (6), pp. 242-246.
Remington, "The Science and Practice of Pharmacy," Table of Contents, 1995.
Resch E., et al., "Long Signal Peptides of RGMa and DCBLD2 are Dissectible into Subdomains According to the NtraC Model," Molecular BioSystems, 2011, vol. 7 (3), pp. 942-951.
Riechmann L., et al., "Reshaping Human Antibodies for Therapy," Nature, 1988, vol. 332 (6162), pp. 323-327.
Roberts R.W., et al., "RNA-peptide Fusions for the in Vitro Selection of Peptides and Proteins," Proceedings of the National Academy of Sciences, 1997, vol. 94 (23), pp. 12297-12302.
Robinson C., "Gene Therapy—Proceeding from Laboratory to Clinic," Tibtech, 1993, vol. 11 (5), pp. 155.
Robinson J.R., Sustained and Controlled Release Drug Delivery Systems, Marcel Dekker, Inc., 1978, Table of Contents.
Roes J., et al., "Mouse Anti-mouse IgD Monoclonal Antibodies Generated in IgD-deficient Mice," Journal of Immunological Methods, 1995, vol. 183 (2), pp. 231-237.
Roguska M.A., et al., "Humanization of Murine Monoclonal Antibodies through Variable Domain Resurfacing," Proceedings of the National Academy of Sciences, 1994, vol. 91 (3), pp. 969-973.

(56) References Cited

OTHER PUBLICATIONS

Rosen, C.A., Hadeltine, W.A., "Therapeuticprotein HARMJ38—SEQ ID No. 1853 Database EMBL/GENBANK/DDBJ Jun. 15, 2006, XP002468529,".

Routbort M.J., et al., "Seizures, Cell Death, and Mossy Fiber Sprouting in Kainic Acid Treated organotypic Hippocampal Cultures," Neuroscience, 1999, vol. 94 (3), pp. 755-765.

Rudikoff S., et al., "Single Amino Acid Substitution Altering Antigen-Binding Specificity," Proceedings of the National Academy of Sciences of the United States of America, 1982, vol. 79 (6), pp. 1979-1983.

Ruoslahti E., "RGD and Other Recognition Sequences for Integrins," Annual Review of Cell and Developmental Biology, 1996, vol. 12, pp. 697-715.

Saeed O., et al., "Pharmacological Suppression of Hepcidin Increases Macrophage Cholesterol Efflux and Reduces Foam Cell Formation and Atherosclerosis," Arteriosclerosis, Thrombosis, and Vascular Biology, 2012, vol. 32 (2), pp. 299-307.

Saltzman W.M., et al., "Transport Rates of Proteins in Porous Materials with Known Microgeometry," Biophysical Journal, 1989, vol. 55 (1), pp. 163-171.

Samad T.A., et al., "DRAGON, a Bonemorphogenetic Protein Co-Receptor," Journal of Biological Chemistry, 2005, vol. 280 (14), pp. 14122-14129.

Sambrook J., "Expression of Cloned Genes in *Escherichia coli*" in: Molecular Cloning, 2nd Edition, Cold Spring Harbor Laboratory Press, 1989, Chap. 17.2-17.9.

Samuels, ME., "Hemojuvelin variant(R326X),XP00247635,", 2004.

Sandhu J.S., et al., "The use of SCID Mice in Biotechnology and as a Model for Human Disease," Critical Reviews in Biotechnology, 1996, vol. 16 (1), pp. 95-118.

Santoro S.W., et al., "A General Purpose RNA-Cleaving Dna Enzyme," Proceedings of the National Academy of Sciences, 1997, vol. 94 (9), pp. 4262-4266.

Saudek C.D., et al., "A Preliminary Trial of the Programmable Implantable Medication System for Insulin Delivery," The New England Journal of Medicine, 1989, vol. 321 (9), pp. 574-579.

Sawai H., et al., "Direct Production of the Fab Fragment Derived from the Sperm Immobilizing Antibody using Polymerase Chain Reaction and Cdna Expression Vectors," American Journal of Reproductive Immunology, 1995, vol. 34 (1), pp. 26-34.

Schaffar G., et al., "Lim-only Protein 4 Interacts Directly with the Repulsive Guidance Molecule a Receptor Neogenin," Journal of Neurochemistry, 2008, vol. 107 (2), pp. 418-431.

Schaper W., et al., "Molecular Mechanisms of Coronary Collateral Vessel Growth," Circulation Research, 1996, vol. 79 (5), pp. 911-919.

Schaper W., et al., "Therapeutic Targets in Cardiovascular Disorders," Current Opinion in Biotechnology, 1996, vol. 7 (6), pp. 635-640.

Schier R., et al., "Identification of Functional and Structural Amino-Acid Residues by Parsimonious Mutagenesis," Gene, 1996, vol. 169 (2), 147-155.

Schmidtmer J., et al., "Isolation and Expression Pattern of Three Mouse Homologues of Chick Rgm," Gene Expression Patterns, 2004, vol. 4 (1), pp. 105-110.

Schnell L., et al., "Axonal Regeneration in the Rat Spinal Cord Produced by an Antibody Against Myelin-Associated Neurite Growth Inhibitors," Nature, 1990, vol. 343 (6255), pp. 269-272.

Schnichels S., et al., "Gene Expression of the Repulsive Guidance Molecules/Neogenin in the Developing and Mature Mouse Visual System: C57BL/6J vs. The Glaucoma Model DBA/2J," Gene Expression Patterns, 2007, vol. 8 (1), pp. 1-11.

Schnichels S., et al., "RGMA and Neogenin Protein Expression are Influenced by Lens Injury following Optic Nerve Crush in the Rat Retina," Graefe's Archive for Clinical and Experimental Ophthalmology, 2012, vol. 250 (1), pp. 39-50.

Schultz L.D., et al., "Expression and Secretion in Yeast of a 400-kDa Envelope Glycoprotein Derived from Epstein-Barr Virus," Gene, 1987, vol. 54 (1), pp. 113-123.

Schwab J.M., et al., "Central Nervous System Injury-Induced Repulsive Guidance Molecule Expression in the Adult Human Brain," Archives of Neurology, 2005, vol. 62 (10), pp. 1561-1568.

Schwab J.M., et al., "Selective Accumulation of Cyclooxygenase-1-Expressing Microglial Cells/Macrophages in Lesions of Human Focal Cerebral Ischemia," Acta Neuropathology, 2000, vol. 99 (6), pp. 609-614.

Schwab J.M., et al., "Spinal Cord Injury-Induced Lesional Expression of the Repulsive Guidance Molecule (RGM)," The European Journal of Neuroscience, 2005, vol. 21 (6), pp. 1569-1576.

Seed B., "An LFA-3 cDNA Encodes a Phospholipid-Linked Membrane Protein Homologous to its Receptor CD2," Nature, 1997, vol. 329 (6142), pp. 840-842.

Sefton M.V., et al., "Implantable Pumps," Critical Reviews in Biomedical Engineering, 1987, vol. 14 (3), pp. 201-240.

Serafini T., et al., "Netrin-1 Is Required for Commissural Axon Guidance in the Developing Vertebrate Nervous System," Cell, 1996, vol. 87 (6), pp. 1001-1014.

Setoguchi T., et al., "Treatment of Spinal Cord Injury by Transplantation of Fetal Neural Precursor Cells Engineered to Express BMP Inhibitor," Experimental Neurology, 2004, vol. 189 (1), pp. 33-44.

Severyn C.J., et al., "Molecular Biology, Genetics and Biochemistry of the Repulsive Guidance Molecule Family," Biochemical Journal, 2009, vol. 422 (3), pp. 393-403.

Shapiro G.S., et al., "DNA Target Motifs of Somatic Mutagenesis in Antibody Genes," Critical Reviews in Immunology, 2002, vol. 22 (3), pp. 183-200.

Sharp P.A., "RNAi and Double-Strand RNA," Genes & Development, 1999, vol. 13 (2), pp. 139-141.

Sherwood J.K., et al., "Controlled Antibody Delivery Systems," Biotechnology, 1992, vol. 10 (11), pp. 1446-1449.

Shields R.L., et al., "Lack of Fucose on Human IgG1 N-Linked Oligosaccharide Improves Binding to Human Fcgamma RIII and Antibody-Dependent Cellular Toxicity," The Journal of Biological Chemistry, 2002, vol. 277 (30), pp. 26733-26740.

Shoemaker L.D., et al., "Identification of Differentially Expressed Proteins in Murine Embryonic and Postnatal Cortical Neural Progenitors," PLoS One, 2010, vol. 5 (2), pp. e9121.

Shu L., et al., "Secretion of a Single-Gene-Encoded Immunoglobulin from Myeloma Cells," Proceedings of the National Academy of Sciences, 1993, vol. 90 (17), pp. 7995-7999.

Silhavy., et al., Experiments with Gene Fusions, Cold Spring Harbor Laboratory, 1984.

Sims M.J., et al., "A Humanized CD18 Antibody can Block Function without Cell Destruction," Journal of Immunology, 1993, vol. 151 (4), pp. 2296-2308.

Skerra A., et al., "Assembly of a Functional Immunoglobulin Fv Fragment in *Escherichia coli*," Science, 1988, vol. 240 (4855), pp. 1038-1041.

Smith D.B., et al., "Single-Step Purification of Polypeptides Expressed in *Escherichia coli* as Fusions with Glutathione S-Transferase," Gene, 1988, vol. 67 (1), pp. 31-40.

Smith G. E., et al., "Production of human beta interferon in insect cells infected with a baculovirus expression vector", Mol Cell Biol., 1983, 3 (12), 2156-2165.

Smith T.F., et al., "The Challenges of Genome Sequence Annotation or "The Devil Is in the Details"," Nature Biotechnology, 1997, vol. 15 (12), pp. 1222-1223.

Smithson S.L., et al., "Molecular Analysis of the Heavy Chain of Antibodies that Recognize the Capsular Polysaccharide of Neisseria Meningitidis in hu-PBMC Reconstituted SCID Mice and in the Immunized Human Donor," Molecular Immunology, 1999, vol. 36 (2), pp. 113-124.

Smolen V.F., et al., eds., Controlled Drug Bioavailability: Drug Product Design and Performance, vol. 1, John Wiley & Sons, 1984, Table of Contents.

Song Y.K., et al., "Antibody Mediated Lung Targeting of Long-Circulating Emulsions," PDA Journal of Pharmaceutical Science & Technology, 1995, vol. 50 (6), pp. 372-377.

Sperry R.W., "Chemoaffinity in the orderly Growth of Nerve Fiber Patterns and Connections," Proceedings of the National Academy of Sciences, 1963, vol. 50, pp. 703-710.

(56) References Cited

OTHER PUBLICATIONS

Staerz U.D., et al., "Hybrid Antibodies Can Target Sites for Attack by T Cells," Nature, 1985, vol. 314 (6012), pp. 628-631.

Stahl B., et al., "Biochemical Characterization of a Putative Axonal Guidance Molecule of the Chick Visual System," Neuron, 1990, vol. 5 (5), pp. 735-743.

Steenbakkers P.G., et al., "Efficient Generation of Monoclonal Antibodies from Preselected Antigen-Specific B Cells. Efficient Immortalization of Preselected B Cells," Molecular Biology Reports, 1994, vol. 19 (2), pp. 125-134.

Steinecke P., et al., "Ribozymes," Methods in Cell Biology, 1995, vol. 50, pp. 449-460.

Stewart J.M., et al., Solid-Phase Peptide Synthesis, 2nd Edition, Pierce Chemical Company, 1984, Table of Contents.

Stoll G., et al., "Inflammation and Glial Responses in Ischemic Brain Lesions," Progress in Neurobiology, 1998, vol. 56 (2), pp. 149-171.

Streit W.J., et al., "Reactive Microgliosis," Progress in Neurobiology, 1999, vol. 57 (6), pp. 563-581.

Studier F.W., et al., "Use of T7 RNA Polymerase to Direct Expression of Cloned Genes," Methods in Enzymology, 1990, vol. 185, pp. 60-89.

Studnicka G.M., et al., "Human-Engineered Monoclonal Antibodies Retain Full Specific Binding Activity by Preserving Non-CDR Complementarity-Modulating Residues," Protein Engineering, 1994, vol. 7 (6), pp. 805-814.

Suda M., et al., "Peptides Derived from Repulsive Guidance Molecule Act As Antagonists," Biochemical and Biophysical Research Communications, 2008, vol. 371 (3), pp. 501-504.

Supplementary International Search Report for Application No. PCT/EP2009/001437, mailed on Apr. 8, 2010, 2 pages.

Sutcliffe J.G., et al., "Antibodies that React with Predetermined Sites on Proteins," Science, 1983, vol. 219 (4585), pp. 660-666.

Takeda S., et al., "Construction of Chimaeric Processed Immunoglobulin Genes Containing Mouse Variable and Human Constant Region Sequences," Nature, 1985, vol. 314 (6010), pp. 452-454.

Tanelian D.L., et al., "Semaphorin III Can Repulse and Inhibit Adult Sensory Afferents in Vivo," Nature Medicine, 1997, vol. 3 (12), pp. 1398-1401.

Tassew N.G., et al., "Intraretinal RGMa is Involved in Retino-Tectal Mapping," Molecular and Cellular Neuroscience, 2008, vol. 37 (4), pp. 761-769.

Taylor L.D., et al., "A Transgenic Mouse that Expresses a Diversity of Human Sequence Heavy and Light Chain Immunoglobulins," Nucleic Acids Research, 1992, vol. 20 (23), pp. 6287-6295.

Terry R.D., et al., "Senile Dementia of the Alzheimer Type Without Neocortical Neurofibrillary Tangles," Journal of Neuropathology & Experimental Neurology, 1987, vol. 46 (3), pp. 262-268.

Tessier-Lavigne M., et al., "The Molecular Biology of Axon Guidance," Science, 1996, vol. 274 (5290), pp. 1123-1133.

Tolstoshev P., "Gene Therapy, Concepts, Current Trials and Future Directions," Annual Review of Pharmacology and Toxicology, 1993, vol. 32, pp. 573-596.

Umana P., et al., "Engineered Glycoforms of an Antineuroblastoma IgG1 with Optimized Antibody-dependent Cellular Cytotoxic Activity," Nature Biotechnology, 1999, vol. 17 (2), pp. 176-180.

Uniport, "A1L187_HUMAN", Accession No. A1L187, Feb. 6, 2007.

Urist M.R., et al., "Osteoporosis: A Bone Morphogenetic Protein Auto-Immune Disorder," Progress in Clinical and Biological Research, 1985, vol. 187, pp. 77-96.

Urlaub G., et al., "Isolation of Chinese Hamster Cell Mutants Deficient in Dihydrofolate Reductase Activity," Proceedings of the National Academy of Sciences, 1980, vol. 77 (7), pp. 4216-4220.

Vajdos F.F., et al., "Comprehensive Functional Maps of the Antigen-binding Site of an AntiErbB2 Antibody Obtained with Shotgun Scanning Mutagenesis," Journal of Molecular Biology, 2002, vol. 320 (2), pp. 415-428.

Van Den Hondel., "Gene Transfer Systems and Vector Development for Filamentous Fungi" in: Applied Molecular Genetics of Fungi, J.F. Peberdy et al., eds., C.A.M.J.J. & Punt, P.J., 1991, pp. 1-28.

Verhoeyen M., et al., "Reshaping Human Antibodies: Grafting an Antilysozyme Activity ," Science, 1988, vol. 239, pp. 1534-1536.

Verma I.M., et al., "Gene Therapy -- Promises, Problems and Prospects," Nature, 1997, vol. 389 (6648), pp. 239-242.

Vielmetter J., et al., "In Vitro Assay to Test Differential Substrate Affinities of Growing Axons and Migratory Cells," Experimental Brain Research, 1990, vol. 81 (2), pp. 283-287.

Vielmetter J., et al., "Neogenin, an Avian Cell Surface Protein Expressed During Terminal Neuronal Differentiation, Is Closely Related to the human Tumor Suppressor Molecule Deleted in Colorectal Cancer," the Journal of Cell Biology, 1994, vol. 127 (6 Pt 2), pp. 2009-2020. ill.

Viewing Sequence(s): 1853 of 2267 for Document # 20060084794, Publication Site for Issued and Published Sequences (Psips), Seq Id no. 1853 [online], Jan. 2011 [Last Modified on 2011-01-25]. Retrieved from the Internet< Url: http://segdata.uspto.gov/?pagerequest=view.

Voet D., et al., Biochemistry, Second Edition, John Wiley & Sons, Inc, 1995, Table of Contents.

Wahl J., et al., "Ephrin-A5 Induces Collapse of Growth Cones by Activating Rho and Rho Kinase," Journal of Cell Biology, 2000, vol. 149 (2), pp. 263-270.

Wallemacq P.E., et al., "Evaluation of the New AxSYM Cyclosporine Assay: Comparison with TDx Monoclonal Whole Blood and Emit Cyclosporine Assays," Clinical Chemistry, 1999, vol. 45 (3), pp. 432-435.

Wallick S.C., et al., "Glycosylation of a VH Residue of a Monoclonal Antibody against Alpha (1-6) Dextran Increases its Affinity for Antigen," Journal of Experimental Medicine, 1988, vol. 168 (3), pp. 1099-1109.

Walter J., et al., "Avoidance of Posterior Tectal Membranes by Temporal Retinal Axons," Development, 1987, vol. 101 (4), pp. 909-913.

Walter J., et al., "Axonal Guidance by an Avoidance Mechanism," Journal de Physiologie, 1990, vol. 84 (1), pp. 104-110.

Walter J., et al., "Recognition of Position-Specific Properties of Tectal Cell Membranes by Retinal Axons in Vitro," Development, 1987, vol. 101 (4), pp. 685-696.

Wang H., et al., "Netrin-3, A Mouse Homolog of Human NTN2L, is Highly Expressed in Sensory Ganglia and Shows Differential Binding to Netrin Receptors," The Journal of Neuroscience, 1999, vol. 19 (12), pp. 4938-4947.

Wang Q., et al., "Second-Generation Adenovirus Vectors," Nature Medicine, 1996, vol. 2 (6), pp. 714-716.

Ward E.S., et al., "Binding Activities of a Repertoire of Single Immunoglobulin Variable Domains Secreted from *Escherichia coli*," Nature, 1989, vol. 341 (6242), pp. 544-546.

Weinstein D.A., et al., "Inappropriate Expression of Hepcidin is Associated with Iron Refractory Anemia: Implications for the Anemia of Chronic Disease," Blood, 2002, vol. 100 (10), pp. 3776-3778.

Weiss G., et al., "Anemia of Chronic Disease," The New England Journal of Medicine, 2005, vol. 352 (10), pp. 1011-1023.

Wells D.A., et al., "High Throughput Bioanalytical Sample Preparation Methods and Automation Strategies," Progress in Pharmaceutical and Biomedical Analysis, 2003, Table of Contents.

Wells J.A., "Additivity of Mutational Effects in Proteins," Biochemistry, 1990, vol. 29 (37), pp. 8509-8517.

Wen L., et al., "Limiting Dilution Assay for Human B Cells Based on their Activation by Mutant EL4 Thymoma Cells: Total and Antimalaria Responder B Cell Frequencies," European Journal of Immunology, 1987, vol. 17 (6), pp. 887-892.

Wilbur W.J., et al., "Rapid Similarity Searches of Nucleic Acid and Protein Data Banks," Proceedings of the National Academy of Sciences , 1983, vol. 80 (3), pp. 726-730.

Wilm M., et al., "Analytical Properties of the Nanoelectrospray Ion Source," Analytical Chemistry, 1996, vol. 68 (1), pp. 1-8.

Wilm M., et al., "Femtomole Sequencing of Proteins from Polyacrylamide Gels by Nano-Electrospray Mass Spectrometry," Nature, 1996, vol. 379 (6564), pp. 466-469.

Winnaker E.L., From Genes to Clones: Introduction to Gene Technology, VCH Publishers, 1987, Table of Contents.

(56) References Cited

OTHER PUBLICATIONS

Wisniewski H.M., et al., "Reexamination of the Pathogenesis of the Senile Plaque", in: Progress in Neuropathology, Grupe and Stratton, N.Y, Zimmerman H.M., ed., vol. 2, 1973, pp. 1-26.
Wright A., et al., "Antibody Variable Region Glycosylation: Position Effects on Antigen Binding and Carbohydrate Structure," The EMBO Journal, 1991, vol. 10 (10), pp. 2717-2723.
Written Opinion for Application No. PCT/EP2009/001437, mailed on Jun. 18, 2009, 7 pages.
Written Opinion for Hungarian Application No. 201005799-0, mailed on Jun. 8, 2012.
Wu C., et al., "Simultaneous Targeting of Multiple Disease Mediators by a Dual-Variable Domain Immunoglobulin," Nature Biotechnology, 2007, vol. 25 (11), pp. 1290-1297.
Wu G., et al., "Delivery Systems for Gene Therapy," Biotherapy, 1991, vol. 3 (1), pp. 87-95.
Wu G.Y., et al., "Receptor-mediated in Vitro Gene Transformation by a Soluble DNA Carrier System," Journal of Biological Chemistry, 1987, vol. 262 (10), pp. 4429-4432.
Wu H., et al., "Humanization of a Murine Monoclonal Antibody by Simultaneous Optimization of Framework and CDR Residues," Journal of Molecular Biology, 1999, vol. 294 (1), pp. 151-162.
Xia Y., et al., "Dragon (Repulsive Guidance Molecule B) Inhibits IL-6 Expression in Macrophages," Journal of Immunology, 2011, vol. 186 (3), pp. 1369-1376.
Xia Y., et al., "Localization and Action of Dragon (repulsive guidance molecule b), a Novel Bone Morphogenetic Protein Coreceptor, throughout the Reproductive Axis," Endocrinology, 2005, vol. 146 (8), pp. 3614-3621.
Xia Y., et al., "Repulsive Guidance Molecule RGMa Alters Utilization of Bone Morphogenetic Protein (BMP) Type II Receptors by BMP2 and BMP4," Journal of Biological Chemistry, 2007, vol. 282 (25), pp. 18129-18140.
Yamashita T., et al., "Neogenin and Repulsive Guidance Molecule Signaling in the Central Nervous System," Current Opinion in Neurobiology, 2007, vol. 17 (1), pp. 29-34.
Yamashita T., RGMa Modulates T Cell Responses and is Involved in Autoimmune Encephalomyelitis, Supplementary Information Titles, Nature Medicine, 2011.
Yang X.D., et al., "Fully Human Anti-Interleukin-8 Monoclonal Antibodies: Potential Therapeutics for the Treatment of Inflammatory Disease States," Journal of Leukocyte Biology, 1999, vol. 66 (3), pp. 401-410.
Yatscoff R.W., et al., "Abbott TDx Monoclonal Antibody Assay Evaluated for Measuring Cyclosporine in Whole Blood," Clinical Chemistry, 1990, vol. 36 (11), pp. 1969-1973.
Yeh M.Y., et al., "A Cell-surface Antigen Which is Present in the Ganglioside Fraction and Shared by Human Melanomas," International Journal of Cancer, 1982, vol. 29 (3), pp. 269-275.
Yeh M.Y., et al., "Cell Surface Antigens of Human Melanoma Identified by Monoclonal Antibody," Proceedings of the National Academy of Sciences, 1979, vol. 76 (6), pp. 2927-2931.
Yelton D.E., et al., "Affinity Maturation of the BR96 Anti-Carcinoma Antibody by Codon-Based Mutagenesis," the Journal of Immunology, 1995, vol. 155 (4), pp. 1994-2004.
Yoshinari K., et al., "Differential Effects of Immunosuppressants and Antibiotics on Human Monoclonal Antibody Production is Scid Mouse Ascites by Five Heterohybridomas," Hybridoma, 1998, vol. 17 (1), pp. 41-45.
Yu T.W., et al., "Dynamic Regulation of Axon Guidance," Nature Neuroscience, 2001, Suppl. 4, pp. 1169-1176.
Zapata G., et al., "Engineering Linear F(ab')2 Fragments for Efficient Production in *Escherichia coli* and Enhanced Antiproliferative Activity," Protein Engineering, 1995, vol. 8 (10), pp. 1057-1062.
Zhang G., et al., "Electrical Stimulation of Olfactory Bulb Downregulates RGMa Expression After Ischemia/Reperfusion Injury in Rats," Brain Research Bulletin, 2011, vol. 86 (3-4), pp. 254-261.
Final Office Action mailed Mar. 12, 2014 for U.S. Appl. No. 12/963,461, filed Dec. 8, 2010.
Hermanson G.T., "Antibody Modification and Conjugation," in: Bioconjugate Techniques, 1996, Chapter 10, Academic Press, pp. 456-493.
Singer M., et al. Genes and Genomes, A Changing Perspective, University science Books, California, 1991, pp. 68-69.

\* cited by examiner

CLUSTAL W (1.82) multiple sequence alignment

```
RGMA        -MQPPRERLVVTG---------------------RAGWMGMGRGAG-------------  24
RGMB        MIRKKRKRSAPPGPCRSHGPRPATAPAPPPSPEPTRPAWTGMGLRAAPSSAAAAAAEVEQ  60
RGMC        -MGEPGQSPSPRS----------------------SHGS--------------------  16
                :              .              .         *

RGMA        RSALGFWPT----LAFLLCSFPAATS-------FCKILKCNSEFWSATSGSHAPASD---  70
RGMB        RRRPGLCPPPLELLLLLLLFSLGLLHAGDCQQPAQCRIQKCTTDFVSLTSHLNSAVDG---  117
RGMC        -------PPTLSTLTLLLLLCGHAHS-------QCKILRCNAEYVSSTLSLRGGGSSGAL  62
                   *.    *  :**       :       *:*  :*.::;  *  *      ..

RGMA        -------------DTPEFCAALRSYALCTRRTARTCRGDLAYHSAVHGIEDLMSQHNCSKD  118
RGMB        -------------FDSEFCKALRAYAGCTQRTSKACRGNLVYHSAVLGISDLMSQRNCSKD  165
RGMC        RGGGGGGGRGGGVGSGGLCRALRSYALCTRRTARTCRGDLAFHSAVHGIEDLMIQHNCSRQ  122
                         :*  ***:** **:**::**:*: .:**** **.***  *:***::

RGMA        GPTSQPRLRTLPPAGDSQERSDSPEICHYEKSFHKHSATPNYTHCGLFGDPHLRTFTDRF  178
RGMB        GPTSSTNPEVTHDPCNYHSHAGAREHRRGDQ------NPPSYLFCGLFGDPHLRTFKDNF  219
RGMC        GPTAPPPPRGPALPGAGSGLPAPDPCDYEGRFSRLHGRPPGFLHCASFGDPHVRSFHHHF  182
            ***:  .      .  .          :           .*:  .*. *****:*:*  .*

RGMA        QTCKVQGAWPLIDNNYLNVQATNTPVLPGSAATATSKLTIIFKNFQECVDQKVYQAEMDE  238
RGMB        QTCKVEGAWPLIDNNYLSVQVTNVPVVPGSSATATNKITIIFKAHHECTDQKVYQAVTDD  279
RGMC        HTCRVQGAWPLLDNDFLFVQATSSPMALGANATATRKLTIIFKNMQECIDQKVYQAEVDN  242
            :**:*:*.:******:**::* **.*. *:  *;  ****  ;*****;  *:

RGMA        LPAAFVDGSKNGGDKHGANSLKITEKVSGQHVEIQAKYIGTTIVVRQVGRYLTFAVRMPE  298
RGMB        LPAAFVDGTTSGGDSD-AKSLRIVERESGHYVEMHARYIGTTVFVRQVGRYLTLAIRMPE  338
RGMC        LPVAFEDGSINGGDRPGGSSLSIQTANPGNHVEIQAAYIGTTIIIRQTAGQLSFSIKVAE  302
            **.** **; .***    ..** *  .*::*::**;:* *****;..:**..   *:::::*

RGMA        EVVNAVEDWDSQGLYLCLRGCPLNQQIDFQAFHTNAEGTGARRLAAASPAPTAPETFP--  356
RGMB        DLAMSYE--ESQDLQLCVNGCPLSERID------DGQGQVSAILGHSLPRTSLVQAWPGY  390
RGMC        DVAMAFS--AEQDLQLCVGGCPPSQRLS-------RSERNRRGAIT------------  339
            ::. :    .*.*  **  **;  ***   .:::.

RGMA        -YETAVAKCKEKLPVEDLYYQACVFDLLTTGDVNFTLAAYYALEDVKMLHSNKDKLHLYE  415
RGMB        TLETANTQCHEKMPVKDIYFQSCVFDLLTTGDANFTAAAHSALEDVEALHPRKERWHIFP  450
RGMC        -IDTARRLCKEGLPVEDAYFHSCVFDVLISGDPNFTVAAQAALEDARAFLPDLEKLHLFP  398
             :**   *:*:* *:;::****:* :** *** ** ****..  :   ::  *::

RGMA        RTRDLPGRAAAGLPLAPRPLLGALVPLLALLPVFC  450
RGMB        SSGNGTPRGGSDLSVSLG--LTCLILIVFL-----  478
RGMC        SDAGVPLSSATLLAPLLS---GLFVLWLCIQ----  426
               . ..: *.       ::   : :
```

Fig. 1

| N | | | | | | | C |
|---|---|---|---|---|---|---|---|
| Signal peptide | R G D | vWFD | | | Hydro-phobic region | | GPI anchor |

PBS control
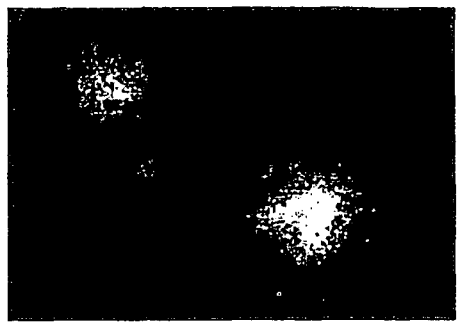
Buffer control
Pep. 4
Pep. 1
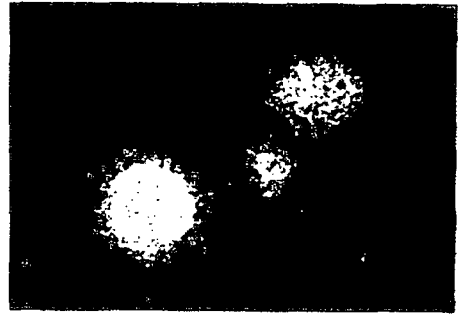
Fig. 3A + peptide 1 (30µg/ml)
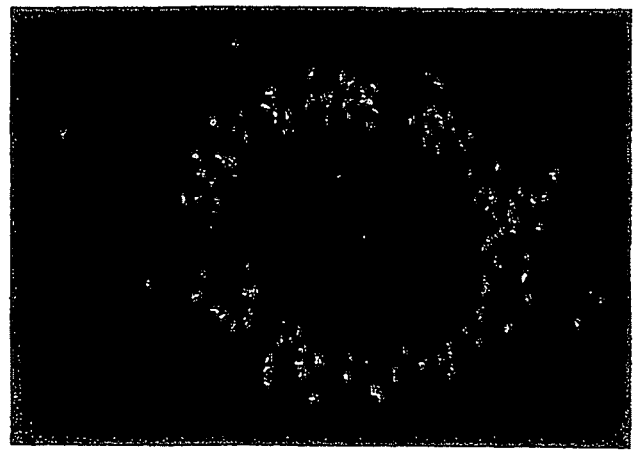
+ peptide 4 (30µg/ml)
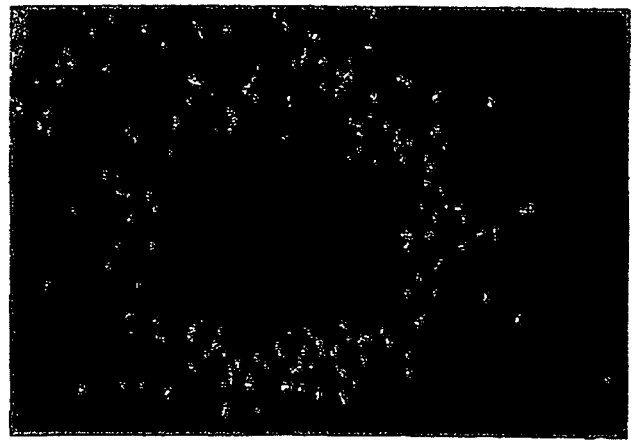
+ PBS (control)
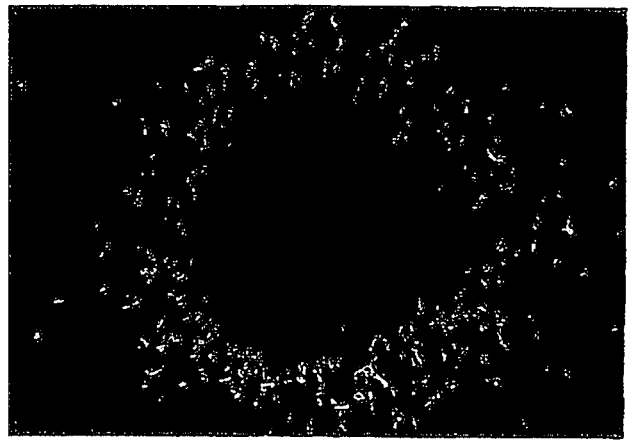
Fig. 4A

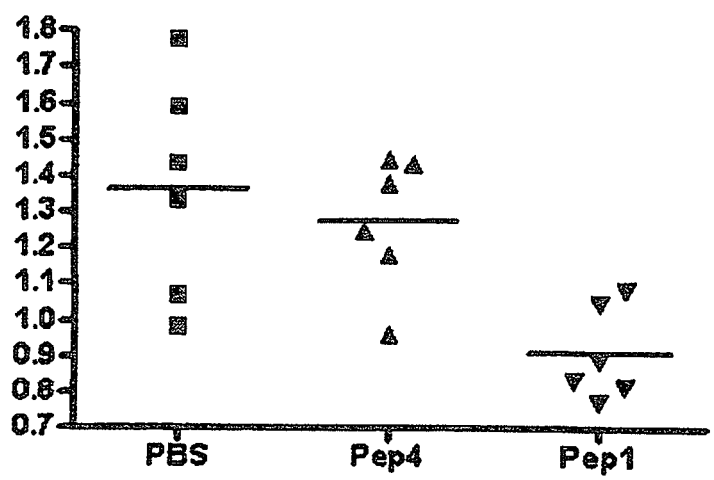
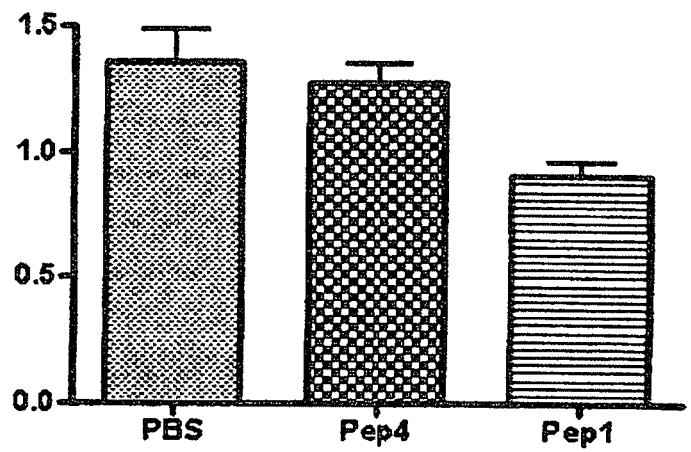
Pep 1 vs PBS:  $p < 0.01$
Pep 1 vs Pep4: $p < 0.05$
Pep 4 vs PBS:  $p > 0.05$
Fig. 4B

*** = p < 0.001 significance versus PBS control

BINDING DOMAINS OF PROTEINS OF THE REPULSIVE GUIDANCE MOLECULE (RGM) PROTEIN FAMILY AND FUNCTIONAL FRAGMENTS THEREOF, AND THEIR USE

CROSS-REFERENCE TO RELATED APPLICATIONS

This is a U.S. national stage entry of International Patent Application No. PCT/EP2006/009497, filed on Sep. 29, 2006, which claims priority to U.S. patent application No. 60/722,565, filed on Oct. 1, 2005, and European Patent Application No. 05021451.9, filed on Sep. 30, 2005, the entire contents of all of which are fully incorporated herein by reference.

The present invention relates to the identification and use of the receptor-binding domain of members of the repulsive guidance molecule (RGM) protein family, and to polypeptide fragments derived therefrom. The domains and peptide fragments according to the invention are suitable as agents for active or passive immunization of individuals and as diagnostic and therapeutic agents for use for diseases or pathological conditions in whose development or progression a member of the RGM family and a cellular receptor assigned to this molecule is involved. The invention additionally relates to monoclonal and polyclonal antibodies against the binding domains according to the invention and against the polypeptides derived therefrom, and to methods for preparing the domains, polypeptides and antibodies according to the invention.

PRIOR ART

The function of the members of the RGM protein family was described for the first time by Monnier, P. P. et al., Nature, 419, pp. 392-395, 2002. This family includes three members disclosed to date, which are referred to as RGM A, RGM B (also referred to as DRAGON) and RGM C (also referred to as hemojuvelin) (Niederkofler V. et al., J. Neurosci. 24, 808-18, 2004). These are glycoproteins which are bound to the plasma membrane via a lipid anchor (glycosylphosphatidylinositol anchor=GPI anchor). The members of this protein family do not have any extensive sequence homology to other proteins, and structural features which have been identified are substantially the following regions: an N-terminal signal peptide; an RGD sequence; a proteolytic cleavage site around the amino acid sequence GDPH; a structural homolog of von Willebrand factor domain (vWF D); a hydrophobic sequence in the vicinity of the C terminus and a C-terminal GPI anchor consensus sequence (cf. also FIG. 2).

In humans, the coding sequences for RGM A are located on chromosome 15, for RGM B on chromosome 5 and for RGM C on chromosome 1. A characteristic expression pattern is to be observed. RGM A and B are expressed in particular in adult brain and spinal cord, RGM C is expressed in particular in skeletal muscle, liver and myocardium, and RGM B is additionally expressed in cartilage tissue.

RGM proteins were originally identified as candidate proteins playing an important part in the formation of topographic neuronal projections (Stahl B. et al., Neuron 5:p 735-43, 1990; Mueller B. K. et al., Curr. Biol. 6, pp. 1497-1502, 1996; Mueller B. K in Molecular Basis of Axon Growth and Nerve Pattern Formation, Edited by H. Fujisawa, Japan Scientific Societies Press, 215-229, 1997). Their ability to act in a repulsive or inhibitory manner on growing nerve fibers was a decisive functional feature which played an important part in their isolation, cloning and characterization. The activity was readily detectable in simple cellular assay systems. RGM proteins have an inhibitory or repulsive effect in two different cellular assays. In the collapse assay, RGM proteins are added to growing nerve fibers. The binding of RGM to the RGM receptor induces a vigorous response involving all the membranous elements of the neuronal growth cone. The original extended hand-like growth cone is converted thereby into a thin thread. In the presence of RGM, the nerve fibers remain inhibited, retract greatly and are no longer able to continue their growth.

RGM proteins exert part of their effect by binding to the RGM receptor neogenin (Rajagopalan S. et al., Nat Cell Biol. 6, pp. 756-62, 2004). Neogenin is closely related to the DCC receptor (deleted in colorectal cancer). Both receptors are members of the immunoglobulin superfamily and have an extracellular, a transmembrane and an intracellular domain. Both have been described as receptors for a further ligand, netrin-1, but only neogenin, not DCC, binds RGM proteins. The extracellular domains of these receptors consist of 4 immunoglobulin-like domains followed by 6 fibronectin repeat domains.

The function of RGM A in the nervous system is understood best, and it is particularly noteworthy for its effect of inhibiting at very low concentrations the growth of nerve fibers. Injury to the central nervous system in adult humans and in adult rats leads to an accumulation of RGM proteins at the site of the lesion (Schwab J. M. et al., Arch. Neurol. in press, 2005; Schwab J. M. et al., Eur. J. Neurosci. 21:p. 387-98, 2005). Renewed outgrowth of the injured nerve fibers is prevented thereby, and permanent, more or less severe functional deficits occur, depending on the location of the site of the lesion. This inhibitory activity of RGM for nerve fiber growth is mediated by binding to the neogenin receptor (Rajagopalan S. et al., loc. cit.). However, the same receptor mediates, via binding of netrin-1, also a contrary effect stimulating nerve fiber growth.

Very recent results indicate that RGM proteins also fulfill important tasks in the central and peripheral nervous system, in regulating iron metabolism, in neoplastic diseases, in inflammatory processes and in the formation of bone and cartilage tissue.

Based on the observation that RGM A, B and C bind with high affinity to the neogenin receptor, the object of the present invention was to characterize in detail the functional binding domain of these molecules, especially of RGM A. This would make it possible to generate antibodies against the domain and against active RGM peptides which are derived therefrom and which with high probability neutralize the inhibitory activity of RGM and which might thereby stimulate the regeneration or renewed outgrowth of nerve fibers. In addition, binding domains or active RGM peptides derived therefrom could be provided per se as therapeutic effective agents.

BRIEF DESCRIPTION OF THE INVENTION

The above object has surprisingly been achieved by isolating and characterizing the binding domain of human RGM proteins, especially RGM A, and active polypeptide fragments thereof.

DESCRIPTION OF THE FIGURES

FIG. 1 shows the sequence alignment of the human forms of RGM A (GenBank #NP_064596.1) RGM B (GenBank #NP_001012779) and RGM C (GenBank #NP_998818.1).

FIG. 2 shows in diagrammatic representation the structure of RGM molecules. Between the N-terminal signal peptide and the C-terminal GPI anchor there are shown the RGD sequence, the von Willebrand factor domain (vWF D) and a hydrophobic sequence in the region of the C terminus in front of the anchor region. The binding domain region of interest according to the invention is presumed to be between vWFD and hydrophobic region. Below the diagram are the corresponding amino acid positions for human RGM A, the proteolytic cleavage site between amino acids 168 and 169.

FIG. 4A depicts fluorescence micrographs of human neuronal NTera cells which illustrate the influence of RGM A peptide 1 and peptide 4 (each in a concentration of 30 µg/ml) on nerve fiber growth of these cells. As comparison with the likewise depicted control image (incubation with PBS instead of peptide) shows, only peptide 1 has an inhibitory effect on nerve fiber growth. FIG. 4B depicts the correspondingly measured axon growth indices for test series with peptide 1, peptide 4 and control (PBS) (upper diagram: individual measurements and mean, lower diagram: bar diagram with mean and standard deviation).

DETAILED DESCRIPTION OF THE INVENTION

I. Explanations of General Terms

Figure 3B:
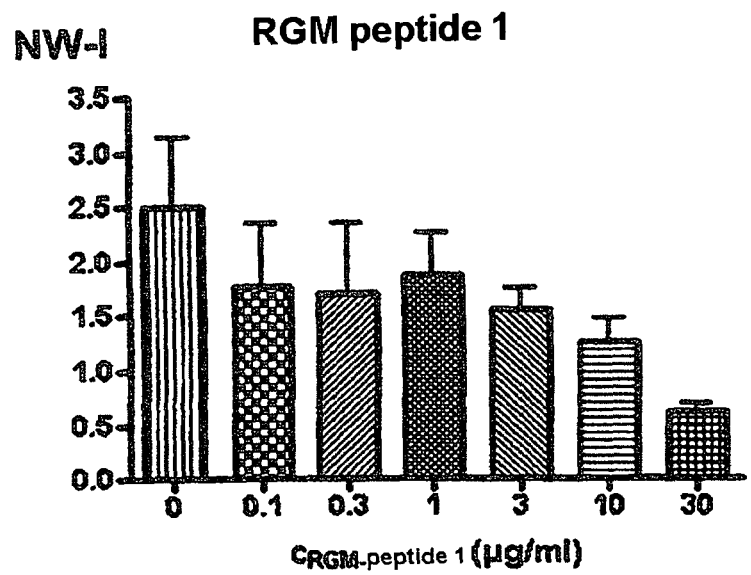
FIG. 3B shows a bar diagram of measured axon growth indices (a measure of the area covered by axons in relation to the cell aggregate size; mean and standard deviation is shown) to illustrate the concentration-dependence of the axon growth-inhibitory activity of the RGM A peptide 1 of the invention. The corresponding bar diagram for the RGM A peptide 4 is shown in FIG. 3C.

"Receptors" designate in the context of the present invention in particular surface molecules which are bound to a cell membrane and which are able to interact with a, for example soluble, ligand and, as a consequence of this interaction, may induce a signal which is directed for example into the interior of the cell, or a signal cascade (also referred to as signaling).

"Ligand" designates a natural, i.e. formed in vivo or artificially generated, low or high molecular weight binding partner for a "receptor". The ligand is preferably able to move freely in the extracellular environment.

"Immunogen" designates a peptide fragment of the invention in glycosylated or unglycosylated form which is suitable for inducing the formation of antibodies against the immunogen. Binding of the immunogen (as hapten) to a macromolecular carrier may be advantageous where appropriate.

"Epitope" or antigenic determinant designates the region determining the antibody specificity of an antigen, such as, for example, of a protein. If this epitope is newly formed in a section of the protein or expressed on the accessible molecule surface, for example through external influences such as, for example, an interaction of a protein with a ligand, the term used is "neoepitope".

A "domain" of a protein or antibody designates a complex structure which is formed by alpha-helix and/or beta-pleated sheet elements and is demarcated within the protein.

Unless stated otherwise, the term "RGM protein of the invention" encompasses both the neogenin-binding domain and polypeptides derived therefrom of a member of the family of RGM molecules, especially RGM A, B and C. Also encompassed in particular are functional polypeptides "with inhibitory activity".

"Inhibiting" polypeptides or polypeptides "having inhibitory activity" are those which reduce or completely inhibit nerve cell growth in a nerve cell growth assay described herein.

Unless stated otherwise, "RGM" stands for RGM A, B and C, especially RGM A.

"Neogenin" or "neogenin receptor" are synonymous terms.

II. Specific Aspects of the Invention

A first aspect of the invention relates to receptor-binding, especially neogenin receptor-binding, domains of the repulsive guidance molecule (RGM) in glycosylated or especially unglycosylated form, preferably derived from RGM from mammals such as, for example, human, rat or mouse, or poultry, such as, for example, chicken.

A preferred embodiment relates to neogenin receptor-binding domains derived from a human RGM A as shown in SEQ ID NO: 2, human RGM B as shown in SEQ ID NO: 4 or human RGM C as shown in SEQ ID NO: 6. In this connection, the binding domains comprise in particular an amino acid sequence with a length of up to 150, such as, for example, up to 125, up to 100, up to 80, up to 30, or up to 20, such as, for example, 10 to 20, such as, for example, 11, 12, 13, 14, 15, 16, 17, 18 or 19, consecutive amino acid residues from an amino acid sequence region of RGM, specifically C-terminal relative to the RGD cleavage site and N-terminal relative to the GPI anchor region of RGM such as, in particular, RGM A.

The invention relates in particular to those neogenin receptor-binding domains which are characterized by the following partial sequence as shown in SEQ ID NO: 7:

$$GX_1X_2VEX_3X_4AX_5YIGTTX_6X_7X_8RQ$$

in which $X_1$ to $X_8$ are any amino acid residues.

In particular therein
$X_1$ is Gln, H is or Asn;
$X_2$ is His or Tyr
$X_3$ is Ile or Met
$X_4$ is Gln or His
$X_5$ is Lys, Arg or Ala
$X_6$ is Ile or Val
$X_7$ is Val, Phe or Ile and
$X_8$ is Val or Ile.

Specific examples which should be mentioned are:

```
GQHVEIQAKYIGTTIVVRQ (SEQ ID NO: 8)

GHYVEMHARYIGTTVFVRQ (SEQ ID NO: 9)

GNHVEIQAAYIGTTIIIRQ (SEQ ID NO: 10)
```

Examples of neogenin receptor-binding domains include an amino acid sequence from amino acid position 200-350 as shown in SEQ ID NO: 2, from amino acid position 200-330 as shown in SEQ ID NO: 4, or from amino acid position 180-350 as shown in SEQ ID NO: 6, or functional neogenin receptor-binding fragments thereof.

Such domains or fragments include in particular:
amino acid positions 200-325, 200-300, 200-285, 250-285 or 260-285 or 260-280 or the fragments 215-340, 260-340, 250-300, 260-291, 210-260 or 290-350 as shown in SEQ ID NO: 2; or
the sequence fragments of SEQ ID NO: 4 and 6 which can be derived from a sequence alignment of SEQ ID NO: 2 with SEQ ID NO: 4 and 6 (cf. appended FIG. 1) and which correspond to the amino acid positions detailed above of SEQ ID NO: 2; and
amino acid positions 200-300, 280-340, 240-300, 260-300 or 240-280 as shown in SEQ ID NO: 4 or
amino acid positions 200-350, 200-320, 220-310, 250-290 or 260-280 as shown in SEQ ID NO: 6.

Further specific examples of binding domains suitable according to the invention are:
KITEKVSGQHVEIQAKYIGTTIWRQVGRYLT (SEQ ID NO: 23) derived from RGM A;
RIVERESGHYVEMHARYIGTTVFVRQVGRYLT (SEQ ID NO: 24) derived from RGM B;
SIQTANPGNHVEIQAAYIGTTIIIRQTAGQLS (SEQ ID NO: 25) derived from RGM C.
KITEKVSGQHVEIQAK (SEQ ID NO: 26) derived from RGM A;
YIGTTIWRQVGRYLT (SEQ ID NO: 27) derived from RGM A;
WNAVEDWDSQGLYLC (SEQ ID NO: 28) derived from RGM A;
TIIFKNFQECVDQKVYQA (SEQ ID NO: 29) derived from RGM A;
RIVERESGHY VEMHAR (SEQ ID NO: 31) derived from RGM B;
YIGTTVFVRQ VGRYLT (SEQ ID NO: 32) derived from RGM B;
SIQTANPGNH VEIQAA (SEQ ID NO: 33) derived from RGM C; and
YIGTTIIIRQ TAGQLS (SEQ ID NO: 34) derived from RGM C.

Further examples of neogenin receptor-binding domains or binding fragments thereof include at least 10, such as, for example, 10-30, 10-25, 10-20 or 10-15, such as, in particular, 10, 11, 12, 13, 14, or 15, consecutive amino acid residues from one of the abovementioned peptides or from the sequence region from position 260 to 291 or 267 to 285 as shown in SEQ ID NO: 2, from the sequence region from position 260 to 325 as shown in SEQ ID NO: 4 or from the sequence region from position 250 to 300 as shown in SEQ ID NO: 6.

A further aspect of the invention relates to antigenic polypeptide fragments of the neogenin receptor-binding domains as defined above. The invention relates in particular to those antigenic polypeptide fragments which can be used to produce immunoglobulin molecules and modulate, in particular partly or completely antagonize, the binding of RGM to the neogenin receptor. Mention may be made for example of those antigenic polypeptide fragments which include at least 10, such as, for example, 10-30, 10-25, 10-20 or 10-15, such as, in particular, 10, 11, 12, 13, 14, or 15, consecutive amino acid residues of a peptide as shown in SEQ ID NO: 7, 8, 9, 10, 23 to 29 or 31 to 34.

A further aspect of the invention relates to the use of a neogenin receptor-binding domain as defined above or of a polypeptide fragment as defined above for producing a polyclonal antiserum or monoclonal antibody against RGM, where the antiserum or the antibody modulates, preferably partly or completely antagonizes, in particular the binding of RGM to the neogenin receptor.

The invention also relates to polyclonal antisera or monoclonal antibodies against RGM as defined above for use in diagnosis or therapy.

The invention also relates to the use of a polyclonal antiserum or monoclonal antibody of the invention for producing a pharmaceutical composition for the diagnosis or therapy of diseases and disease stages which are mediated by an interaction of the neogenin receptor with RGM or an RGM fragment. These diseases or disease stages are selected in particular from:
a) mechanical injuries of the skull, brain and spinal cord,
b) chronic disorders such as neurodegenerative, inflammatory and autoimmune diseases,
c) impairments of neuronal regeneration, of axonal sprouting, of axonal extension and of neuronal plasticity,
d) neoplastic diseases and tumor metastasis.

The invention further relates to the use of a neogenin receptor-binding domain as defined above or of a polypeptide fragment as defined above for producing a composition for the diagnosis or therapy of diseases or disease stages which are mediated by an impaired interaction of RGM or an RGM fragment with the associated receptor (such as, for example, the neogenin receptor). These diseases or disease stages are selected in particular from:
a) altered axonogenesis processes associated with psychotic disorders and chronic states of pain caused by excessive axon sprouting and/or pathological synaptogenesis.
b) disorders associated with an impaired iron metabolism, in particular juvenile hemochromatosis
c) disorders associated with an impaired bone growth
d) disorders associated with degenerative cartilage changes
e) disorders associated with damage to intervertebral disks and vertebrae
f) disorders associated with deregulated, uncontrolled cell migration processes.

A further aspect of the invention relates to the use of a neogenin receptor-binding domain as defined above or of a polypeptide fragment as defined above as target for detecting or for identifying RGM-binding ligands.

Another aspect of the invention relates to the use of a neogenin receptor-binding domain as defined above or of a polypeptide fragment as defined above as immunogen for active or passive immunization.

The invention also relates to polyclonal antisera obtainable by immunization of a mammal with an antigenic amount of a neogenin receptor-binding domain as defined above or of a polypeptide fragment as defined above; and monoclonal antibodies against a neogenin receptor-binding domain as defined above or against a polypeptide fragment as defined above, and antigen-binding fragments thereof, where appropriate in humanized form.

The invention also relates to pharmaceutical compositions comprising in a pharmaceutically suitable carrier at least one active ingredient selected from:
a) a neogenin receptor-binding domain as defined above or a polypeptide fragment as defined above or
b) monoclonal or polyclonal antibodies as defined above.

Pharmaceutical compositions of this type are used in particular for intrathecal, intravenous, subcutaneous, oral or parenteral, nasal and inhalational administration.

The invention further relates to an expression vector comprising at least one coding nucleic acid sequence for a neogenin receptor-binding domain as defined above or for a polypeptide fragment as defined above, operatively linked to at least one regulatory nucleic acid sequence.

The invention further relates to:
recombinant microorganisms which harbor at least one vector as defined above.
hybridomal cell lines which produce a monoclonal antibody as defined above.
methods for producing a neogenin receptor-binding domain as defined above or a polypeptide fragment as defined above, where a recombinant microorganism as defined above is cultured, and the produced protein product is isolated from the culture. In this case a hybridoma cell line as defined above is cultured, and the produced protein product is isolated from the culture.

III. Further Information for Implementation of the Invention

1. Polypeptides

The invention relates in particular to binding domains of proteins of the RGM family and peptide fragments derived from these domains. Whereas RGM A and its binding domain and fragments derived therefrom were investigated in particular according to the invention, the invention also relates to corresponding domains and fragments of homologous proteins, such as, in particular, homologous members of the RGM family, such as, in particular, RGM B and RGM C.

"Functional equivalents" or analogs of the specifically disclosed RGM domains or polypeptides are in the context of the present invention polypeptides which differ therefrom, such as, for example, those having a degree of homology of less than 100% to the neogenin binding domains of proteins as shown in SEQ ID NO: 2, 4 or 6, but which still possess the desired biological activity. In particular, they should be capable of binding to the neogenin receptor and/or show an inhibitory effect in a nerve fiber growth assay described herein and moreover inhibit partly or completely, statistically significantly ($p<=0.05$), nerve fiber growth.

"Functional equivalents" mean according to the invention in particular mutants which have in at least one of the sequence positions of the abovementioned specific sequences an amino acid which differs from that specifically mentioned, but nevertheless have one of the biological activities mentioned herein. "Functional equivalents" thus comprise the mutants obtainable by one or more amino acid additions, substitutions, deletions and/or inversions, it being possible for said changes to occur in any sequence position as long as they lead to a mutant having the profile of properties according to the invention. Functional equivalence exists in particular also when there is a qualitative agreement between the mutant and unmodified polypeptide in the reactivity pattern, i.e. for example identical biological effects are to be observed but differ greatly in the level of expression. Examples of suitable substitutions of amino acid residues are the following:

| Original residue | Examples of substitution |
| --- | --- |
| Ala | Ser |
| Arg | Lys |
| Asn | Gln; His |
| Asp | Glu |
| Cys | Ser |
| Gln | Asn |
| Glu | Asp |
| Gly | Pro |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

"Functional equivalents" in the above sense are also precursors of the polypeptides described, and functional derivatives and salts of the polypeptides. The term "salts" means both salts of carboxyl groups and acid addition salts of amino groups of the protein molecules of the invention. Salts of carboxyl groups can be prepared in a manner known per se and comprise inorganic salts such as, for example, sodium, calcium, ammonium, iron and zinc salts, and salts with organic bases such as, for example, amines, such as triethanolamine, arginine, lysine, piperidine and the like. Acid addition salts such as, for example, salts with mineral acids such as hydrochloric acid or sulfuric acid and salts with organic acids, such as acetic acid and oxalic acid are likewise an aspect of the invention. "Functional derivatives" of polypeptides of the invention can likewise be prepared on functional amino acid side groups or on their N- or C-terminal end with the aid of known techniques. Derivatives of these types comprise for example aliphatic esters of carboxylic acid groups, amides of carboxylic acid groups, obtainable by reaction with ammonia or with a primary or secondary amine; N-acyl derivatives of free amino groups prepared by reaction with acyl groups; or O-acyl derivatives of free hydroxy groups prepared by reaction with acyl groups.

"Functional equivalents" of course also comprise polypeptides obtainable from other organisms, and naturally occurring variants. For example, areas of homologous sequence regions can be found by sequence comparison, and equivalent enzymes can be established on the basis of the specific requirements of the invention.

"Functional equivalents" are moreover fusion proteins having one of the abovementioned polypeptide sequences or functional equivalents derived therefrom, and at least one further heterologous sequence functionally different therefrom in functional N- or C-terminal linkage (i.e. with negligible mutual functional impairment of the portions of the fusion proteins). Nonlimiting examples of such heterologous sequences are, for example, enzymes and immunoglobulins.

"Functional equivalents" also comprised by the invention are homologs of the specifically disclosed proteins and peptides. These have at least 40%, or at least 50%, or at least 60%, such as, for example, at least 75%, or in particular at least 85%, such as, for example, 90%, 95% or 99%, homology to one of the specifically disclosed sequences, calculated, for example, by the algorithm of Pearson and Lipman, Proc. Natl. Acad, Sci. (USA) 85(8), 1988, 2444-2448. A percentage homology of a homologous polypeptide of the invention means in particular the percentage identity of the amino acid residue based on the complete length of one of the amino acid sequences specifically described herein.

A "derived" amino acid sequence means according to the invention, unless indicated otherwise, a sequence which has an identity of at least 80% or at least 90%, in particular 91%, 92%, 93%, 94%, 95%, 96%, 97%, 98% and 99%, with the initial sequence.

"Identity" between two sequences means identity of the amino acid residues over the complete length of the sequence in each case, such as, for example, the identity calculated by comparison with the aid of the Vector NTI Suite 7.1 Software from Informax (USA) using the Clustal method (Higgins DG, Sharp PM. Fast and sensitive multiple sequence alignments on a microcomputer. Comput Appl. Biosci. 1989 April; 5(2): 151-1), setting the following parameters:

Multiple alignment parameter:

|  |  |
|---|---|
| Gap opening penalty | 10 |
| Gap extension penalty | 10 |
| Gap separation penalty range | 8 |
| Gap separation penalty | off |
| % identity for alignment delay | 40 |
| Residue specific gaps | off |
| Hydrophilic residue gap | off |
| Transition weighing | 0 |

Pairwise alignment parameter:

|  |  |
|---|---|
| FAST algorithm | on |
| K-tuple size | 1 |
| Gap penalty | 3 |
| Window size | 5 |
| Number of best diagonals | 5 |

For further illustration of homologs included according to the invention, reference is made to the following table which shows the percentage agreement of RGM B and C with RGM A for the full-length protein and for certain partial sequence regions which are of particular interest according to the invention.

|  | RGM A - RGM B | RGM A - RGM C |
|---|---|---|
| Full-length proteins | 51%[2)3)] | 47% |
| AA[1)] 200-350 | 62%[2)] | 55% |
| AA 200-325 | 61% | 55% |
| AA 200-300 | 66% | 60% |
| AA 200-285 | 65% | 66% |
| AA 250-285 | 58% | 61% |
| AA 260-285 | 57% | 78% |

[1)]Amino acids residue, indication of position based on RGM A sequence (SEQ ID NO: 2)
[2)]Amino acid identity of the full-length proteins and of the peptide fragments in percent
[3)]Method: BLAST 2 SEQUENCES VERSION BLASTP 2.2.5 [Nov. 16, 2002] Matrix: Blosum62 (gap open: 11 gap extension: 1)

In the case where protein glycosylation is possible, equivalents of the invention comprise proteins of the type designated above in deglycosylated or glycosylated form and modified forms obtainable by altering the glycosylation pattern.

Homologs of the peptides of the invention can be identified by screening combinatorial libraries of mutants such as, for example, truncation mutants. For example, it is possible to generate a variegated library of peptide variants by combinatorial mutagenesis at the nucleic acid level, such as, for example, by enzymatic ligation of a mixture of synthetic oligonucleotides. There is a large number of methods which can be used to produce libraries of potential homologs from a degenerate oligonucleotide sequence. Chemical synthesis of a degenerate gene sequence can be carried out in an automatic DNA synthesizer, and the synthetic gene can then be ligated into a suitable expression vector. The use of a degenerate set of genes makes it possible to provide all sequences which encode the desired set of potential protein sequences in one mixture. Methods for synthesizing degenerate oligonucleotides are known to the skilled worker (e.g. Narang, S. A. (1983) Tetrahedron 39:3; Itakura et al. (1984) Annu. Rev. Biochem. 53:323; Itakura et al., (1984) Science 198:1056; Ike et al. (1983) Nucleic Acids Res. 11:477).

2. Nucleic Acids

The invention further relates to the coding nucleic acid sequences for the RGM binding domains and polypeptides described above, such as, in particular, as shown in SEQ ID NO: 1, 3 and 5, and nucleic acid sequences or partial sequences derived therefrom.

All nucleic acid sequences of the invention (single- and double-stranded DNA and RNA sequences, such as, for example, cDNA and mRNA) can be prepared in a manner known per se by chemical synthesis from the nucleotide units, such as, for example, by fragment condensation of individual overlapping, complementary nucleic acid units of the double helix. Chemical synthesis of oligonucleotides can take place for example in a known manner by the phosphoamidite method (Voet, Voet, 2nd edition, Wiley Press New York, pages 896-897). Addition of synthetic oligonucleotides and filling in of gaps using the Klenow fragment of DNA polymerase and ligation reactions, and general cloning methods are described in Sambrook et al. (1989), Molecular Cloning: A laboratory manual, Cold Spring Harbor Laboratory Press.

A "derived" nucleic acid sequence means according to the invention, unless indicated otherwise, a sequence which has an identity of at least 80% or at least 90%, in particular 91%, 92%, 93%, 94%, 95%, 96%, 97%, 98% and 99%, with the initial sequence.

"Identity" between two nucleic acids means the identity of the nucleotides over the complete length of the nucleic acid in each case, in particular the identity which is obtained by comparison with the aid of the Vector NTI Suite 7.1 Software from Informax (USA) using the Clustal method (see above).

The invention also relates to nucleic acid sequences coding for one of the above peptides and their functional equivalents, which can be obtained for example by use of artificial nucleotide analogs.

The invention relates both to isolated nucleic acid molecules which code for peptides of the invention or biologically active segments thereof, and nucleic acid fragments which can be used for example as hybridization probes or primers for identifying or amplifying coding nucleic acids of the invention.

The nucleic acid molecules of the invention may additionally comprise untranslated sequences from the 3' and/or 5' end of the coding region of the gene.

An "isolated" nucleic acid molecule is separated from other nucleic acid molecules which are present in the natural source of the nucleic acid and may moreover be substantially free of other cellular material or culture medium if it is prepared by recombinant techniques, or free of chemical precursors or other chemicals if it is synthesized chemically.

A nucleic acid molecule of the invention can be isolated by means of standard techniques of molecular biology and the sequence information provided by the invention. For example, cDNA can be isolated from a suitable cDNA library by using one of the specifically disclosed complete sequences or a segment thereof as hybridization probe and standard hybridization techniques (as described for example in Sambrook, J., Fritsch, E. F. and Maniatis, T. Molecular Cloning: A Laboratory Manual. 2nd edition, Cold Spring Harbor Laboratory, Cold Spring Harbor Laboratory Press, Cold Spring Harbor, N.Y., 1989). It is moreover possible to isolate a nucleic acid molecule comprising one of the sequences of the invention or a segment thereof by polymerase chain reaction using the oligonucleotide primers constructed on the basis of this sequence. The nucleic acid amplified in this way can be cloned into a suitable vector and characterized by DNA sequence analysis. The oligonucleotides of the invention can also be prepared by standard synthesis methods, e.g. using an automatic DNA synthesizer.

The invention further comprises the nucleic acid molecules complementary to the specifically described nucleotide sequences, or a segment thereof.

The nucleotide sequences of the invention make it possible to produce probes and primers which can be used for identifying and/or cloning homologous sequences in other cell types and organisms. Such probes and primers usually comprise a nucleotide sequence region which hybridizes under stringent conditions to at least about 12, preferably at least about 25, such as, for example, about 40, 50 or 75, consecutive nucleotides of a sense strand of a nucleic acid sequence of the invention or of a corresponding antisense strand.

Further nucleic acid sequences of the invention are derived from coding sequences for the RGM domains and peptides of the invention and differ therefrom by addition, substitution, insertion or deletion of one or more nucleotides, but still code for peptides having the desired profile of properties.

The invention also comprises nucleic acid sequences which comprise so-called silent mutations, or are modified in accordance with the codon usage of a specific original or host organism compared with a specifically mentioned sequence, as well as naturally occurring variants such as, for example, splice variants or allelic variants, thereof. Sequences obtainable by conservative nucleotide substitutions (i.e. the relevant amino acid is replaced by an amino acid of the same charge, size, polarity and/or solubility) are likewise an aspect.

The invention also relates to the molecules derived from the specifically disclosed nucleic acids through sequence polymorphisms. These genetic polymorphisms may exist because of the natural variation between individuals within a population. These natural variations normally result in a variance of from 1 to 5% in the nucleotide sequence of a gene.

The invention further also comprises nucleic acid sequences which hybridize with the abovementioned coding sequences or are complementary thereto. These polynucleotides can be found by screening genomic or cDNA libraries and if appropriate be amplified therefrom by means of PCR with suitable primers, and subsequently isolated for example with suitable probes. A further possibility is the transformation of suitable microorganisms with polynucleotides or vectors of the invention, to multiply the microorganisms and thus the polynucleotides and subsequently to isolate them. An additional possibility is to synthesize polynucleotides of the invention also by a chemical route.

The property of being able to "hybridize" onto polynucleotides means the ability of a polynucleotide or oligonucleotide to bind under stringent conditions to an almost complementary sequence, while there are nonspecific bindings between non-complementary partners under these conditions. For this purpose, the sequences should be 70-100%, in particular 90-100%, such as, for example, 95%, 96%, 97%, 98%, or 99%, complementary. The property of complementary sequences being able to bind specifically to one another is made use of, for example, in the Northern or Southern blotting technique or in the primer binding in PCR or RT-PCR. Oligonucleotides with a length of 30 base pairs or more are normally employed for this purpose. Stringent conditions mean, for example, in the Northern blotting technique the use of a washing solution, for example 0.1×SSC buffer with 0.1% SDS (20×SSC: 3M NaCl, 0.3M Na citrate, pH 7.0), at 50-70° C., preferably 60-65° C., for eluting nonspecifically hybridized cDNA probes or oligonucleotides. In this case, as mentioned above, only nucleic acids with a high degree of complementarity remain bound to one another. The setting up of stringent conditions is known to the skilled worker and is described for example in Ausubel et al., Current Protocols in Molecular Biology, John Wiley & Sons, N.Y. (1989), 6.3.1-6.3.6.

A further aspect of the invention relates to antisense nucleic acids. This comprises a nucleotide sequence which is complementary to a coding sense nucleic acid. The antisense nucleic acid may be complementary to the entire coding strand or only to a section thereof. In a further embodiment, the antisense nucleic acid molecule is antisense to a noncoding region of the coding strand of a nucleotide sequence. The term "non-coding region" relates to the sequence sections which are referred to as 5'- and 3'-untranslated regions.

An antisense oligonucleotide may be, for example, about 5, 10, 15, 20, 25, 30, 35, 40, 45 or 50 nucleotides long. An antisense nucleic acid of the invention can be constructed by chemical synthesis and enzymatic ligation reactions using methods known in the art. An antisense nucleic acid can be synthesized chemically, using naturally occurring nucleotides or variously modified nucleotides which are configured so that they increase the biological stability of the molecules or increase the physical stability of the duplex formed between the antisense and sense nucleic acids. Examples which can be used are phosphorothioate derivatives and acridine-substituted nucleotides. Examples of modified nucleotides which can be used for generating the antisense nucleic acid are, inter alia, 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueuosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosyl-queuosine, 5'-methoxycarboxymethyluracil, 5-methoxyuracil, 2-methylthio-N6-isopentenyladenine, uracil-5-oxyacetic acid (v), wybutoxosine, pseudouracil, queuosine, 2-thiocytosine, 5-methyl-2-thiouracil, 2-thiouracil, 4-thiouracil, 5-methyluracil, methyl uracil-5-oxyacetate, uracil-5-oxyacetic acid (v), 5-methyl-2-thiouracil, 3-(3-amino-3-N-2-carboxypropyl) uracil, (acp3)w and 2,6-diaminopurine. The antisense nucleic acid may also be produced biologically by using an expression vector into which a nucleic acid has been subcloned in the antisense direction.

3. Expression Constructs and Vectors

The invention additionally relates to expression constructs comprising, under the genetic control of regulatory nucleic acid sequences, a nucleic acid sequence coding for an RGM protein of the invention or functional equivalent or immunoglobulin, and to vectors comprising at least one of these expression constructs.

Such constructs of the invention preferably comprise a promoter 5'-upstream from the particular coding sequence, and a terminator sequence 3'-downstream, and, if appropriate, other usual regulatory elements, in particular each operatively linked to the coding sequence. "Operative linkage" means the sequential arrangement of promoter, coding sequence, terminator and, if appropriate, other regulatory elements in such a way that each of the regulatory elements is able to comply with its function as intended for expression of the coding sequence. Examples of sequences which can be operatively linked are targeting sequences and enhancers, polyadenylation signals and the like. Other regulatory elements comprise selectable markers, amplification signals, origins of replication and the like. Suitable regulatory sequences are described, for example, in Goeddel, Gene Expression Technology: Methods in Enzymology 185, Academic Press, San Diego, Calif. (1990).

In addition to the artificial regulatory sequences it is possible for the natural regulatory sequence still to be present in front of the actual structural gene. This natural regulation can, if appropriate, be switched off by genetic modification, and expression of the genes can be increased or decreased. The gene construct can, however, also have a simpler structure, that is to say no additional regulatory signals are inserted in front of the structural gene, and the natural promoter with its regulation is not deleted. Instead, the natural regulatory sequence is mutated so that regulation no longer takes place, and gene expression is enhanced or diminished. The nucleic acid sequences may be present in one or more copies in the gene construct.

Examples of promoters which can be used are: cos, tac, trp, tet, trp-tet, lpp, lac, lpp-lac, laclq, T7, T5, T3, gal, trc, ara, SP6, lambda-PR or lambda-PL promoter, which are advantageously used in Gram-negative bacteria; and the Gram-positive promoters amy and SPO2, the yeast promoters ADC1, MFalpha, AC, P-60, CYC1, GAPDH or the plant promoters CaMV/35S, SSU, OCS, lib4, usp, STLS1, B33, not or the ubiquitin or phaseolin promoter. The use of inducible promoters is particularly preferred, such as, for example, light- and, in particular, temperature-inducible promoters such as the $P_rP_l$ promoter. It is possible in principle for all natural promoters with their regulatory sequences to be used. In addition, it is also possible advantageously to use synthetic promoters.

Said regulatory sequences are intended to make specific expression of the nucleic acid sequences and protein expression possible. This may mean, for example, depending on the host organism, that the gene is expressed or overexpressed only after induction or that it is immediately expressed and/or overexpressed.

The regulatory sequences or factors may moreover preferably influence positively, and thus increase or reduce, expression. Thus, enhancement of the regulatory elements can take place advantageously at the level of transcription by using strong transcription signals such as promoters and/or enhancers. However, it is also possible to enhance translation by, for example, improving the stability of the mRNA.

An expression cassette is produced by fusing a suitable promoter to a suitable coding nucleotide sequence and to a terminator signal or polyadenylation signal. Conventional techniques of recombination and cloning are used for this purpose, as described, for example, in T. Maniatis, E. F. Fritsch and J. Sambrook, Molecular Cloning: A Laboratory Manual, Cold Spring Harbor Laboratory, Cold Spring Harbor, N.Y. (1989) and in T. J. Silhavy, M. L. Berman and L. W. Enquist, Experiments with Gene Fusions, Cold Spring Harbor Laboratory, Cold Spring Harbor, N.Y. (1984) and in Ausubel, F. M. et al., Current Protocols in Molecular Biology, Greene Publishing Assoc. and Wiley Interscience (1987).

For expression in a suitable host organism, the recombinant nucleic acid construct or gene construct is advantageously inserted into a host-specific vector, which makes optimal expression of the genes in the host possible. Vectors are well known to the skilled worker and can be found, for example, in "Cloning Vectors" (Pouwels P. H. et al., eds, Elsevier, Amsterdam-New York-Oxford, 1985). Vectors also mean not only plasmids but also all other vectors known to the skilled worker, such as, for example, phages, viruses, such as SV40, CMV, baculovirus and adenovirus, transposons, IS elements, phasmids, cosmids, and linear or circular DNA. These vectors may undergo autonomous replication in the host organism or chromosomal replication.

Examples of suitable expression vectors which may be mentioned are:

Conventional fusion expression vectors such as pGEX (Pharmacia Biotech Inc; Smith, D. B. and Johnson, K. S. (1988) Gene 67:31-40), pMAL (New England Biolabs, Beverly, Mass.) and pRIT 5 (Pharmacia, Piscataway, N.J.), with which respectively glutathione S-transferase (GST), maltose E-binding protein and protein A are fused to the recombinant target protein.

Nonfusion protein expression vectors such as pTrc (Amann et al., (1988) Gene 69:301-315) and pET 11d (Studier et al. Gene Expression Technology: Methods in Enzymology 185, Academic Press, San Diego, Calif. (1990) 60-89).

Yeast expression vector for expression in the yeast S. cerevisiae, such as pYepSec1 (Baldari et al., (1987) Embo J. 6:229-234), pMFa (Kurjan and Herskowitz (1982) Cell 30:933-943), pJRY88 (Schultz et al. (1987) Gene 54:113-123) and pYES2 (Invitrogen Corporation, San Diego, Calif.). Vectors and methods for constructing vectors suitable for use in other fungi such as filamentous fungi comprise those which are described in detail in: van den Hondel, C. A. M. J. J. & Punt, P. J. (1991) "Gene transfer systems and vector development for filamentous fungi, in: Applied Molecular Genetics of Fungi, J. F. Peberdy et al., eds, pp. 1-28, Cambridge University Press: Cambridge.

Baculovirus vectors which are available for expression of proteins in cultured insect cells (for example Sf9 cells) comprise the pAc series (Smith et al., (1983) Mol. Cell. Biol. 3:2156-2165) and pVL series (Lucklow and Summers (1989) Virology 170:31-39).

Plant expression vectors such as those described in detail in: Becker, D., Kemper, E., Schell, J. and Masterson, R. (1992) "New plant binary vectors with selectable markers located proximal to the left border", Plant Mol. Biol. 20:1195-1197; and Bevan, M. W. (1984) "Binary *Agrobacterium* vectors for plant transformation", Nucl. Acids Res. 12:8711-8721.

Mammalian expression vectors such as pCDM8 (Seed, B. (1987) Nature 329:840) and pMT2PC (Kaufman et al. (1987) EMBO J. 6:187-195).

Further suitable expression systems for prokaryotic and eukaryotic cells are described in chapters 16 and 17 of Sambrook, J., Fritsch, E. F. and Maniatis, T., Molecular cloning: A Laboratory Manual, 2nd edition, Cold Spring Harbor Laboratory, Cold Spring Harbor Laboratory Press, Cold Spring Harbor, N.Y., 1989.

4. Recombinant Host Organisms:

The vectors of the invention can be used to produce recombinant organisms which are transformed, for example, with at least one vector of the invention and can be employed for producing the domains or polypeptides of the invention. The recombinant constructs of the invention described above are advantageously introduced and expressed in a suitable host system. Cloning and transfection methods familiar to the skilled worker, such as, for example, coprecipitation, protoplast fusion, electroporation, retroviral transfection and the like, are preferably used to bring about expression of said nucleic acids in the particular expression system. Suitable systems are described, for example, in Current Protocols in Molecular Biology, F. Ausubel et al., eds, Wiley Interscience, New York 1997, or Sambrook et al. Molecular Cloning: A Laboratory Manual, 2nd edition, Cold Spring Harbor Laboratory, Cold Spring Harbor Laboratory Press, Cold Spring Harbor, N.Y., 1989.

Suitable host organisms are in principle all organisms which enable expression of the nucleic acids of the invention, their allelic variants, their functional equivalents or derivatives. Host organisms mean, for example, bacteria, fungi, yeasts, plant or animal cells. Preferred organisms are bacteria, such as those of the genera *Escherichia*, such as, for example, *Escherichia coli*, *Streptomyces*, *Bacillus* or *Pseudomonas*, eukaryotic microorganisms such as *Saccharomyces cerevisiae*, *Aspergillus*, higher eukaryotic cells from animals or plants, for example Sf9, CHO or HEK293 cells.

Successfully transformed organisms can be selected through marker genes which are likewise present in the vector or in the expression cassette. Examples of such marker genes are genes for antibiotic resistance and for enzymes which catalyze a color-forming reaction which causes staining of the transformed cell. These can then be selected by automatic cell sorting. Microorganisms which have been successfully transformed with a vector and harbor an appropriate antibiotic resistance gene (for example G418 or hygromycin) can be selected by appropriate antibiotic-containing media or nutrient media. Marker proteins present on the surface of the cell can be used for selection by means of affinity chromatography.

If desired, the gene product can also be expressed in transgenic organisms such as transgenic animals such as, in particular, mice, sheep or transgenic plants.

The invention further relates to methods for the recombinant production of RGM domains or polypeptides of the invention or functional, biologically active fragments thereof, wherein a peptide-producing recombinant host organism is cultured, expression of the polypeptides is induced if appropriate, and they are isolated from the culture. The peptides can also be produced on the industrial scale in this way if desired.

The recombinant host can be cultured and fermented by known methods. Bacteria can be grown, for example, in TB or LB medium and at a temperature of 20 to 40° C. and a pH of from 6 to 9. Details of suitable culturing conditions are described, for example, in T. Maniatis, E. F. Fritsch and J. Sambrook, Molecular Cloning: A Laboratory Manual, Cold Spring Harbor Laboratory, Cold Spring Harbor, N.Y. (1989).

If the polypeptides are not secreted into the culture medium, the cells are then disrupted and the product is obtained from the lysate by known protein isolation methods. The cells may alternatively be disrupted by high-frequency ultrasound, by high pressure, such as, for example, in a French pressure cell, by osmolysis, by the action of detergents, lytic enzymes or organic solvents, by homogenizers or by a combination of a plurality of the methods mentioned.

The peptides can be purified by known chromatographic methods such as molecular sieve chromatography (gel filtration), such as Q-Sepharose chromatography, ion exchange chromatography and hydrophobic chromatography, and by other usual methods such as ultrafiltration, crystallization, salting out, dialysis and native gel electrophoresis. Suitable methods are described, for example, in Cooper, T. G., Biochemische Arbeitsmethoden, Verlag Walter de Gruyter, Berlin, New York or in Scopes, R., Protein Purification, Springer Verlag, New York, Heidelberg, Berlin.

It is particularly advantageous for isolation of the recombinant peptide to use vector systems or oligonucleotides which extend the cDNA by particular nucleotide sequences and thus code for modified polypeptides or fusion proteins which serve, for example, for simpler purification. Suitable modifications of this type are, for example, so-called tags which act as anchors, such as, for example, the modification known as hexa-histidine anchor, or epitopes which can be recognized as antigens by antibodies (described, for example, in Harlow, E. and Lane, D., 1988, Antibodies: A Laboratory Manual. Cold Spring Harbor (N.Y.) Press). These anchors can be used to attach the peptides to a solid support, such as, for example, a polymer matrix, which can, for example, be packed into a chromatography column, or can be used on a microtiter plate or another support.

These anchors can at the same time also be used for recognition of the peptides. It is also possible to use for recognition of the peptides conventional markers such as fluorescent dyes, enzyme markers which form a detectable reaction product after reaction with a substrate, or radioactive labels, alone or in combination with the anchors for derivatizing the peptides.

5. Immunoglobulins 5.1 Definition

The present invention relates to monoclonal or polyclonal antibodies which bind specifically to an RGM protein of the invention or derivative/equivalent thereof, i.e. antibodies having specificity for an RGM protein of the invention or derivative/equivalent thereof. The present invention also relates to parts of these antibodies, especially antigen-binding parts thereof, i.e. antibody fragments which bind an RGM protein of the invention or a derivative/equivalent thereof.

The antibody of the invention is preferably chosen so that it has particular binding kinetics (e.g. high affinity, little dissociation, low off rate (koff), strong neutralizing activity) for the specific binding to RGM protein of the invention or derivate/equivalent thereof.

Thus, antibodies with an affinity for the RGM protein of the invention or derivative/equivalent thereof in the region of $K_D=10^{-6}$-$10^{-12}$ M can be provided.

According to a further aspect, the antibodies of the invention can be chosen so that they bind the RGM protein or derivative/equivalent thereof with a $k_{off}$ rate constant of 0.1 $s^{-1}$ or less.

The antibodies are preferably isolated antibodies. According to a further aspect, the antibodies are neutralizing antibodies. The antibodies of the invention include in particular monoclonal and recombinant antibodies. The antibodies of the invention may comprise an amino acid sequence which derives completely from a single species, and thus may be for example a human antibody or a mouse antibody. According to further embodiments, the antibody may be a chimeric antibody or a CDR graft antibody or another type of humanized antibody.

The term "antibody" is intended to refer to immunoglobulin molecules which are formed from 4 polypeptide chains, two heavy (H) chains and two light (L) chains. The chains are usually linked together by disulfide bonds. Every heavy chain is composed of a variable region of the heavy chain (abbreviated here to HCVR or VH) and a constant region of the heavy chain. The constant region of the heavy chain is formed from three domains CH1, CH2 and CH3. Each light chain is composed of a variable region of the light chain (abbreviated here to LCVR or VL) and a constant region of the light chain. The constant region of the light chain is formed from a CL domain. The VH and VL regions may be further divided into hypervariable regions which are referred to as complementarity-determining regions (CDR) and are interspersed with more conserved regions which are referred to as framework regions (FR). Each VH and VL region is formed from three CDRs and four FRs which are arranged from the N terminus to the C terminus in the following sequence: FR1, CDR1, FR2, CDR2, FR3, CDR3, FR4.

The term "antigen-binding part" of an antibody (or simply "antibody part") refers to one or more fragments of an antibody having specificity for an RGM protein of the invention or derivative/equivalent thereof, the fragment(s) still having the ability to bind specifically the RGM protein or derivative/equivalent thereof. It has been shown that the antigen-binding function of an antibody can be undertaken by fragments of a complete antibody. Examples of binding fragments include within the meaning of the term "antigen-binding part" of an antibody (i) an Fab fragment, i.e. a monovalent fragment composed of the VL, VH, CL and CH1 domains; (ii) an F(ab')$_2$ fragment, i.e. a bivalent fragment which comprises two Fab fragments linked together by a disulfide bridge in the hinge region; (iii) an Fd fragment which is composed of the VH and CH1 domains; (iv) an Fv fragment which is composed of the VL and VH domains of a single arm of an antibody; (v) a dAb fragment (Ward et al., (1989) *Nature* 341:544-546) which consists of a VH domain or VH, CH1, CH2, DH3, or VH, CH2, CH3; and (vi) an isolated complementarity-determining region (CDR). Although the two domains of the Fv fragment, namely VL and VH, are encoded by separate genes they can furthermore be connected together by a synthetic linker by use of recombinant methods, whereby they can be produced as a single protein chain in which the VL and VH regions are present together in order to form monovalent molecules (known as single-chain Fv (ScFv), see, for example, Bird et al. (1988) *Science* 242:423-426; and Huston et al. (1988) *Proc. Nat. Acad. Sci. USA* 85:5879-5883). Such single-chain antibodies are also intended to be encompassed by the term "antigen-binding part" of an antibody. Other types of single-chain antibodies such as diabodies likewise belong thereto. Diabodies are bivalent, bispecific antibodies in which VH and VL domains are expressed on a single polypeptide chain, but with use of a linker which is too short for the two domains to be present together on the same chain, the domains thus being forced to pair with complementary domains of another chain and to form two antigen-binding sites (see, for example, Holliger, P., et al. (1993) *Proc. Natl. Acad. Sci. USA* 90:6444-6448; Poljak, R. J., et al. (1994) *Structure* 2:1121-1123).

A further possibility is for an antibody or antigen-binding part thereof to be part of a larger immunoadhesion molecule which is formed by covalent or non-covalent association of the antibody or antibody part with one or more further proteins or peptides. Such immunoadhesion molecules involve the use of the streptavidin core region in order to produce a tetrameric scFv molecule (Kipriyanov, S. M., et al. (1995) *Human Antibodies and Hybridomas* 6:93-101) and the use of a cysteine residue, of a marker peptide and of a C-terminal polyhistidine tag in order to make bivalent and biotinylated scFv molecules (Kipriyanov, S. M., et al. (1994) *Mol. Immunol.* 31:1047-1058).

Antibody parts, such as Fab and F(ab')$_2$ fragments, can be produced from whole antibodies by using conventional techniques such as digestion with papain or pepsin. It is additionally possible to obtain antibodies, antibody parts and immunoadhesion molecules by using standardized recombinant DNA techniques. An "isolated antibody having specificity for an RGM protein of the invention or derivative/equivalent thereof" describes an antibody which has specificity for an RGM protein of the invention or derivative/equivalent thereof and which is substantially free of other antibodies having different antigen specificities.

The term "neutralizing antibody" describes an antibody whose binding to a particular antigen leads to inhibition of the biological activity of the antigen. This inhibition of the biological activity of the antigen can be assessed by measuring one or more indicators of the biological activity of the antigen, using a suitable in vitro or in vivo assay.

The term "monoclonal antibody" describes an antibody which is derived from a hybridoma (e.g. an antibody which is secreted by a hybridoma produced by means of hybridoma technology such as the standardized hybridoma methods of Köhler and Milstein). An antibody derived from a hybridoma and having specificity for an RGM protein of the invention or derivative/equivalent thereof is therefore referred to as a monoclonal antibody.

The term "recombinant antibody" describes antibodies which are produced, expressed, generated or isolated by recombinant means, such as antibodies which are expressed by use of a recombinant expression vector transfected into a host cell; antibodies isolated from a recombinant combinatorial antibody library; antibodies isolated from an animal (e.g. a mouse) which is transgenic due to human immunoglobulin genes (see, for example, Taylor, L. D., et al. (1992) *Nucl. Acids Res.* 20:6287-6295); or antibodies which are produced, expressed, generated or isolated in any other way in which particular immunoglobulin gene sequences (such as human immunoglobulin gene sequences) are combined with other DNA sequences. Recombinant antibodies include, for example, chimeric, CDR graft and humanized antibodies.

The term "human antibody" describes antibodies whose variable and constant regions correspond to immunoglobulin sequences of the human germline, as described for example by Kabat et al. (see Kabat, et al. (1991) *Sequences of Proteins of Immunological Interest, Fifth Edition*, U.S. Department of Health and Human Services, NIH Publication No. 91-3242), or are derived therefrom. The human antibodies of the invention may, however, comprise amino acid residues which are not encoded by human germline immunoglobulin sequences (e.g. mutations introduced by random or site-specific mutagenesis in vitro or by somatic mutation in vivo), for example in the CDRs, and especially in CDR3. Recombinant human antibodies of the invention have variable regions and may also comprise constant regions derived from immunoglobulin sequences of the human germline (see Kabat, E. A., et al. (1991) *Sequences of Proteins of Immunological Interest, Fifth Edition*, U.S. Department of Health and Human Services, NIH Publication No. 91-3242). According to particular embodiments, such recombinant human antibodies are, however, subjected to an in vitro mutagenesis (or to a somatic in vivo mutagenesis if an animal which is transgenic due to human Ig sequences is used), so that the amino acid sequences of the VH and VL regions of the recombinant antibodies are sequences which, although they are related to VH and VL sequences of the human germline or are derived therefrom, do not naturally exist within the human antibody germline repertoire in vivo. According to particular embodiments, such recombinant antibodies are the result of a selective mutagenesis or back-mutation, or both.

The term "back-mutation" refers to a method in which some or all of the somatically mutated amino acids of a human antibody are replaced by the corresponding germline residues of a homologous germline antibody sequence. The sequences of the heavy and light chain of a human antibody of the invention are separately compared with the germline sequences in the VBASE database in order to identify the sequences with the greatest homology. Deviations in the human antibody of the invention are returned to the germline sequence by mutation at defined nucleotide positions which encode such deviant amino acids. The direct or indirect significance of each amino acid, identified in this way as candidate for back-mutation, for antigen binding was to be investigated, and an amino acid which, after mutation, impairs a desirable property of the human antibody was not to be included in the eventual human antibody. In order to minimize the number of amino acids for a back-mutation, it is possible to leave unchanged those amino acid positions which, although deviating from the closest germine sequence, are identical to the corresponding amino acid sequence of a second germline sequence, provided that the second germine sequence is identical and colinear with the sequence of the human antibody of the invention in at least 10 and preferably in 12 amino acids on both sides of the amino acid in question. Back-mutations can be undertaken at any stage in antibody optimization.

The term "chimeric antibody" comprises antibodies in which individual parts of the molecule are derived from different species. Thus, chimeric antibodies are, without being restricted thereto, for example antibodies which comprise sequences for the variable region of the heavy and light chain from one species, but in which the sequences of one or more of the CDR regions from VH and/or VL are replaced by CDR sequences of another species. The variable regions in such antibodies may have mouse heavy and light chains in which one or more of the mouse CDRs (e.g. CDR3) are replaced by human CDR sequences.

The term "humanized antibody" describes antibodies which comprise sequences of the variable region of heavy and light chain from a non-human species (e.g. mouse, rat, rabbit, chicken, camelid, goat), but in which at least one part of the VH and/or VL sequence has been modified in order to be "more human-like", i.e. be like variable sequences of the human germline. One type of humanized antibody is a CDR graft antibody in which human CDR sequences are inserted into non-human VH and VL sequences in order to replace the corresponding non-human CDR sequences.

A method for measuring the binding kinetics of an antibody is based on so-called surface plasmon resonance. The term "surface plasmon resonance" refers to an optical phenomenon with which it is possible to analyze biospecific interactions by detecting changes in protein concentrations with a biosensor matrix, using for example the BIAcore system (Pharmacia Biosensor AB, Uppsala, Sweden and Piscataway, N.J.). For further descriptions, see Jönsson, U. et al. (1993) *Ann. Biol. Clin.* 51:19-26; Jönsson, U. et al. (1991) *Biotechniques* 11:620-627; Johnsson, B., et al. (1995) *J. Mol. Recognit.* 8:125-131; and Johnnson, B., et al. (1991) *Anal. Biochem.* 198:268-277.

The term "$K_{off}$" describes the off rate constant for dissociation of an antibody from the antibody/antigen complex.

The term "$K_d$" describes the dissociation constant of a particular antibody-antigen interaction.

The binding affinity of the antibodies of the invention can be assessed by using standardized in vitro immunoassays such as ELISA or BIAcore analyses.

5.2 Production of Immunoglobulins 5.2.1 Production of Polyclonal Antibodies

The present invention relates to polyclonal antibodies against RGM domains and polypeptides of the invention and the production thereof.

For this purpose, a host is immunized with at least one RGM protein of the invention or derivative/equivalent thereof; and an antibody-containing serum of the host which is formed in response to the immunization is obtained.

If the RGM polypeptides to be used have only weak or no immunogenicity, their immunogenicity can be increased by coupling them to carriers, preferably a carrier protein such as keyhole limpet hemocyanin (KLH), *Limulus* Polyphenus hemocyanin (LPH), bovine serum albumin (BSA) or ovalbumin (OVA). A number of coupling possibilities are available to the skilled worker and are generally known. An expedient possibility is, for example, reaction with glutaraldehyde, for example by incubation of RGM protein with a suitable peptide or peptide mixture in water or an aqueous solvent. This reaction can conveniently be carried out at ambient temperature, usually meaning room temperature. However, cooling or gentle heating may also be expedient. The reaction usually leads to the desired result within a few hours, and a reaction time of, for example, 2 h is in the normal range. The glutaraldehyde concentration is usually in the ppm to % range, expediently from 10 ppm to 1%, preferably from 100 ppm to 0.5%. Optimization of the reaction parameters is within the scope of the skilled worker.

In addition to the antigen, the compositions ordinarily comprise further excipients, especially adjuvants normally employed for immunization, e.g. Freund's adjuvant. In particular, complete Freund's adjuvant is used for the first immunization, whereas all further immunizations are carried out with incomplete Freund's adjuvant. The immunizing cocktail is produced by adding the antigen (immunogen), preferably as component mixture described above, to the excipient(s). The antigen is usually emulsified in this case.

Suitable as host are in particular rodents or else rabbits. These or other suitable hosts are injected with the immunizing cocktail, preferably subcutaneously. The antibody titers can be determined using an immunoassay, for example competitively using a sheep antiserum directed against host IgG, and labeled RGM protein. It is thus possible to decide towards the end of the immunization whether a particular host is suitable for obtaining antibodies. If, for example, four immunizations are carried out, the antibody titer can be determined after the third immunization, and then antibodies can be obtained from animals showing a sufficient antibody titer.

Blood is preferably taken from the hosts over several weeks or months in order to obtain the antibodies formed. It is possible finally to exsanguinate the host. Serum which comprises the desired antibodies can be obtained in a manner known per se from the blood obtained in this way. The whole serum obtained in this way can if necessary be further purified in a manner known to the skilled worker, in order to concentrate the antibody fraction present therein and, in particular, the RGM protein-recognizing antibodies.

In a particular embodiment of this method, at least one antibody of the serum which specifically recognizes the RGM protein or a derivative/equivalent thereof used as immunogen is selected. Specificity means in this connection a higher binding affinity of the antibody for the immunogen than for other, in particular immunogenically related proteins.

5.2.2 Production of Monoclonal Antibodies

Immunoglobulins useful according to the invention can be obtained using methods known per se. Thus, hybridoma technology allows monospecific antibodies for an antigen of interest to be produced. In addition, recombinant antibody techniques, such as the in vitro screening of antibody libraries, have been developed and can likewise be used to produce such specific antibodies.

Thus, for example, an animal can be immunized with the antigen of interest. This in vivo approach may further comprise establishing a series of hybridomas from the lymphocytes or spleen cells of an animal, and selecting a hybridoma which secretes an antibody which specifically binds the antigen. The animal to be immunized may be for example a mouse, rat, rabbit, chicken, camelid or sheep, or a transgenic version of one of the aforementioned animals, for example a transgenic mouse with human immunoglobulin genes which makes human antibodies after an antigen stimulus. Further types of animals which can be immunized include mice with severe combined immunodeficiency (SCID) which have been reconstituted with human peripheral mononuclear blood cells (chimeric hu-PBMC-SCID mice) or with lymphoid cells or precursors thereof, as well as mice which have been treated with lethal whole-body irradiation, subsequently protected from radiation with bone-marrow cells from a mouse with severe combined immunodeficiency (SCID) and subsequently transplanted with functional human lymphocytes (the so-called trimera system). A further type of animal to be immunized is an animal (e.g. a mouse) in whose genome an endogenous gene which encodes the antigen of interest has been switched off ("knocked out"), e.g. by homologous recombination, so that this animal recognizes the antigen as foreign after immunization with the antigen. It is clear to the skilled worker that the polyclonal or monoclonal antibodies produced by these methods are characterized and selected by using known screening methods, which include ELISA techniques, but without being restricted thereto.

According to a further embodiment, a recombinant antibody library is screened with the antigen. The recombinant antibody library can be expressed for example on the surface of bacteriophages or on the surface of yeast cells or on the surface of bacterial cells. The recombinant antibody library can be for example an scFv library or an Fab library. In a further embodiment, antibody libraries can be expressed as RNA-protein fusions.

A further approach to the production of antibodies of the invention comprises a combination of in vivo and in vitro approaches. For example, the antigen can be allowed to act on the antibody repertoire by immunizing an animal with the antigen in vivo and subsequently using the antigen for in vitro screening of a recombinant antibody library produced from lymphoid cells of the animal, or a single-domain antibody library (e.g. with heavy and/or light chains). According to a further approach, the antigen is allowed to act on the antibody repertoire by immunizing an animal with the antigen in vivo and subsequently subjecting a recombinant antibody library produced from lymphoid cells of the animal or a single-domain library to an affinity maturation. According to a further approach, the antigen is allowed to act on the antibody repertoire by immunizing an animal with the antigen in vivo, subsequently selecting single antibody-producing cells which secrete an antibody of interest, and obtaining from these selected cells cDNAs for the variable region of the heavy and light chain (e.g. by PCR) and expressing the variable regions of the heavy and light chain in vitro in mammalian host cells (which is referred to as the lymphocyte-antibody selection method or SLAM for selected lymphocyte antibody method), allowing the selected antibody gene sequences to be selected and manipulated further. Monoclonal antibodies can additionally be selected by expression cloning by expressing the antibody genes for the heavy and light chain in mammalian cells, and selecting the mammalian cells which secrete an antibody having the desired binding affinity.

The present invention makes defined antigens available in the form of RGM binding domains or polypeptides for screening and counterscreening. It is thus possible according to the invention to select those polyclonal and monoclonal antibodies which show a profile of properties which is desired according to the invention as defined above.

The method of the invention for producing antibodies can be used to produce various types of antibodies. These include substantially human antibodies, chimeric antibodies, humanized antibodies and CDR graft antibodies, and antigen-binding parts thereof.

Methods for producing antibodies of the invention are described below. A distinction is made in this connection between in vivo approaches, in vitro approaches or a combination of the two.

In vivo approaches:

Starting from cells which produce the antibody generated in vivo it is possible to produce monoclonal antibodies by standardized techniques, such as the hybridoma technique originally described by Köhler and Milstein (1975, *Nature* 256:495-497) (see also Brown et al. (1981) *J. Immunol.* 127: 539-46; Brown et al. (1980) *J Biol Chem* 255:4980-83; Yeh et al. (1976) *PNAS* 76:2927-31; and Yeh et al. (1982) *Int. J. Cancer* 29:269-75). The technology for producing monoclonal antibody hybridomas is sufficiently well known (see in general R. H. Kenneth, in *Monoclonal Antibodies: A New Dimension In Biological Analyses*, Plenum Publishing Corp., New York, N.Y. (1980); E. A. Lerner (1981) *Yale J. Biol. Med.*, 54:387-402; M. L. Gefter et al. (1977) *Somatic Cell Genet.*, 3:231-36). An immortalized cell line (typically a myeloma) is for this purpose fused to lymphocytes (typically splenocytes or lymph node cells or peripheral blood lymphocytes) of a mammal immunized with the RGM protein of the invention or derivative/equivalent thereof, and the culture supernatants of the resulting hybridoma cells are screened in order to identify a hybridoma which produces a monoclonal antibody having specificity for RGM protein of the invention or for a derivative/equivalent thereof. It is possible to use for this purpose any of the many sufficiently well known protocols for fusing lymphocytes and immortalized cell lines (see also G. Galfre et al. (1977) *Nature* 266:550-52; Gefter et al. *Somatic Cell Genet.*, cited supra; Lerner, *Yale J. Biol. Med.*, cited supra; Kenneth, *Monoclonal Antibodies*, cited supra).

The skilled worker is additionally aware of many different variations of such methods, which can likewise be used. Typically, the immortalized cell lines (e.g. a myeloma cell line) were derived from the same mammalian species as the lymphocytes. It is possible for example to establish murine hybridomas by fusing lymphocytes from a mouse immunized with an immunogenic preparation of the invention with an immortalized mouse cell line. Preferred immortalized cell lines are mouse myeloma cell lines which are sensitive to culture medium comprising hypoxanthine, aminopterin and thymidine (HAT medium). Any one of many myeloma cell lines can be used in standard fashion as fusion partner, e.g. the P3-NS1/1-Ag4-1, P3-x63-Ag8.653 or Sp2/O-Ag14 myeloma line. These myeloma cell lines are obtainable from the American Type Culture Collection (ATCC), Rockville, Md. Typically, HAT-sensitive mouse myeloma cells are fused to mouse splenocytes using polyethylene glycol (PEG). The hybridoma cells resulting from the fusion are then selected using HAT medium whereby non-fused and non-productively fused myeloma cells are killed (non-fused splenocytes die after several days because they are not transformed). Monoclonal antibody-producing hybridoma cells which specifically recognize an RGM protein of the invention or a derivative/equivalent thereof are identified by screening the hybridoma culture supernants of such antibodies e.g. by using a standard ELISA assay in order to select those antibodies which are able to bind specifically the RGM protein of the invention or a derivative/equivalent thereof.

Depending on the nature of the desired antibody, various host animals can be used for the in vivo immunization. A host which itself expresses an endogenous version of the antigen of interest can be used. Alternatively, a host which has been made deficient for an endogenous version of the antigen of interest can be used. It has been shown for example that mice which have been made deficient of a particular endogenous protein by homologous recombination on the corresponding endogenous gene (i.e. knockout mice) generate a humoral response to the protein with which they have been immunized and can therefore be used to produce high-affinity monoclonal antibodies against the protein (see, for example, Roes, J. et al. (1995) *J. Immunol. Methods* 183:231-237; Lunn, M. P. et al. (2000) *J. Neurochem.* 75:404-412).

Many non-human mammals are suitable as hosts for antibody production for producing non-human antibodies against RGM protein of the invention or a derivative/equivalent thereof. These include mice, rats, chickens, camelids, rabbits and goats (and knockout versions thereof), although mice are preferred for hybridoma production. It is further possible to use a non-human host animal which expresses a human antibody repertoire for producing substantially human antibodies against a human antigen having dual specificity. Such non-human animals include transgenic animals (e.g. mice) which harbor human immunoglobulin transgenes (chimeric hu-PBMC-SCID mice) and human/mouse radiation chimeras, which are described in detail below.

According to one embodiment, the animal which is immunized with an RGM protein of the invention or derivative/equivalent thereof is a non-human mammal, preferably a mouse which is transgenic owing to human immunoglobulin genes, so that the non-human mammal makes human antibodies after an antigenic stimulus. Typically, immunoglobulin transgenes for heavy and light chain with human germline configuration are introduced into such animals, the animals having been modified so that their endogenous loci for heavy and light chain are inactive. Stimulation of such animals with antigen (e.g. with a human antigen) leads to production of antibodies which are derived from the human immunoglobulin sequences (i.e. human antibodies). Human monoclonal antibodies can be made from the lymphocytes of such animals by means of standardized hybridoma technology. For further description of transgenic mice with human immunoglobulins and their use in the production of human antibodies, see, for example, U.S. Pat. No. 5,939,598, WO 96/33735, WO 96/34096, WO 98/24893 and WO 99/53049 (Abgenix Inc.), and U.S. Pat. Nos. 5,545,806, 5,569,825, 5,625, 126, 5,633, 425, 5,661,016, 5,770,429, 5,814,318, 5,877,397 and WO 99/45962 (Genpharm Inc.); see likewise MacQuitty, J. J. and Kay, R. M. (1992) *Science* 257:1188; Taylor, L. D. et al. (1992) *Nucleic Acids Res.* 20:6287-6295; Lonberg, N. et al. (1994) *Nature* 368:856-859; Lonberg, N. and Huszar, D. (1995) *Int. Rev. Immunol.* 13:65-93; Harding, F. A. and Lonberg, N. (1995) *Ann. N.Y. Acad. Sci.* 764:536-546; Fishwild, D. M. et al. (1996) *Nature Biotechnology* 14:845-851; Mendez, M. J. et al. (1997) *Nature Genetics* 15:146-156; Green, L. L. and Jakobovits, A. (1998) *J. Exp. Med.* 188:483-495; Green, L. L. (1999) *J. Immunol. Methods* 231:11-23; Yang, X. D. et al. (1999) *J. Leukoc. Biol.* 66:401-410; Gallo, M. L. et al. (2000) *Eur. J. Immunol.* 30:534-540.

In a further embodiment, the animal which is immunized with RGM protein of the invention or a derivative/equivalent thereof can be a mouse with severe combined immunodeficiency (SCID) which has been reconstituted with human peripheral mononuclear blood cells or lymphoid cells or precursors thereof. Such mice, which are referred to as chimeric hu-PBMC-SCID mice, have been demonstrated to produce human immunoglobulin responses after an antigenic stimulus. For further description of these mice and their use for generating antibodies, see, for example, Leader, K. A. et al. (1992) *Immunology* 76:229-234; Bombil, F. et al. (1996) *Immunobiol.* 195:360-375; Murphy, W. J. et al. (1996) *Semin. Immunol.* 8:233-241; Herz, U. et al. (1997) *Int. Arch. Allergy Immunol.* 113:150-152; Albert, S. E. et al. (1997) *J. Immunol.* 159:1393-1403; Nguyen, H. et al. (1997) *Microbiol. Immunol.* 41:901-907; Arai, K. et al. (1998) *J. Immunol. Methods* 217:79-85; Yoshinari, K. and Arai, K. (1998) *Hybridoma* 17:41-45; Hutchins, W. A. et al. (1999) *Hybridoma* 18:121-129; Murphy, W. J. et al. (1999) *Clin. Immunol.* 90:22-27; Smithson, S. L. et al. (1999) *Mol. Immunol.* 36:113-124; Chamat, S. et al. (1999) *J. Infect. Diseases* 180:268-277; and Heard, C. et al. (1999) *Molec. Med.* 5:35-45.

In a further embodiment, the animal which is immunized with RGM protein of the invention or a derivative/equivalent thereof is a mouse which has been treated with a lethal whole-body irradiation, subsequently protected against radiation with bone-marrow cells from mice with severe combined immunodeficiency (SCID), and subsequently transplanted with functional human lymphocytes. This type of chimera, referred to as the trimera system, is used to produce human monoclonal antibodies by immunizing the mice with the antigen of interest, and subsequently producing monoclonal antibodies using standardized hybridoma technology. For further description of these mice and their use for generating antibodies, see, for example, Eren, R. et al. (1998) *Immunology* 93:154-161; Reisner, Y. and Dagan, S. (1998) *Trends Biotechnol.* 16:242-246; Ilan, E. et al. (1999) *Hepatology* 29:553-562; and Bocher, W. O. et al. (1999) *Immunology* 96:634-641.

In vitro approaches:

As alternative to the production of antibodies of the invention by immunization and selection, it is possible to identify and isolate antibodies of the invention by screening a recombinant combinatorial immunoglobulin library with an RGM protein of the invention or derivative/equivalent thereof in order thus to isolate members of the immunoglobulin library which bind specifically to the RGM protein or derivative/ equivalent thereof. Kits for generating and screening display libraries are commercially available (e.g. the Recombinant Phage Antibody System from Pharmacia, catalog No. 27-9400-01; and the SurfZAP® Phage Display Kit from Stratagene, catalog No. 240612). In many embodiments, the display library is an scFv library or an Fab library. The phage display technique for screening recombinant antibody libraries has been sufficiently well described. Examples of methods and compounds which can be used particularly advantageously in the generation and screening of antibody display libraries can be found for example in McCafferty et al. WO 92/01047, U.S. Pat. No. 5,969,108 and EP 589 877 (describes in particular the display of scFv), Ladner et al. U.S. Pat. Nos. 5,223,409, 5,403,484, 5,571,698, 5,837,500 and EP 436 597 (describes for example the pill fusion); Dower et al. WO 91/17271, U.S. Pat. No. 5,427,908, U.S. Pat. No. 5,580,717 and EP 527 839 (describes in particular the display of Fab); Winter et al. International Publication WO 92/20791 and EP 368,684 (describes in particular the cloning of sequences for variable immunoglobulin domains); Griffiths et al. U.S. Pat. No. 5,885,793 and EP 589 877 (describes in particular the isolation of human antibodies against human antigens using recombinant libraries); Garrard et al. WO 92/09690 (describes in particular phage expression techniques); Knappik et al. WO 97/08320 (describes the human recombinant antibody library HuCal); Salfeld et al. WO 97/29131 (describes the production of a recombinant human antibody against a human antigen (human tumor necrosis factor alpha), and in vitro affinity maturation of the recombinant antibody) and Salfeld et al. U.S. Provisional Application No. 60/126,603 and the patent applications based thereon (likewise describes the production of recombinant human antibodies against human antigen (human interleukin-12), and the in vitro affinity maturation of the recombinant antibody).

Further descriptions of screenings of recombinant antibody libraries are to be found in scientific publications such as Fuchs et al. (1991) Bio/Technology 9:1370-1372; Hay et al. (1992) Hum Antibod Hybridomas 3:81-85; Huse et al. (1989) Science 246:1275-1281; Griffiths et al., (1993) EMBO J. 12:725-734; Hawkins et al. (1992) J Mol Biol 226:889-896; Clarkson et al. (1991) Nature 352:624-628; Gram et al. (1992) PNAS 89:3576-3580; Garrad et al. (1991) Bio/Technology 9:1373-1377; Hoogenboom et al. (1991) Nuc Acid Res 19:4133-4137; Barbas et al. (1991) PNAS 88:7978-7982; McCafferty et al. Nature (1990) 348:552-554; and Knappik et al. (2000) J. Mol. Biol. 296:57-86.

As alternative to the use of bacteriophage display systems it is possible to express recombinant antibody libraries on the surface of yeast cells or bacterial cells. Methods for producing and screening libraries expressed on the surface of yeast cells are described in WO 99/36569. Methods for producing and screening libraries expressed on the surface of bacterial cells are described in detail in WO 98/49286.

As soon as an antibody of interest has been identified from a combinatorial library, the DNAs which encode the light and heavy chains of the antibody are isolated by standardized techniques of molecular biology, for example by PCR amplification of DNA from the display package (e.g. the phage) which has been isolated during the screening of the library. Nucleotide sequences of genes for light and heavy antibody chains which can be used to produce PCR primers are known to the skilled worker. Many such sequences are described for example in Kabat, E. A., et al. (1991) Sequences of Proteins of Immunological Interest, Fifth Edition, U.S. Department of Health and Human Services, NIH Publication No. 91-3242 and the database for sequences of the human germline VBASE.

An antibody or antibody part of the invention can be produced by recombinant expression of the genes for light and heavy immunoglobulin chains in a host cell. For recombinant expression of an antibody, a host cell is transfected with one or more recombinant expression vectors which harbor DNA fragments which encode the light and heavy immunoglobulin chains of the antibody, so that the light and heavy chains are expressed in the host cell and preferably secreted into the medium in which the host cells are cultivated. The antibodies can be obtained from this medium. Standardized recombinant DNA methods are used to obtain genes for heavy and light antibody chains, to insert these genes into recombinant expression vectors and to introduce the vectors into host cells. Methods of this type are described for example in Sambrook, Fritsch and Maniatis (editors), *Molecular Cloning; A Laboratory Manual, Second Edition*, Cold Spring Harbor, N.Y., (1989), Ausubel, F. M. et al. (editors) *Current Protocols in Molecular Biology*, Greene Publishing Associates, (1989) and in U.S. Pat. No. 4,816,397 of Boss et al.

As soon as DNA fragments which encode the VH and VL segments of the antibody of interest have been obtained, these DNA fragments can be further manipulated using standardized recombinant DNA techniques, for example in order to convert the genes for variable regions into genes for full-length antibody chains, into genes for Fab fragments or into an scFv gene. These manipulations lead to operative linkage of a VL- or VH-encoding DNA fragment to a further DNA fragment which encodes a further protein, e.g. a constant antibody region or a flexible linker. The term "operative linkage" is intended here to mean that the two DNA fragments are connected together in such a way that the amino acid sequences encoded by the two DNA fragments remain in the reading frame (in-frame).

The isolated DNA encoding the VH region can be, converted into a gene for a full-length heavy chain for operative linkage of the DNA encoding the VH region to a further DNA molecule encoding constant regions of the heavy chain (CH1, CH2 and CH3). The sequences of genes for constant regions of human heavy chains are sufficiently well known (see, for example, Kabat, E. A., et al. (1991) *Sequences of Proteins of Immunological Interest, Fifth Edition*, U.S. Department of Health and Human Services, NIH Publication No. 91-3242), and DNA fragments which span these regions can be obtained by standardized PCR amplification. The constant region of the heavy chain may be a constant region from IgG1, IgG2, IgG3, IgG4, IgA, IgE, IgM or IgD, with preference for a constant region from IgG1 or IgG4. A gene for an Fab fragment of the heavy chain can be obtained by operative linkage of the VH-encoding DNA with a further DNA molecule which encodes only the constant region CH1 of the heavy chain.

The isolated DNA encoding the VL region can be converted into a gene for a full-length light chain (and a gene for an Fab light chain) by operative linkage of the VL-encoding DNA with a further DNA molecule which encodes the constant region CL of the light chain. The sequences of genes of the constant region of human light chains are sufficiently well known (see Kabat, E. A., et al. (1991) *Sequences of Proteins of Immunological Interest, Fifth Edition*, U.S. Department of Health and Human Services, NIH Publication No. 91-3242), and DNA fragments which span these regions can be obtained by standardized PCR amplification. The constant region of the light chain may be a constant kappa or lambda region, with preference for a constant kappa region.

An scFv gene can be generated by operative linkage of the VH- and VL-encoding DNA fragments to a further fragment encoding a flexible linker, e.g. the amino acid sequence (Gly$_4$-Ser)$_3$, so that the VH and VL sequences are expressed as continuous single-chain protein, with the VL and VH regions being connected together by the flexible linker (see Bird et al. (1988) *Science* 242:423-426; Huston et al. (1988) *Proc. Natl. Acad. Sci. USA* 85:5879-5883; McCafferty et al., *Nature* (1990) 348:552-554).

VH and VL single domains with specificity for RGM protein of the invention or a derivative/equivalent thereof can be isolated from single-domain libraries using the methods described above. Two VH single-domain chains (with or without CH1) or two VL chains or a pair of a VH chain and a VL chain having the desired specificity can be used to bind RGM proteins of the invention or derivatives/equivalents thereof.

The recombinant antibodies or antibody parts of the invention can be expressed by inserting the DNAs which encode the partial or full-length light and heavy chains into expression vectors to result in operative linkage of the genes to transcriptional and translational control sequences. The term "operative linkage" in this connection is intended to mean that an antibody gene is ligated in a vector in such a way that transcriptional and translational control sequences within the vector fulfill their intended function of regulating the transcription and translation of the antibody gene.

The expression vector and the expression control sequences are chosen so that they are compatible with the host cell used for expression. The gene for the light antibody chain and the gene for the heavy antibody chain can be inserted into separate vectors, or both genes are inserted into the same expression vector, which is usually the case. The antibody genes are inserted into the expression vector by standardized methods (e.g. ligation of complementary restriction cleavage sites on the antibody gene fragment and vector, or ligation of blunt ends, if no restriction cleavage sites are present). The expression vector may already harbor sequences for constant antibody regions before the insertion of the sequences for the light and heavy chain. One approach for example is to convert the VH and VL sequences into full-length antibody genes by inserting them into expression vectors which already encode constant regions of heavy and light chains respectively, so that there is operative linkage of the VH segment to the CH segment(s) within the vector, and also operative linkage of the VL segment to the CL segment within the vector. An additional or alternative possibility is for the recombinant expression vector to encode a signal peptide which facilitates secretion of the antibody chain from the host cell. The gene for the antibody chain can be cloned into the vector in such a way that the signal peptide is linked in reading frame with the N terminus of the gene for the antibody chain. The signal peptide may be an immunoglobulin signal peptide or a heterologous signal peptide (i.e. a signal peptide from a non-immunoglobulin protein). In addition to the genes for the antibody chain, the expression vectors of the invention may have regulatory sequences which control expression of the genes for the antibody chain in a host cell. The term "regulatory sequence" is intended to include promoters, enhancers and further expression control elements (e.g. polyadenylation signals) which control the transcription or translation of the genes for the antibody chain. Such regulatory sequences are described for example in Goeddel; *Gene Expression Technology: Methods in Enzymology* 185, Academic Press, San Diego, Calif. (1990). The skilled worker is aware that the design of the expression vector, which includes the selection of regulatory sequences, may depend on factors such as the choice of the host cell to be transformed, the desired strength of protein expression etc. Preferred regulatory sequences for expression in mammalian host cells include viral elements which lead to strong protein expression in mammalian cells, such as promoters and/or enhancers, which are derived from cytomegalovirus (CMV) (such as the CMV promoter/enhancer), simian virus 40 (SV40) (such as the SV40 promoter/enhancer), adenovirus (e.g. the late adenovirus major promoter (AdMLP for Adenovirus Major Late Promoter) and polyoma. For further description of viral regulatory elements and sequences thereof, see, for example, U.S. Pat. No. 5,168,062 of Stinski, U.S. Pat. No. 4,510,245 of Bell et al. and U.S. Pat. No. 4,968,615 of Schaffner et al.

In addition to the genes for the antibody chain and the regulatory sequences, the recombinant expression vectors of the invention may have additional sequences such as sequences which regulate the replication of the vector in host cells (e.g. origins of replication) and selectable marker genes. The selectable marker genes facilitate the selection of host cells in which the vector has been introduced (see, for example, U.S. Pat. Nos. 4,399,216, 4,634,665 and 5,179,017, all of Axel et al.). For example, it is usual for the selectable marker gene to make a host cell into which the vector has been inserted resistant to active substances such as G418, hygromycin or methotrexate. Preferred selectable marker genes include the gene for dihydrofolate reductase (DHFR) (for use in dhfr⁻ host cells with methotrexate selection/amplification) and the neogene (for G418 selection).

For expression of the light and heavy chains, the expression vector(s) encoding the heavy and light chains is or are transfected into a host cell using standardized techniques. The various forms of the term "transfection" are intended to encompass a large number of techniques which are normally used to introduce exogenous DNA into a prokaryotic or eukaryotic host cell, e.g. electroporation, calcium phosphate precipitation, DEAE-dextran transfection and the like. Although it is theoretically possible to express the antibodies of the invention either in prokaryotic or eukaryotic host cells, expression of the antibodies in eukaryotic cells and in particular in mammalian host cells is preferred, because the probability that a correctly folded and immunologically active antibody is assembled and secreted is higher in such eukaryotic cells and especially mammalian cells than in prokaryotic cells. It has been reported that prokaryotic expression of antibody genes is inefficient for the production of large yields of active antibody (Boss, M. A. and Wood, C. R. (1985) *Immunology Today* 6:12-13).

Mammalian host cells preferred for the expression of recombinant antibodies of the invention include CHO cells (including dhfr CHO cells, which are described in Urlaub and Chasin, (1980) *Proc. Natl. Acad. Sci. USA* 77:4216-4220, and are used with a DHFR selectable marker as described for example in R. J. Kaufman and P.A. Sharp (1982) *Mol. Biol.* 159:601-621), NS0 myeloma cells, COS cells and SP2 cells. If recombinant expression vectors which encode the antibody genes are introduced into mammalian host cells, the antibodies are produced by cultivating the host cells until the antibody is expressed in the host cells or, preferably, the antibody is secreted into the culture medium in which the host cells grow. The antibodies can be obtained from the culture medium by using standardized methods for purifying proteins.

It is likewise possible to use host cells to produce parts of intact antibodies, such as Fab fragments or scFv molecules. The invention of course includes variations of the procedure described above. For example, it may be desirable to transfect a host cell with DNA which encodes either the light chain or the heavy chain (but not both) of an antibody of the invention. If light or heavy chains which are unnecessary for the binding of the antigen of interest are present, the DNA which encodes either one such light or one such heavy chain or both is partly or completely deleted by means of recombinant DNA technology. Molecules expressed by such truncated DNA molecules likewise belong to the antibodies of the invention. It is additionally possible to produce bifunctional antibodies in which one heavy and one light chain are an antibody of the invention, and the other heavy and light chain have specificity for an antigen other than that of interest, by crosslinking an antibody of the invention with a second antibody by standardized chemical methods.

In a preferred system for recombinant expression of an antibody of the invention or antigen-binding part thereof, a recombinant expression vector which encodes both the heavy antibody chain and the light antibody chain is introduced by calcium phosphate-mediated transfection into dhfr⁻ CHO cells. There is operative linkage within the recombinant expression vector of the genes for the heavy and light antibody chain in each case to regulatory CMV enhancer/Ad-MLP promoter elements in order to bring about strong transcription of the genes. The recombinant expression vector also harbors a DHFR gene which can be used to select CHO cells transfected with the vector by using methotrexate selection/amplification. The selected transformed host cells are cultivated so that the heavy and light antibody chains are expressed, and intact antibody is obtained from the culture medium. Standardized techniques of molecular biology are used in order to produce the recombinant expression vector, to transfect the host cells, to select the transformants, to cultivate the host cells and to obtain the antibody from the culture medium. Thus, the invention relates to a method for synthesizing a recombinant antibody of the invention by cultivating a host cell of the invention in a suitable culture medium until a recombinant antibody of the invention is synthesized. The method may further comprise isolating the recombinant antibody from the culture medium.

As alternative to the screening of recombinant antibody libraries by phage display, it is possible to employ further methods known to the skilled worker for screening large combinatorial libraries in order to identify the antibodies of the invention. In one type of alternative expression system, the recombinant antibody library is expressed in the form of RNA-protein fusions as described in WO 98/31700 of Szostak and Roberts, and in Roberts, R. W. and Szostak, J. W. (1997) Proc. Natl. Acad. Sci. USA 94:12297-12302. In this system, a covalent fusion is generated by in vitro translation of synthetic mRNAs which carry at their 3' end puromycin, a peptidyl acceptor antibiotic, between an mRNA and the peptide or protein which it encodes. It is thus possible to enrich a specific mRNA from a complex mixture of mRNAs (e.g. a combinatorial library) on the basis of the properties of the encoded peptide or protein (e.g. of the antibody or a part thereof), such as binding of the antibody or part thereof to RGM protein of the invention or a derivative/equivalent thereof. Nucleic acid sequences which encode antibodies or parts thereof and which are obtained from the screening of such libraries can be expressed by recombinant means in the manner described above (e.g. in mammalian host cells) and additionally be subjected to a further affinity maturation by either screening mRNA-peptide fusions in further rounds, in which case mutations are introduced into the originally selected sequence(s), or by using other methods for in vitro affinity maturation of recombinant antibodies in the manner described above.

Combinations of in vivo and in vitro approaches:

The antibodies of the invention can likewise be produced by applying a combination of in vivo and in vitro approaches, such as methods in which initially RGM protein of the invention or a derivative/equivalent thereof is allowed to act on an antibody repertoire in vivo in a host animal in order to stimulate the production of RGM protein- or derivative/equivalent-binding antibodies, and subsequently further antibody selection and/or antibody maturation (i.e. optimization) is accomplished with the aid of one or more in vitro techniques. According to one embodiment, such a combined method may comprise initially immunizing a non-human animal (e.g. a mouse, rat, rabbit, chicken, camelids, goat or a transgenic version thereof or a chimeric mouse) with the RGM protein of the invention or derivative/equivalent thereof in order to stimulate an antibody response against the antigen, and subsequently producing and screening a phage display antibody library using immunoglobulin sequences from lymphocytes which have been stimulated in vivo through the action of the RGM protein or derivative/equivalent in vivo. The first step of this combined procedure can be carried out in the manner described above in connection with in vivo approaches, whereas the second step of this procedure can be carried out in the manner described above in connection with in vitro approaches. Preferred methods for the hyperimmunization of non-human animals with subsequent in vitro screening of phage display libraries produced from the stimulated lymphocytes include those described by BioSite Inc., see, for example WO 98/47343, WO 91/17271, U.S. Pat. No. 5,427, 908 and U.S. Pat. No. 5,580,717.

According to a further embodiment, a combined method comprises initially immunizing a non-human animal (e.g. a mouse, rat, rabbit, chicken, camelids, goat or a knockout and/or transgenic version thereof, or a chimeric mouse) with an RGM protein of the invention or derivative/equivalent thereof in order to stimulate an antibody response against the RGM protein or derivative/equivalent thereof, and selecting the lymphocytes which produce the antibodies having the desired specificity by screening hybridomas (produced for example from the immunized animals). The genes for the antibodies or single-domain antibodies are isolated from the selected clones (by standardized cloning methods such as reverse transcriptase-polymerase chain reaction) and subjected to an in vitro affinity maturation in order thus to improve the binding properties of the selected antibody or of the selected antibodies. The first step of this procedure can be completed in the manner described above in connection with the in vivo approaches, whereas the second step of this procedure can be completed in the manner described above in connection with the in vitro approaches, especially by using methods of in vitro affinity maturation such as those described in WO 97/29131 and WO 00/56772.

In a further combined method, the recombinant antibodies are generated from single isolated lymphocytes by using a procedure which is known to the skilled worker as lymphocyte antibody selection method (SLAM) and is described in U.S. Pat. No. 5,627,052, WO 92/02551 and Babcock, J. S. et al. (1996) Proc. Natl. Acad. Sci. USA 93:7843-7848. In this method, a non-human animal (e.g. a mouse, rat, rabbit, chicken, camelids, goat or a transgenic version thereof, or a chimeric mouse) is initially immunized in vivo with RGM protein of the invention or a derivative/equivalent thereof in order to stimulate an immune response against the RGM protein or derivative/equivalent, and then single cells secreting antibodies of interest are selected by using an antigen-specific hemolytic plaque assay. For this purpose, the RGM protein or derivative/equivalent thereof, or structurally related molecules of interest, can be coupled to sheep erythrocytes, using a linker such as biotin, whereby individual cells which secrete antibodies of suitable specificity can be identified by using the hemolytic plaque assay. Following the identification of cells which secrete antibodies of interest, cDNAs for the variable regions of the light and heavy chains are obtained from the cells by reverse transcriptase-PCR, and these variable regions can then be expressed in conjunction with suitable constant immunoglobulin regions (e.g. human constant regions) in mammalian host cells such as COS or CHO cells. The host cells transfected with the amplified immunoglobulin sequences derived from lymphocytes selected in vivo can then be subjected to a further in vitro analysis and selection by, for example, expanding the transfected cells in order to isolate cells which express antibodies having the desired specificity. The amplified immunoglobulin sequences can moreover be manipulated in vitro.

6. Pharmaceutical Compositions 6.1 General

The present invention also relates to pharmaceutical compositions which comprise as active substance a protein of the invention (RGM protein; RGM protein-binding ligands such as anti-RGM protein antibodies) or a coding RGM protein nucleic acid sequence and, if appropriate, a pharmaceutically acceptable carrier. Pharmaceutical compositions of the invention may additionally comprise at least one additional therapeutic agent, e.g. one or more additional therapeutic agents for the treatment of one of the disorders described herein.

The pharmaceutically acceptable carriers include all solvents, dispersion media, coatings, antimicrobial agents, tonicity agents and agents delaying absorption, and the like, as long as they are physiologically compatible.

Pharmaceutically acceptable carriers include for example water, saline solution, phosphate-buffered saline solution, lactose, dextrose, sucrose, sorbitol, manitol, starch, gum arabic, calcium phosphate, alginates, tragacanth, gelatin, calcium silicate, microcrystalline cellulose, polyvinylpyrrolidone, cellulose, syrup and methylcellulose. The formulations may additionally comprise pharmaceutically acceptable carriers or conventional excipients such as lubricants, for example talc, magnesium stearate and mineral oil; wetting agents; emulsifying and suspending agents; preservatives such as methyl and propyl hydroxybenzoates; antioxidants; antiirritants; chelating agents; coating aids; emulsion stabilizers film formers; gel formers; odor-masking agents, masking flavors, resins; hydrocolloids; solvents; solubilizers; neutralizers; permeation promoters; pigments; quaternary ammonium compounds; refatting and superfatting agents; ointment, cream or oil bases; silicone derivatives; spreading aids; stabilizers; sterilizers; suppository bases; tablet excipients such as binders, fillers, lubricants, disintegrants or coatings; propellants; desiccants; opacifiers; thickeners; waxes; plasticizers; white oils. An arrangement concerning this is based on expert knowledge as set forth for example in Fiedler, H. P., Lexikon der Hilfsstoffe für Pharmazie, Kosmetik und angrenzende Gebiete, 4th edition, Aulendorf: ECV-Editio-Cantor-Verlag, 1996. Compare also Hager's Handbuch der Pharmazeutischen Praxis, Springer Verlag, Heidelberg.

The pharmaceutical compositions may be suitable for example for parenteral administration. For this purpose, the active substance such as, for example, the antibody is preferably prepared as injectable solutions with an active substance content of 0.1-250 mg/ml. The injectable solutions can be prepared in liquid or lyophilized form in a flintglass or vial, an ampoule or a filled syringe as dosage form.

The buffer may comprise L-histidine (1-50 mM, preferably 5-10 mM) and have a pH of 5.0-7.0, preferably of 6.0. Further suitable buffers include, without being restricted thereto, sodium succinate, sodium citrate, sodium phosphate or potassium phosphate buffers.

Sodium chloride can be used to adjust the tonicity of the solution to a concentration of 0-300 mM (preferably 150 mM for a liquid dosage form). Cryoprotectants can be included for a lyophilized dosage form, such as, for example, sucrose (e.g. 0-10%, preferably 0.5-1.0% (w/w)). Further suitable cryoprotectants include trehalose and lactose. Fillers can be included for a lyophilized dosage form e.g. mannitol (e.g. 1-10%, preferably 2-4% (w/w)). Stabilizers can be used both in liquid and lyophilized dosage forms, e.g. L-methionine (e.g. 1-50 mM, preferably 5-10 mM). Further suitable fillers include glycine and arginine. It is likewise possible to use surfactants, for example polysorbate 80 (e.g. 0-0.05%, preferably 0.005-0.01% (w/w)). Further surfactants include polysorbate 20 and BRIJ surfactants.

The compositions of the invention may assume a large number of forms. These include liquid, semisolid and solid dosage forms such as liquid solutions (e.g. injectable and infusible solutions, lotions, eye drops and ear drops), liposomes, dispersions or suspensions and solid forms such as oral powders, dusting powders, granules, tablets, pastilles, sachets, cachets, coated tablets, capsules such as hard and soft gelatin capsules, suppositories or vaginal pharmaceutical forms, semisolid pharmaceutical forms such as ointments, creams, hydrogels, pastes or patches. Implanted delivery devices can also be used to administer active substances of the invention. The preferred form depends on the intended mode of administration and therapeutic use. Typically, compositions in the form of injectable or infusible solutions are preferred. A suitable route of administration is, for example, parenteral (e.g. intravenous, subcutaneous, intraperitoneal, intramuscular). In a preferred embodiment, the active substance is administered by intravenous infusion or injection. According to a further preferred embodiment, the active substance is administered by intramuscular or subcutaneous injection.

Therapeutic compositions must typically be sterile and stable under the conditions of manufacture and storage. The compositions may be formulated as solution, microemulsion, dispersion, liposomal or a further ordered structure which is suitable for high active substance concentrations. Sterile injectable solutions can be produced by introducing the active compound (such as, for example, the antibody) in the required amount into a suitable solvent, if appropriate with one or a combination of the aforementioned ingredients, as required, and subsequently sterilizing by filtration. Dispersions are ordinarily prepared by introducing the active compound into a sterile vehicle which comprises a basic dispersion medium and, if appropriate, further required ingredients. In the case of a sterilized lyophilized powder for preparing sterile injectable solutions, the preferred methods of manufacture are vacuum drying and spray drying, resulting in a powder of the active ingredient and, if appropriate, further desired ingredients from a solution which has previously been sterilized by filtration. The correct flowability of a solution can be maintained by for example using a coating such as lecithin, in the case of dispersions maintaining the required particle size, or using surfactants. Prolonged absorption of injectable compositions can be achieved by incorporating an agent which delays absorption, for example monostearate salts and gelatin, into the composition.

The active substances of the invention can be administered with a large number of methods which are known to the skilled worker, although subcutaneous injection, intravenous injection or infusion represents the preferred mode of administration for many therapeutic applications. The skilled worker is aware that the route and/or mode of administration depend on the desired result. According to certain embodiments, the active compound can be prepared with a carrier which protects the compound from rapid release, for example a formulation with controlled release, including implants, transdermal patches and microencapsulated delivery systems. It is possible to use biodegradable biocompatible polymers such as ethylene-vinyl acetate, polyanhydrides, polyglycolic acid, collagen, polyorthoesters and polylactic acid. The methods for preparing such formulations are generally known to the skilled worker, see, for example, *Sustained und Controlled Release Drug Delivery Systems*, J. R. Robinson, ed., Marcel Dekker, Inc., New York, 1978.

According to certain embodiments, an active substance of the invention can be administered orally, for example in an inert diluent or an assimilable edible carrier. The active substance (and further ingredients if desired) can also be enclosed in a hard or soft gelatin capsule, compressed to tablets or added directly to food. For oral therapeutic administration, the active substances can be mixed with excipients and used in the form of swallowable tablets, buccal tablets, capsules, elixirs, suspensions, syrups and the like. If an active ingredients of the invention are to be administered by a route other than parenteral, it may be necessary to choose a coating of a material which prevents its inactivation.

The active substances of the invention can be administered together with one or more additional therapeutic agents which can be used in the treatment of the disorders described above.

The pharmaceutical compositions of the present invention ordinarily comprise a therapeutically effective amount or a prophylactically effective amount of at least one active substance of the invention. Dosage regimens can be chosen and adapted depending on the desired treatment, whether for example a therapeutic or prophylactic treatment is desired. For example a single dose, a plurality of separate doses distributed over time or a rising or decreasing dosage depending on the requirements of the therapeutic situation can be administered. It is particularly advantageous to formulate parenteral compositions in unit dosage form in order to facilitate administration and ensure a uniformity of dosage.

The treating physician is able to determine without difficulty the dosage form, mode of administration and dosage most suitable for the particular therapy and the particular active substance.

A therapeutically or prophylactically effective amount of an active substance of the invention may be for example in the range of 0.1-20 mg/kg and preferably 1-10 mg/kg, without being restricted thereto. It is, of course, possible for these amounts to vary depending on the nature and severity of the condition to be alleviated.

6.2 Vaccines

The RGM proteins of the invention and derivatives/equivalents thereof can be used as immunogen for vaccination of a patient to be treated.

Vaccines which can be used for this purpose generally represent a pharmaceutical composition which comprises at least one RGM protein of the invention and/or at least one derivative/equivalent of the invention thereof. The composition may additionally comprise a physiologically tolerated carrier and, if appropriate, further excipients, for example immunostimulants.

Whereas suitable carriers can in principle be chosen as desired, the nature of the carrier is generally governed by the route of administration. Thus, the vaccines of the invention can be formulated in particular in a form suitable for parenteral, for example intravenous, intramuscular and subcutaneous, administration. In these cases, the carrier preferably comprises water, saline solution, alcohol, a fat, a wax and/or a buffer.

It is possible to use any one of a large number of immunostimulants in the vaccines of the invention. For example, an adjuvant can be included. Most adjuvants comprise a substance which is intended to protect the antigen from rapid degradation, such as aluminum hydroxide or a mineral oil, and a protein derived from lipid A, *Bordetella pertussis* or *Mycobacterium tuberculosis*. Suitable adjuvants are usually commercially available, for example complete or incomplete Freund's adjuvant; AS-2; aluminum salts such as aluminum hydroxide (if appropriate as gel) or aluminum phosphate; calcium, iron or zinc salts; an insoluble suspension of acylated tyrosine; acylated sugars; cationically or anionically derivatized polysaccharides; polyphosphazenes; biodegradable microspheres; monophosphoryl-lipid A. Cytokines such as GM-CSF or interleukin-2, -7 or -12 can likewise be used as adjuvants.

7. Therapeutic Methods 7.1. Treatment of Neuronal Disorders

It has been disclosed in the prior art that an accumulation of RGM protein is to be observed at the site of the lesion in cases of injuries to the central nervous system (cf. Schwab et al. loc. cit.). At the same time, renewed outgrowth of the injured nerve fibers is prevented thereby. This harmful effect on nerve fiber growth is mediated by binding of RGM to the receptor molecule neogenin. Modulation, in particular inhibition, of the interaction between RGM and the receptor molecule neogenin would therefore be suitable to suppress the inhibitory activity of RGM on nerve fiber growth.

7.2. Treatment of Neoplastic Diseases

There have long been indications suggesting that neogenin might be causally connected with the development and/or progression of neoplastic diseases. Thus, for example, Meyerhardt et al. reported in Oncogene (1997) 14, 1129-1136, that neogenin was detectable in more than 50 investigated cancer cell lines, including glioblastoma, medulloblastoma, neuroblastoma cell lines, and cell lines from colorectal, breast, pancreatic and cervical carcinomas. Overexpression of neogenin was additionally observed in esophageal cancer cell lines (Hue et al., *Clinical Cancer Research* (2001) 7, 2213-2221). A systematic investigation of the expression profiles of 3588 genes in 211 lung adenocarcinoma patients has recently provided a further indication of the involvement of neogenin in the development and progression of the neoplastic disease (Berrar et al., *J. Comput. Biol.* (2005) 12 (5), 534-544).

Since it is additionally known that RGM exhibits a potential tumor-promoting effect in that it can prevent cell death through binding to the tumor cell-associated neogenin receptor (Matsunaga et al. Nature Cell Biol. 6, 749-755, 2004), a new therapeutic approach to the treatment of neoplastic diseases might be created by modulating the RGM-neogenin interaction, in particular by interrupting this interaction with the aid of specific anti-RGM antibodies.

7.3. Treatment of Iron Metabolism Disorders

RGM C, also called hemojuvelin, is of essential importance for iron metabolism in the human and animal body. Juvenile hemochromatosis is a hereditary, relatively rare iron metabolism disorder which is manifested by an iron overload in the body. This disorder is caused by mutations in the hemojuvelin molecule (cf. Huang et al., *The Journal of Clinical Investigation* (2005), 115, 2087-2091). The administration of functional RGM proteins of the invention or the active domains thereof therefore represents a useful therapeutic approach to alleviating such iron metabolism disorders.

7.4. Promotion of Bone Tissue Formation

There are indications in the prior art that one member of the RGM family of proteins, specifically RGM B, also known under the designation DRAGON, is involved in bone morphogenesis. Thus, for example, Samad et al. describe in *JBC Papers in Press*, edition of Jan. 25, 2005, the interaction between DRAGON and the type I and type II receptors of bone morphogenetic protein (BMP). A bone growth-promoting effect and thus a new therapeutic approach to the treatment of disorders with impaired bone growth or of bone injuries is therefore conceivable by administering RGM polypeptides of the invention.

8. Diagnostic Methods

Diagnostic agents which should be mentioned according to the invention are in particular RGM protein and derivatives/equivalents as defined above, and antibodies directed against them.

The present invention therefore makes it possible in particular to determine, with qualitative or quantitative improvement, the pathological states defined above by detecting disease-typical antigens or antibodies.

The determination preferably takes place using immunological methods. This is possible in principle with any analytical or diagnostic test method in which antibodies are employed. These include agglutinations and precipitation techniques, immunoassays, immunohistochemical methods and immunoblotting techniques, e.g. Western blotting or dot-blot methods. Also included are in vivo methods, for example imaging methods.

Use in immunoassays is advantageous. Those suitable are both competitive immunoassays, i.e. antigen and labeled antigen (tracer) compete for the antibody binding, and sandwich immunoassays, i.e. the binding of specific antibodies to the antigen is detected using a second, usually labeled antibody. These assays may be either homogeneous, i.e. without separation into solid and liquid phase, or heterogeneous, i.e. bound labels are separated from unbound ones, for example by solid phase-bound antibodies. The various heterogeneous and homogeneous immunoassay formats can be assigned to particular classes depending on the labeling and method of measurement, for example RIAs (radioimmunoassays), ELISA (enzyme linked immunosorbent assay), FIA (fluorescence immunoassay), LIA (luminescence immunoassay), TRFIA (time-resolved FIA), IMAC (immunactivation), EMIT (enzyme multiplied immune test), TIA (turbidimetric immunoassay), I-PCR (immuno-PCR).

Competitive immunoassays are preferred for the antigen determination of the invention. In this case, labeled antigen (tracer) competes with the antigen of the sample to be quantified for binding to the antibody used. The amount of antigen, that is the amount of antigen, in the sample can be determined from the amount of displaced tracer with the aid of a standard curve.

Of the labels available for these purposes, enzymes have proved to be advantageous. For example, it is possible to use systems based on peroxidases, especially horseradish peroxidase, alkaline phosphatase and β-D-galactosidase. Specific substrates are available for these enzymes, and their conversion can be followed for example by photometry. Suitable substrate systems are based on p-nitrophenyl phosphate (p-NPP), 5-bromo-4-chloro-3-indolyl phosphate/nitro blue tetrazolium (BCIP/NPT), fast red/naphthol-AS-TS phosphate for alkaline phosphatase; 2,2-azinobis(3-ethylbenz-thiazoline-6-sulfonic acid) (ABTS), o-phenylenediamine (OPD), 3,3',5,5'-tetramethylbenzidine (TMB), o-dianisidine, 5-aminosalicylic acid, 3-dimethylaminobenzoic acid (DMAB) and 3-methyl-2-benzothiazolinone hydrazone (MBTH) for peroxidases; o-nitrophenyl β-D-galactoside (o-NPG), p-nitrophenyl β-D-galactoside and 4-methylumbellifer β-D-galactoside (MUG) for p-D-galactosidase. These substrate systems are in many cases commercially available in a form ready for use, for example in the form of tablets, which may also comprise further reagents such as expedient buffers and the like.

The coupling of labels to peptides or antibodies to prepare tracers can take place in a manner known per se. In addition, a number of labels expediently modified for conjugation to proteins are available, for example biotin-, avidin-, extravidin- or streptavidin-conjugated enzymes, maleimide-activated enzymes and the like. These labels can be reacted directly with the molecule to be used according to the invention.

If a heterogeneous immunoassay format is chosen, the antigen-antibody complex can, for the purpose of separation, be bound to the support for example via an anti-idiotype antibody, e.g. an antibody directed against rabbit IgG, coupled to the support. Supports, especially microtiter plates, which are coated with appropriate antibodies are known and commercially available.

The present invention further relates to immunoassay sets with at least one antibody described above and further components. This comprises a collection, usually as pack unit, of means for carrying out a determination of the invention. To maximize the simplicity of use, these means are preferably provided substantially ready for use. An advantageous arrangement is provided by the immunoassay in kit form. A kit usually comprises a plurality of containers for separate arrangement of components. All the components can be provided in dilution ready for use, as concentrate for dilution or as dry substance or lyophilizate for dissolving or suspending; single components or all the components may be frozen or be stored at ambient temperature until used. Sera are preferably shock-frozen, for example at −20° C., so that in these cases an immunoassay must be kept preferably at freezing temperatures before use.

Further components added to the immunoassay may be: standard protein, tracer; control serum, microtiter plates, preferably coated with antibody, buffer, for example for testing, for washing or for reacting the substrate, and the enzyme substrate itself.

General principles of immunoassays and the generation and use of antibodies as laboratory and clinical aids are to be found for example in Antibodies, A Laboratory Manual (Harlow, E., and Lane, D., Ed., Cold Spring Harbor Laboratory, Cold Spring Harbor, N.Y., 1988).

9. Screening Methods

The invention also relates to methods for detecting effectors of the RGM receptor neogenin, where a sample in which an effector is suspected is incubated with an RGM protein or polypeptide, and the mixture is investigated for the formation of an effector-RGM protein complex.

Such effectors may have an agonistic, partial agonistic, antagonistic or inverse agonistic effect. They may be for example synthetic low molecular weight substances, synthetic peptides, natural or synthetic antibody molecules or natural substances.

Such methods of the invention are usually carried out as in vitro screening methods with which it is possible to select from a large number of different substances those which appear to be most promising in relation to future use.

For example, extensive substance libraries comprising a large number of potential active substances can be set up by means of combinatorial chemistry. Screening of combinatorial substance libraries for substances having a desired activity can be automated. Robot screening devices are used for efficient evaluation of the individual assays arranged preferably on microtiter plates. Thus, the present invention also relates to screening methods, i.e. both primary and secondary screening methods, in which preferably at least one of the methods described below is used. If a plurality of methods is used, this is possible sequentially or simultaneously on one and the same sample or on different samples of a substance to be investigated.

An efficient technique for carrying out such methods is the Scintillation Proximity Assay, abbreviated to SPA, which is known in the area of active substance screening. Kits and components for carrying out this assay can be purchased commercially, for example from Amersham Pharmacia Biotech. In principle, solubilized or membrane-bound receptors are immobilized on small fluoromicrospheres comprising scintillant. If, for example, a radioligand binds to the immobilized receptors, the scintillant is excited to emit light because the scintillant and radioligand are in spatial proximity.

A further efficient technique for carrying out such methods is the FlashPlateR technique known in the area of active substance screening. Kits and components for carrying out this assay can be purchased commercially, for example from NEN Life Science Products. This principle is likewise based on microtiter plates (96- or 384-well) which are coated with scintillant.

The present invention likewise relates to the substances or parts of substance mixtures which can be identified by these methods.

The invention is now explained in more detail with reference to the following nonlimiting preparation and use examples Experimental Section 1. General Information Assay Method 1: Demonstration of the Effect of RGM Peptides in Neuronal Outgrowth Tests with Rat Cortical Neurons The effect of RGM peptides in vitro was investigated by carrying out neuronal outgrowth tests. For this purpose, rat cortical neurons were prepared using the following media:

Stock medium per liter: 90 ml GB5, 100 ml Minimum Essential Medium-Eagle (10×; Gibco, order No.: 21430.020), ad 1000 ml with Millipore water. pH 7.0, 280-310 mosm.

GB5 per liter: 26.6 g $NaHCO_3$, 44.4 g glucose, sterilized by filtration.

Plating medium (PM) per liter: 0.8 mM glutamine, 100 ml of heat-inactivated fetal calf serum (FCS), 100 ml of heat-inactivated horse serum, ad 1000 ml with stock medium Maintenance medium (MM) per liter: 0.8 mM glutamine, 100 ml of heat-inactivated horse serum, ad 1000 ml with stock medium Trypsin solution: 0.1% trypsin, 0.04% EDTA in PBS without calcium/magnesium, sterilized by filtration.

Cortical neurons were obtained by sacrificing pregnant rats by cervical dislocation, opening the abdominal cavity thereof, removing the uterus with the embryos (embryonic day 18 (E18)) and washing in PBS. Microdissection scissors were used to cut open the uterus longitudinally, and the embryos were removed and exposed. The embryos were sacrificed by throat-cutting, the brain was removed and the forebrain cortex was dissected. The cortices are incubated each in 1 ml of a 0.1% strength trypsin solution at 37° C. for 5 minutes, the reaction is stopped with maintenance medium (MM) and, after incubation in a total of 10 ml of MM for 5 minutes, triturated with fire-polished Pasteur pipettes with decreasing orifice diameter. The cell suspension was centrifuged at 1200 rpm for 10 minutes, and the supernatant was aspirated off and discarded. The cell pellet was taken up in 8 ml of MM and cautiously resuspended. The cells were counted in a Neubauer counting chamber, and the number of cells was adjusted to about 400 000 cells/0.2 ml in MM and preaggregated. For this purpose, 200 μl of the cell suspension per well were put on glass chamber slides (LabTek, order No. 177402) and incubated at 37° C. for 24 h. Aggregates of neurons form during this. 10-80 μl of these aggregates were plated out in each well of a poly-D-lysine-coated 96-well plate (e.g. Becton Dickinson Biocoat 96-well black plate #354640) and made up where appropriate with MM to 70-90 μl. After 1 h, the RGM peptides were added in various concentrations in a volume of 10 μl and made up to 100 μl where appropriate with MM. 24-48 h later, the axonal outgrowths were initially assessed by examination under a light microscope, and the cultures were then fixed by adding 100 μl of 4% paraformaldehyde solution and stored at 4° C. for at least 12 hours. All the steps for preparing the tubulin cytoskeleton by immunofluorescent staining, with the exception of the incubation with the primary antibody, took place at room temperature. The wells were washed once with 100-300 μl of PBS for 5-15 minutes and then the cells were permeabilized by incubating in 100 μl of 0.1% Triton X-100 for 10-20 min. The wells were washed twice with 300 μl of PBS for 5-15 minutes and then incubated with 100 μl of 1% bovine serum albumin solution in PBS for 60 minutes. The primary antibody (e.g. Sigma, monoclonal anti-β-tubulin isotype III clone SDL 3D10, #T8660; Abcam, TuJI #ab14545) was diluted 1:1000 in 1% bovine serum albumin solution in PBS and incubated 50 μl per well at 4° C. overnight. The wells were washed three times with 100-300 μl of PBS for 5-15 minutes. The fluorescence-labeled secondary antibody (Jackson ImmunoResearch, Cy3 conjugated Affinity Pure Donkey Anti Mouse #715-165-151) was diluted 1:500 in 1% bovine serum albumin solution in PBS, which additionally comprised 0.5 μg/ml bisbenzimide (H33258) to visualize the cell nuclei, and 50 μl of this dilution were incubated per well at room temperature for 1-2 h or at 4° C. overnight. The wells were washed twice with 100-300 μl of PBS for 5-15 minutes, the PBS was aspirated off, and one drop (approx. 50 μl) of Fluoromount G (Southern Biotechnology Associates Inc#010001) were added to each well. Images were recorded in an inverse fluorescence microscope (Zeiss, Axiovert 200 M), detecting in each case the fluorescence of the labeled secondary antibody and the bisbenzimide fluorescence. The area covered by the two fluorescences was ascertained with the aid of an image analysis program (Media Cybernetics, Image-Pro Plus). To ascertain the axon growth index (AG-I), the difference in area between secondary antibody stain (staining of the outgrown axons and of the cell aggregates) and the bisbenzimide stain (staining of the cell aggregates) was formed and divided by the area of the bisbenzimide stain. This index therefore represents a measure of the area covered by axons in relation to the size of the cell aggregates.

Assay Method 2: Demonstration of the Effect of RGM Peptides in Neuronal Outgrowth Tests with Cortical Human Neurons The human pluripotent carcinoma cell line Ntera (DSMZ ACC527) is an established cell culture model. In this case, axons grow out of cell aggregates and form a corona of axons around the respective aggregate.

For this purpose, $2.5 \times 10^6$ Ntera cells were seeded in a 175 $cm^2$ bottle and differentiated in 10 μM retinoic acid (Sigma)

(medium: D-MEM (Gibco/Invitrogen 31966-021), 10% fetal calf serum, 100 u/ml penicillin, 100 μg/ml streptomycin (both Gibco/Invitrogen)) for 3 weeks. Differentiated cells were then divided 1:6 in new bottles and cultured without retinoic acid for a further 2 days. Neuronal cells adhering to the resulting cell lawn were detached by capping and aggregated by slow shaking in Neurobasal medium (Neurobasal Medium (Gibco/Invitrogen 21103-049), 2 mM L-glutamine (Gibco/Invitrogen 25030-024), 100 u/ml penicillin, 100 μg/ml streptomycin (both Gibco/Invitrogen) in a shaken flask overnight (in an incubator).

The next day, Ntera aggregates were seeded in poly-D-lysine and laminin (Sigma) (10 μg/ml) 96-well plates (Biocoat Poly-D-Lysine Cellware 96-Well Black/Clear Plate (Becton Dickinson #35 6640). The inhibitory effect of RGM peptides and fragments was analyzed by adding various concentrations of the substances to be tested.

Assay Method 3: RGM A—Neogenin Binding Assay:
a) Materials:
  Immuno plate: Cert. Maxi Sorp F96 (NUNC, 439454)
  Recombinant human RGM A, R&D Systems; Prod.#2495-RM (260 μg/ml)
  Recombinant human neogenin Fc, Abbott; Ludwigshafen (ALU 1514/122; 425 μg/ml)
  Peroxidase-conjugated, affinity-purified mouse anti-human IgG Fc fragment Ab (Jackson Immuno Research, Code: 209-035-098 (0.8 mg/ml))
  Developer substrates: immuno Pure TMB Substrate Kit (Pierce, #34021)
  Sulfuric acid (Merck, #4.80354.1000)
b) Method:
1. RGM A binding to immuno plate:
  2.5 μg/ml RGM A (R&D) in 50 mM $Na_2CO_3$ (50 μl/well)
  Incubation at 37° C. for 1 h
2. Washing step:
  Wash 3× with PBS/0.02% Tween 20 (100 μl/well)
3. Blocking of nonspecific binding sites
  Blocking with 3% BSA in PBS/0.02% Tween (200 μl/well)
  Incubation at 37° C. for 1 h
4. Neogenin binding:
  Addition of neogenin in dilutions (initial conc. 1 μg/ml) in 1% BSA PBS/0.02% Tween
  Incubation at 37° C. for 1 h
5. Washing step:
  Wash 3× with PBS/0.02% Tween 20 (100 μl/well)
6. Antibody detection of the bound neogenin:
  Addition of HRP-coupled mouse anti-human IgG Fc fragment Ab (diluted 1:2500 in PBS/1% BSA) (50 μl/well)
  Incubation at 37° C. for 1 h
7. Washing step:
  Wash 3× with PBS/0.02% Tween 20 (100 μl/well)
8. Development
  Addition of 50 μl/well of the developing substrate (Immuno Pure TMB substrate, Pierce)
  Incubation, room temperature, 1-30 min
  Stop reaction with 50 μl of 2.5M $H_2SO_4$/well 2. Preparation Examples Preparation Example 1

Preparation of RGM a Protein Fragments in Mammalian Cells

To characterize the active RGM A domain in axon growth and neogenin binding assay methods, RGM A (AA 168-422) and RGM A fragments 70-80 AA in size (Frag. 1: 169-238; Frag. 2: 218-284; Frag. 3: 266-335; Frag. 4: 316-386; Frag. 5: 369-238; and Frag. 6: (168-422)) was expressed in mammalian cells (HEK293) as AP fusion proteins.

For this purpose, the DNA coding for the respective fragment was cloned into the vector pDEST AP/ccdb/Myc/His (Invitrogen, Gateway Vektor System) (AP—alkaline phosphatase; PPC—PreScisson protease). The DNA coding for the respective fragment region was for this purpose amplified by PCR from the RZPD clone (clone AL136826 (DKFZp434D0727); published RZPD sequence: BC015886, AL136826)). The following oligonucleotides were employed to do this:

```
Fragment 169-238:
                                               (SEQ ID NO: 11)
GGGGACAAGTTTGTACAAAAAAGCAGGCTTTCTGGAAGTTCTGTTCCAGGGGCCCCCACA
CCTCAGGACTTTCACCGAC
                                               (SEQ ID NO: 12)
GGGGACCACTTTGTACAAGAAAGCTGGGTGCTCGTCCATCTCAGCCTGGTACACC Fragment 218-284:
                                               (SEQ ID NO: 13)
GGGGACAAGTTTGTACAAAAAAGCAGGCTTTCTGGAAGTTCTGTTCCAGGGGCCCATCATC
TTCAAGAACTTCCAGGAGTGTG
                                               (SEQ ID NO: 14)
GGGGACCACTTTGTACAAGAAAGCTGGGTGGCGCACCACGATGGTGGTG Fragment 316-386
                                               (SEQ ID NO: 15)
GGGGACAAGTTTGTACAAAAAAGCAGGCTTTCTGGAAGTTCTGTTCCAGGGG
CCCTCAGGCCAGCACGTGGAGATCC
                                               (SEQ ID NO: 16)
GGGGACCACTTTGTACAAGAAAGCTGGGTCCTCAGCATTGGTGTGGAAGGCC Fragment 266-335
                                               (SEQ ID NO: 17)
GGGGACAAGTTTGTACAAAAAAGCAGGCTTTCTGGAAGTTCTGTTCCAGGGGCCCCTGCG
GGGCTGCCCCCTC
                                               (SEQ ID NO: 18)
GGGGACCACTTTGTACAAGAAAGCTGGGTCGCCCGTGGTGAGGAGGTCG
```

-continued

Fragment 368-422

(SEQ ID NO: 19)
GGGGACAAGTTTGTACAAAAAAGCAGGCTTTCTGGAAGTTCTGTTCCAGGGGCCC
CTGCCGGTGGAGGACCTGTAC (SEQ ID NO: 20)
GGGGACCACTTTGTACAAGAAAGCTGGGTTGCCTGGCAGGTCCCGAGTC

Fragment 169-422

(SEQ ID NO: 21)
GGGGACAAGTTTGTACAAAAAAGCAGGCTTTCTGGAAGTTCTGTTCCAGGGGCCC
CCACACCTCAGGACTTTCACCGAC (SEQ ID NO: 22)
GGGGACCACTTTGTACAAGAAAGCTGGGTTGCCTGGCAGGTCCCGAGTC

The resulting PCR products was cloned by specific recombination (attLxattR) into the vector pDEST AP/ccdb/Myc/His, and the correct sequence was checked by sequencing.

HEK293 cells (ATCC CRL 1573) were transfected with the plasmids. To do this, cells were seeded at a density of 80% in 15 cm plates on the day before the transfection. The next day, DNA was mixed with Lipofectamine 2000 (Invitrogen) in accordance with the manufacturer's protocol, and the cells were incubated therewith for 12 h. After culturing under selective culturing conditions (D-MEM (Gibco/Invitrogen 31966-021), 10% fetal calf serum, 100 u/ml penicillin, 100 µg/ml streptomycin (both Gibco/Invitrogen), 150 µg/ml zeocin/invitrogen) for a further four weeks, stably expressing clones were selected by detection of alkaline phosphatase in the growth medium.

For protein production, stably expressing cells were amplified in growth medium and, when a confluence of 70% was reached, transferred into production medium (Pro293 medium (BioWhittaker/Cambrex, 12-764Q), 2 mM glutamine (Invitrogen)). After culturing for a further 4 days, the production medium was harvested, separated from cell debris and concentrated by membrane concentrators (Vivaspin30).

The expressed AP-RGM fusion proteins were then purified from the supernatants by Ni-chelate affinity chromatography. For this purpose, Ni-NTA-agarose (Qiagen) was equilibrated in buffer A (50 mM HEPES-KOH, 100 mM NaCl, 10% glycerol, 10 mM imidazole). The concentrated supernatant was then incubated with the Ni-NTA-agarose with rotation at 4° C. for 1 h. Washing three times of the Ni-NTA-agarose which was removed by centrifugation was followed by elution of bound protein with elution buffer (buffer A with 250 mM imidazole).

Analysis of the proteins took place with the aid of dot-blot, SDS-PAGE and Western blot analyses. The concentration was determined by Bradford protein determination and ELISA measurement of the AP concentration.

3. Exemplary Embodiments

Exemplary Embodiment 1

Fragment Analysis with Neogenin-Expressing HEK293 Cells a) General:

It was previously known that the active, growth-inhibiting activity of the RGM A protein from chickens is located in the region between amino acid position 150 and 350.

Fragments of the human RGM A protein which cover this range were therefore prepared. HEK293 cells which carry the RGM receptor endogenously on their surface were then transfected with these fragments in order to prepare clonal cell cultures which produce the individual protein fragments and release them into the culture medium. All the fragments were produced as fusion proteins with attached alkaline phosphatase enzyme. The presence of the active domain in these cells should make itself noticeable by: less cellular proliferation, increased cell death and/or altered cell-substrate adhesion.

Increased cell death and less proliferation have, of course, a direct effect on the produced amount of the active fragment. The amount of the produced fragments was assessed with the aid of a semiquantitative dot-blot assay.

b) Procedure:

The RGM A fragments prepared as in preparation example 1 were introduced into HEK293 cells. Stably transfected cells were cultured to confluence in culture medium (D-MEM (Gibco/Invitrogen 31966-021), 10% fetal calf serum, 100 u/ml penicillin, 100 µg/ml streptomycin (both Gibco/Invitrogen), 150 µg/ml zeocin (Invitrogen). Subsequently, 1 ml portions of the culture supernatant were filtered through a nitrocellulose membrane (Sartorius) in a slot-blot chamber. AP-RGM fusion proteins immobilized on the membrane were detected by detecting the alkaline phosphatase activity by incubating the nitrocellulose membrane with NBT/BCIP substrate (Roche). The produced amount of the active fragment was determined with the aid of a semiquantitative dot-blot assay.

On the basis of this assay, the stable cell clones were divided into the following categories:
strongly producing cell clones (S producer)
moderately strongly producing clones
weakly producing clones
non-producing clones (0 producer).

In addition, the ratio of strongly to non-producing clones was determined.

c) Result:

The following values were found for the individual RGM A fragments assayed:

| Fragment (amino acid positions) | Ratio "S producer" versus "0 producer" | Proportion of strongly producing cell clones [%] |
|---|---|---|
| 1 (169-238) | 2.3 | 40 |
| 2 (218-284) | 0.5 | 17 |
| 3 (266-335) | 0.16 | 6.2 |
| 4 (316-386) | 0.5 | 16 |
| 5 (369-422) | 0.63 | 16 |
| 6 (168-422) | 0.16 | 9 |

Fragments 3 and 6 in particular showed a pronounced activity in this assay.

Exemplary Embodiment 2

Investigation of Synthetic RGM a Peptides in the Nerve Fiber Growth Assay

For this purpose, the following RGM A peptides were synthesized and assayed in various concentrations in the nerve fiber growth assay described above (assay method 1 and assay method 2):

Peptide 1: AA 267-285
Peptide 2: AA 308-325
Peptide 3: AA 358-377
Peptide 4: AA 378-400
(Numbering based on SEQ ID NO: 2)

Of the peptides assayed to date, peptide 1 reliably and reproducibly showed inhibitory activity. It can therefore be assumed that peptide 1 (AA 267-285) forms part of the active domain of the RGM protein.

The test results are depicted in FIGS. 3 A, B, C and 4 A, B.

Figure 3C:
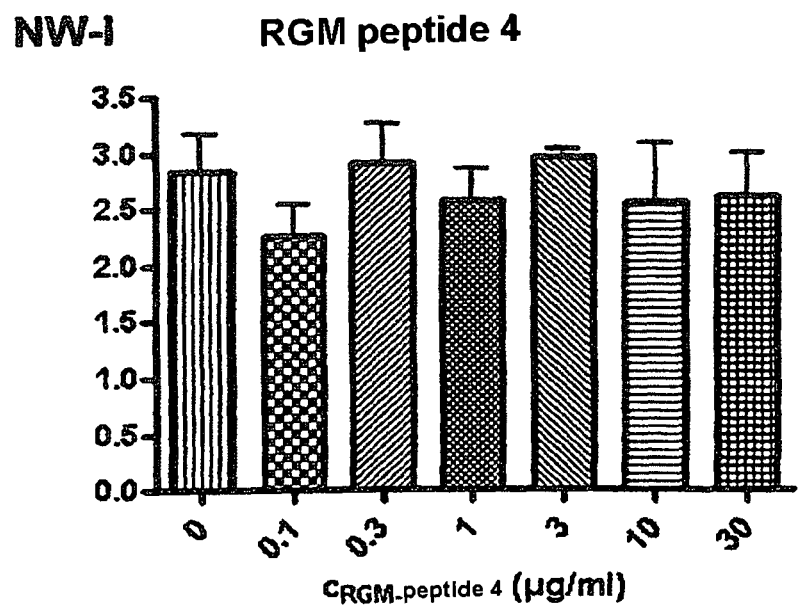
FIG. 3A shows by means of fluorescence micrographs the influence of various RGM A peptide fragments on nerve fiber growth of rat neuronal cells. Whereas peptide 1 shows inhibitory activity at a concentration of 10 µg/ml, peptide 4 is inactive at the same concentration. Corresponding control mixtures with buffer or PBS is shown for comparison.

FIG. 3A shows that, in contrast to peptide 4, peptide 1 significantly inhibits nerve fiber growth in a concentration of 10 μg/ml in tests with rat neuronal cells (assay method 1). FIG. 3B illustrates the effect of different concentrations (0 to 30 μg/ml) of peptide 1 on nerve fiber growth of cortical neurons. A significant inhibitory activity is detectable at a concentration of more than 3 μg/ml and above. In contrast thereto, peptide 4 shows no activity under the same conditions (cf. FIG. 3C) (AG-I=axon growth index, corresponds to the total area of the neuronal aggregate with the relevant axons minus the area of the aggregate.

FIG. 4A shows that peptide 1, but not peptide 4, significantly inhibits nerve fiber growth of human Ntera cells in a concentration of 30 μg/ml (assay method 2). FIG. 4B illustrates the statistical significance of the observed inhibitory effect of peptide 1.

Exemplary Embodiment 3

Investigation of Synthetic RGM a Fragments in the Nerve Fiber Growth Assay

The six different RGM A fragments prepared as in preparation example 1 and listed again in the following were assayed for inhibitory activity in the axon growth assay (cf. above assay method 2) with human Ntera nerve cells.
Fragment 1: amino acids 169-238
Fragment 2: amino acids 218-284
Fragment 3: amino acids 266-335
Fragment 4: amino acids 316-386
Fragment 5: amino acids 369-422
Fragment 6: amino acids 168-422
(Numbering in each case based on SEQ ID NO: 2)

Figure 5A:
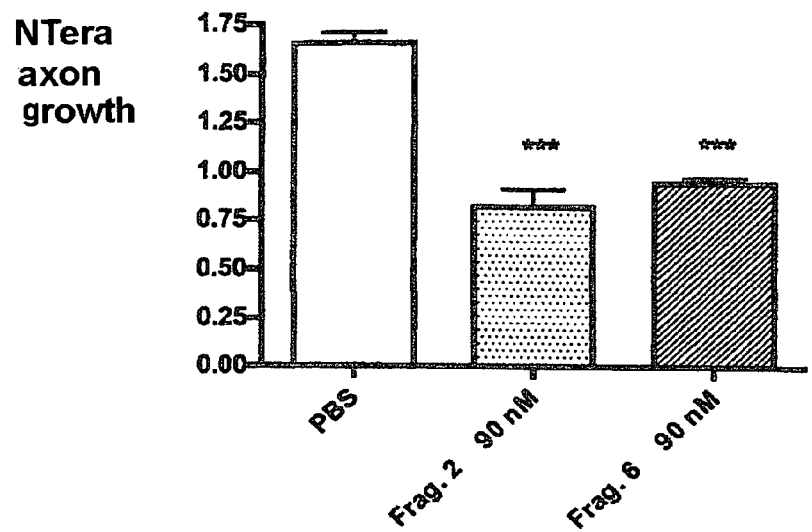
FIG. 5A shows the results of an analysis of RGM A fragments in NTera nerve fiber growth assay. Both the RGM A fragments 2 (218-284) and 6 (168-422) were added in a concentration of 90 nM to NTera neurons. Both fragments strongly inhibit the nerve fiber growth of the NTera neurons. ***=$p<0.001$ significance versus PBS control.
Figure 5B:
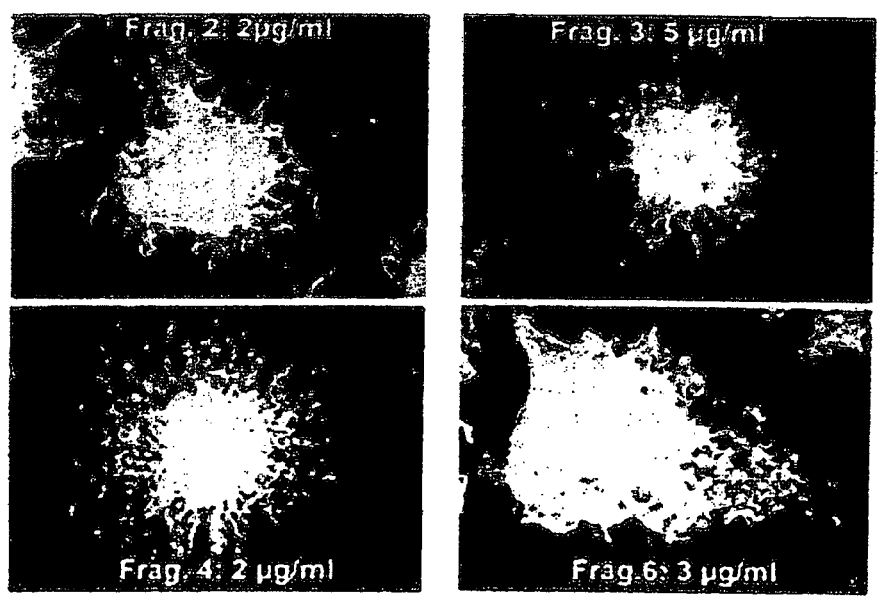
FIG. 5B shows fluorescence micrographs of the assay results on RGM A fragments in the NTera nerve fiber growth assay. The RGM A fragments 2 (218-284), 3 (266-335), 4 (316-386) and 6 (168-422) were pipeted in the stated concentrations to NTera neurons. The active, meaning inhibitory for axon growth, fragments were 2, 3 and 6, but fragment 4 was inactive.
Figure 5C:
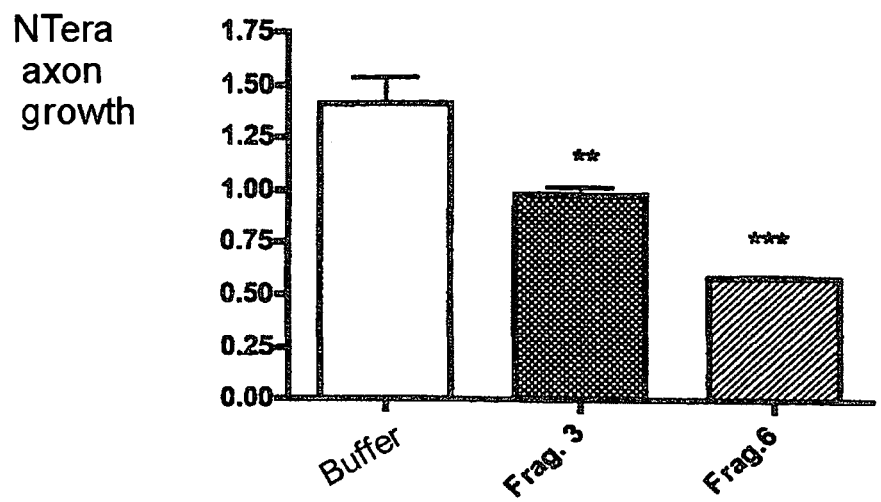
FIG. 5C shows further results of the analysis of RGM A fragments in the NTera nerve fiber growth assay. Both the RGM A fragments 3 (286-335) and 6 (168-422) were added in a concentration of 6 µg/ml to NTera neurons. Both fragments strongly inhibit nerve fiber growth of the NTera neurons. =$p<0.01$ significance versus buffer control, *=$p<0.001$ significance versus buffer control.

The results are summarized in appended FIGS. 5A, B and C.

In total, 6 different RGM A fragments were assayed in the NTera outgrowth assay. Fragments 2, 3 and 6 were active, while fragments 1, 4 and 5 were inactive.

Fragment 6 corresponds to the active, completely processed RGM A protein as has also been described in vivo. It follows from these data that an important nerve fiber growth-inhibitory domain of the human RGM A protein is located in the region of fragments 2 and 3, i.e. between amino acids 218 and 335. In order to characterize this inhibitory domain more accurately, therefore, short RGM A peptides from the regions of fragments 2 and 3 are assayed in a next step.

Exemplary Embodiment 4

Investigation of Synthetic RGM a Peptides in the Nerve Fiber Growth Assay

The peptides shown in the following table were assayed in the axon growth assay (cf. above assay method 2).

TABLE

| Neighboring RGM A peptides from peptide 1 were synthesized and employed in the axon growth assay | |
|---|---|
| Peptide 1 (267-285) | GQHVEIQAKYIGTTIVVRQ (SEQ ID NO: 8) |
| Peptide Down-1 (260-275) | KITEKVSGQHVEIQAK (SEQ ID NO: 26) |
| Peptide Up-1 (276-291) | YIGTTIVVRQVGRYLT (SEQ ID NO: 27) |
| Peptide 5-Ak (242-259) | AFVDGSKNGGDKHGANSL (SEQ ID NO: 30) |
| Peptide 6-Ak (300-316) | VVNAVEDWDSQGLYLC (SEQ ID NO: 28) |
| Peptide 7-Ak (217-234) | TIIFKNFQECVDQKVYQA (SEQ ID NO: 29) |

Peptide 1 has already been assayed in exemplary embodiment 2.

Figure 6A:
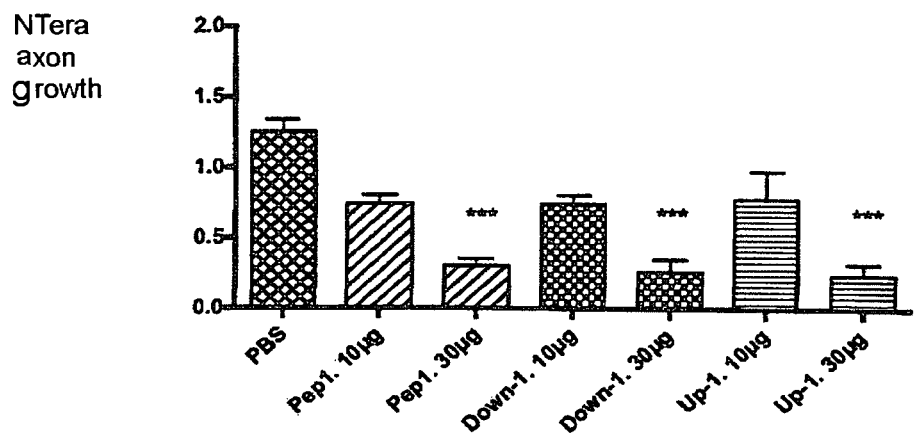
FIG. 6A shows the result of the analysis of RGM A peptide 1 and two peptides partly overlapping therewith (Down-1 and Up-1) in the Ntera nerve fiber growth assay. The peptides were added in a concentration of 10 µg/ml or 30 µg/ml to NTera aggregates. 24-36 hours later, the cultures were fixed, stained and analyzed. All 3 RGM A peptides were active in a concentration of 30 µg/ml and inhibited nerve fiber growth highly significantly.

The test results are depicted in FIGS. 6A and B.

Figure 6B:
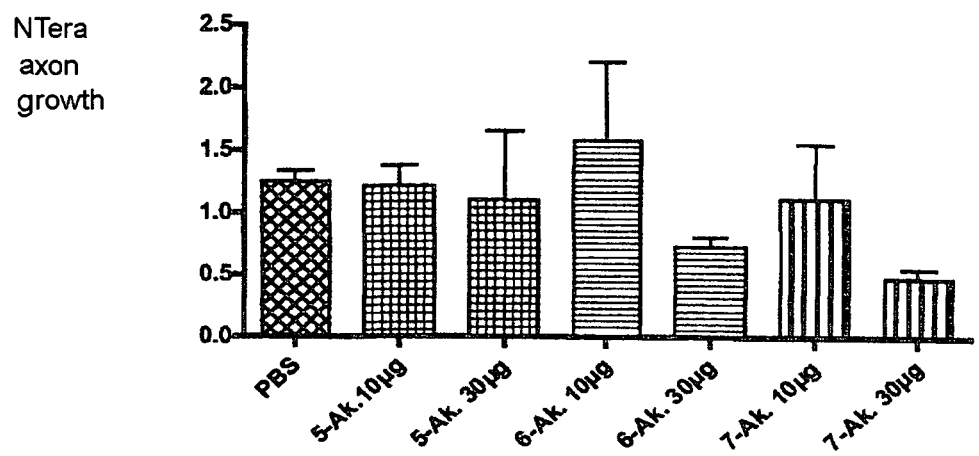
FIG. 6B shows the result of the analysis of three further RGM A peptides in the Ntera nerve fiber growth assay. The RGM A peptides were added in a concentration of 10 µg/ml or 30 µg/ml to NTera aggregates. 24-36 hours later, the cultures were fixed, stained and analyzed. All 3 RGM A peptides (5-Ak, 6-Ak, 7-Ak) were inactive in a concentration of 10 µg/ml; only peptides 7-Ak and 6-Ak showed at the higher concentrations a distinct trend in the direction of inhibition of nerve fiber growth.

Three of the assayed RGM A peptides led to a large reduction in nerve fiber growth in the NTera growth assay (FIG. 6A). These active RGM A peptides were the following peptides: peptide 1, peptide down-1 and peptide up-1. Inactive or only weakly active were the following peptides: peptide 5-Ak, peptide 6-Ak and peptide 7-Ak (FIG. 6B). This suggests that one of the inhibitory domains of RGM A is to be located in the region which is fixed by the 3 active RGM A peptides, i.e. the region of the human RGM A protein which extends approximately from 250 to 300, in particular from about 260-291, and thus includes the core region from position 267 to 285 (cf. SEQ ID NO: 7, 8). On the basis of the activity of the two peptides 6-Ak and 7-Ak, which showed a tendency to inhibit growth at the higher peptide concentration (FIG. 6B), it is perfectly conceivable that RGM A has further inhibitory domains and therefore the invention likewise relates to the domains in the region of about 210-260 and about 290-350.

Exemplary Embodiment 5

Neutralization of the Inhibitory Domain of RGM a with Antibodies

The intention in this experiment was to check whether polyclonal antibodies raised against active peptides of the inhibitory domain of RGM A are able to block the interaction of RGM A with its receptor neogenin and to neutralize in vitro the nerve fiber growth inhibition of the active and most potent RGM A fragment 2 (cf. exemplary embodiment 2).

Peptide down-1 was therefore used by way of example, because it forms part of the active RGM A fragment 2. Coupled to a carrier protein (LPH), this peptide was used to immunize two rabbits according to the following scheme

| Peptide | Amount of Peptide | Animal | First immunization | Boost | Boost | Boost | Bleeding | Titer |
|---------|-------------------|--------|--------------------|-------|-------|-------|----------|-------|
| Down-1 800790 | 2.4 mg | 8640 8641 | Day 0 | Day 7 | Day 14 | Day 28 | Day 35 | 1:150000 1:30000 |

| Last boost | Exsanguination | Purification |
|------------|----------------|--------------|
| Day 56 | 20 ml 20 ml | 24.9 mg in 22.5 ml 24.1 mg in 22 ml |

Figure 7A:
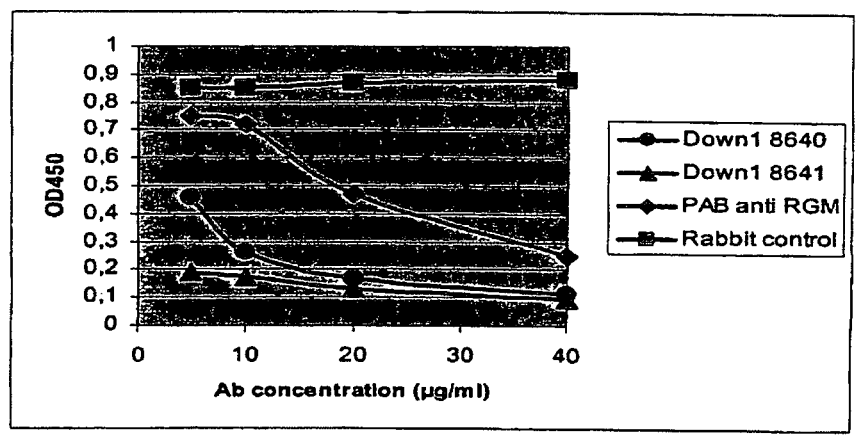
FIG. 7A shows the result of the RGM A—neogenin binding assay. In this assay, the polyclonal antibodies directed against the peptide Down-1 were very potent and blocked even at the lowest concentrations (Down 1 8641 & Down 1 8640) the interaction of the RGM A ligand with its receptor, the neogenin protein. A control antibody (rabbit control) had no effect, whereas a polyclonal antibody commercially available from R & D Systems (PAB anti RGM) likewise blocked the RGM A—neogenin interaction, although substantially less efficiently.

After several immunizations, the raised down-1-specific antibodies were purified and employed in various assay systems.

a) RGM A—neogenin binding assay:

The procedure took place as in assay method 3; the test results are depicted in FIG. 7A.

b) Neutralization of the active RGM A fragment in the axon growth assay:

The polyclonal antibodies raised against the peptide down-1 very efficiently blocked the interaction of the RGM A protein with its receptor neogenin. In the next assay, therefore, it was investigated whether the down-1-specific antibody is able to neutralize the very potent RGM A fragment 2 (cf. exemplary embodiment 3).

Figure 7B:
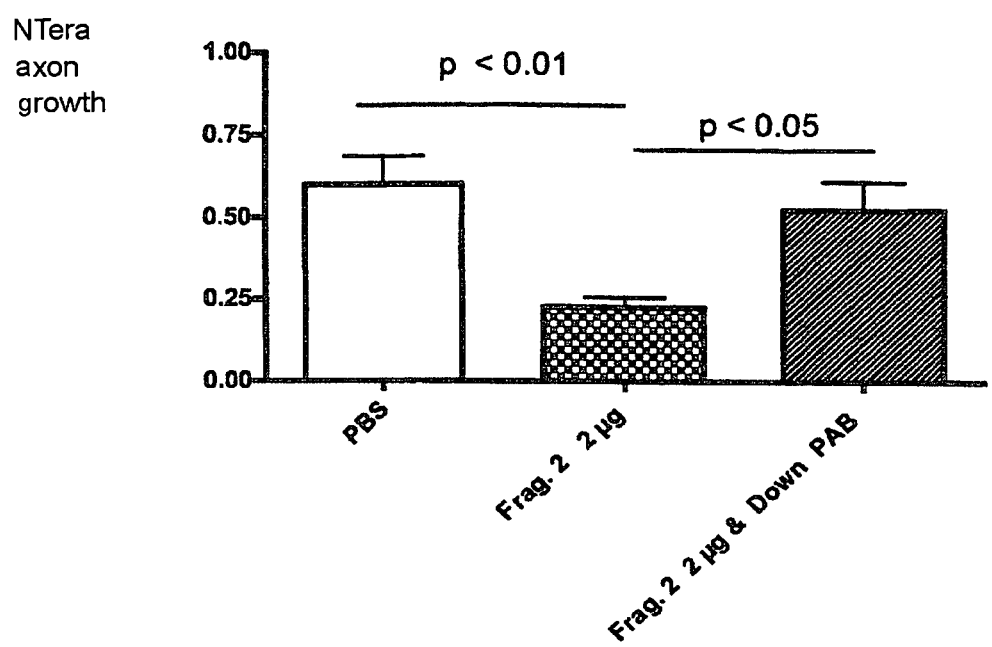
FIG. 7B shows how the Down-1 specific polyclonal antibody neutralizes the inhibitory activity of the potent RGM A fragment 2 in the Ntera nerve fiber growth assay. NTera cultures were treated in the outgrowth assay with PBS, fragment 2 (2 µg/ml) or with fragment 2 (2 µg/ml) and simultaneously with polyclonal antibody Down-1 (0.6 µg/ml).

The procedure took place as in assay method 2; the test results are depicted in FIG. 7B.

It is to be stated in summary that the polyclonal antibodies directed against the peptide down-1 prevent the interaction of neogenin and RGM A in the RGM A neogenin binding assay, and almost completely neutralize the inhibitory activity of the RGM A fragment in the axon growth assay. The region between the amino-terminal amino acids 250 and 300, especially 260 and 291, of the RGM A protein is therefore particularly important for its inhibitory activity and is hereby described as novel functionally relevant domain.

SEQUENCE LISTING

```
<160> NUMBER OF SEQ ID NOS: 34

<210> SEQ ID NO 1
<211> LENGTH: 1353
<212> TYPE: DNA
<213> ORGANISM: Homo sapiens
<220> FEATURE:
<221> NAME/KEY: CDS
<222> LOCATION: (1)..(1353)

<400> SEQUENCE: 1 atg cag ccg cca agg gag agg cta gtg gta aca ggc cga gct gga tgg        48
Met Gln Pro Pro Arg Glu Arg Leu Val Val Thr Gly Arg Ala Gly Trp
1               5                   10                  15 atg ggt atg ggg aga ggg gca gga cgt tca gcc ctg gga ttc tgg ccg        96
Met Gly Met Gly Arg Gly Ala Gly Arg Ser Ala Leu Gly Phe Trp Pro
            20                  25                  30 acc ctc gcc ttc ctc ctc tgc agc ttc ccc gca gcc acc tcc ccg tgc       144
Thr Leu Ala Phe Leu Leu Cys Ser Phe Pro Ala Ala Thr Ser Pro Cys
        35                  40                  45 aag atc ctc aag tgc aac tct gag ttc tgg agc gcc acg tcg ggc agc       192
Lys Ile Leu Lys Cys Asn Ser Glu Phe Trp Ser Ala Thr Ser Gly Ser
    50                  55                  60 cac gcc cca gcc tca gac gac acc ccc gag ttc tgt gca gcc ttg cgc       240
His Ala Pro Ala Ser Asp Asp Thr Pro Glu Phe Cys Ala Ala Leu Arg
65                  70                  75                  80 agc tac gcc ctg tgc acg cgg cgg acg gcc cgc acc tgc cgg ggt gac       288
Ser Tyr Ala Leu Cys Thr Arg Arg Thr Ala Arg Thr Cys Arg Gly Asp
                85                  90                  95 ctg gcc tac cac tcg gcc gtc cat ggc ata gag gac ctc atg agc cag       336
Leu Ala Tyr His Ser Ala Val His Gly Ile Glu Asp Leu Met Ser Gln
            100                 105                 110 cac aac tgc tcc aag gat ggc ccc acc tcg cag cca cgc ctg cgc acg       384
His Asn Cys Ser Lys Asp Gly Pro Thr Ser Gln Pro Arg Leu Arg Thr
        115                 120                 125 ctc cca ccg gcc gga gac agc cag gag cgc tcg gac agc ccc gag atc       432
Leu Pro Pro Ala Gly Asp Ser Gln Glu Arg Ser Asp Ser Pro Glu Ile
    130                 135                 140
```

-continued

| | | |
|---|---|---|
| tgc cat tac gag aag agc ttt cac aag cac tcg gcc acc ccc aac tac<br>Cys His Tyr Glu Lys Ser Phe His Lys His Ser Ala Thr Pro Asn Tyr<br>145                           150                    155                 160 | | 480 |
| acg cac tgt ggc ctc ttc ggg gac cca cac ctc agg act ttc acc gac<br>Thr His Cys Gly Leu Phe Gly Asp Pro His Leu Arg Thr Phe Thr Asp<br>                    165                   170                  175 | | 528 |
| cgc ttc cag acc tgc aag gtg cag ggc gcc tgg ccg ctc atc gac aat<br>Arg Phe Gln Thr Cys Lys Val Gln Gly Ala Trp Pro Leu Ile Asp Asn<br>               180                   185                  190 | | 576 |
| aat tac ctg aac gtg cag gcc acc aac acg cct gtg ctg ccc ggc tca<br>Asn Tyr Leu Asn Val Gln Ala Thr Asn Thr Pro Val Leu Pro Gly Ser<br>           195                   200                  205 | | 624 |
| gcg gcc act gcc acc agc aag ctc acc atc atc ttc aag aac ttc cag<br>Ala Ala Thr Ala Thr Ser Lys Leu Thr Ile Ile Phe Lys Asn Phe Gln<br>210                           215                    220 | | 672 |
| gag tgt gtg gac cag aag gtg tac cag gct gag atg gac gag ctc ccg<br>Glu Cys Val Asp Gln Lys Val Tyr Gln Ala Glu Met Asp Glu Leu Pro<br>225                           230                   235                  240 | | 720 |
| gcc gcc ttc gtg gat ggc tct aag aac ggt ggg gac aag cac ggg gcc<br>Ala Ala Phe Val Asp Gly Ser Lys Asn Gly Gly Asp Lys His Gly Ala<br>                        245                   250                  255 | | 768 |
| aac agc ctg aag atc act gag aag gtg tca ggc cag cac gtg gag atc<br>Asn Ser Leu Lys Ile Thr Glu Lys Val Ser Gly Gln His Val Glu Ile<br>             260                   265                  270 | | 816 |
| cag gcc aag tac atc ggc acc acc atc gtg gtg cgc cag gtg ggc cgc<br>Gln Ala Lys Tyr Ile Gly Thr Thr Ile Val Val Arg Gln Val Gly Arg<br>        275                   280                  285 | | 864 |
| tac ctg acc ttt gcc gtc cgc atg cca gag gaa gtg gtc aat gct gtg<br>Tyr Leu Thr Phe Ala Val Arg Met Pro Glu Glu Val Val Asn Ala Val<br>290                           295                   300 | | 912 |
| gag gac tgg gac agc cag ggt ctc tac ctc tgc ctg cgg ggc tgc ccc<br>Glu Asp Trp Asp Ser Gln Gly Leu Tyr Leu Cys Leu Arg Gly Cys Pro<br>305                           310                   315                  320 | | 960 |
| ctc aac cag cag atc gac ttc cag gcc ttc cac acc aat gct gag ggc<br>Leu Asn Gln Gln Ile Asp Phe Gln Ala Phe His Thr Asn Ala Glu Gly<br>                        325                   330                  335 | | 1008 |
| acc ggt gcc cgc agg ctg gca gcc gcc agc cct gca ccc aca gcc ccc<br>Thr Gly Ala Arg Arg Leu Ala Ala Ala Ser Pro Ala Pro Thr Ala Pro<br>             340                   345                  350 | | 1056 |
| gag acc ttc cca tac gag aca gcc gtg gcc aag tgc aag gag aag ctg<br>Glu Thr Phe Pro Tyr Glu Thr Ala Val Ala Lys Cys Lys Glu Lys Leu<br>        355                   360                  365 | | 1104 |
| ccg gtg gag gac ctg tac tac cag gcc tgc gtc ttc gac ctc ctc acc<br>Pro Val Glu Asp Leu Tyr Tyr Gln Ala Cys Val Phe Asp Leu Leu Thr<br>370                           375                   380 | | 1152 |
| acg ggc gac gtg aac ttc aca ctg gcc gcc tac tac gcg ttg gag gat<br>Thr Gly Asp Val Asn Phe Thr Leu Ala Ala Tyr Tyr Ala Leu Glu Asp<br>385                           390                   395                  400 | | 1200 |
| gtc aag atg ctc cac tcc aac aaa gac aaa ctg cac ctg tat gag agg<br>Val Lys Met Leu His Ser Asn Lys Asp Lys Leu His Leu Tyr Glu Arg<br>                        405                   410                  415 | | 1248 |
| act cgg gac ctg cca ggc agg gcg gct gcg ggg ctg ccc ctg gcc ccc<br>Thr Arg Asp Leu Pro Gly Arg Ala Ala Ala Gly Leu Pro Leu Ala Pro<br>             420                   425                  430 | | 1296 |
| cgg ccc ctc ctg ggc gcc ctc gtc ccg ctc ctg gcc ctg ctc cct gtg<br>Arg Pro Leu Leu Gly Ala Leu Val Pro Leu Leu Ala Leu Leu Pro Val<br>        435                   440                  445 | | 1344 |
| ttc tgc tag<br>Phe Cys<br>        450 | | 1353 |

```
<210> SEQ ID NO 2
<211> LENGTH: 450
<212> TYPE: PRT
<213> ORGANISM: Homo sapiens

<400> SEQUENCE: 2

Met Gln Pro Pro Arg Glu Arg Leu Val Val Thr Gly Arg Ala Gly Trp
 1               5                  10                  15

Met Gly Met Gly Arg Gly Ala Gly Arg Ser Ala Leu Gly Phe Trp Pro
            20                  25                  30

Thr Leu Ala Phe Leu Leu Cys Ser Phe Pro Ala Ala Thr Ser Pro Cys
        35                  40                  45

Lys Ile Leu Lys Cys Asn Ser Glu Phe Trp Ser Ala Thr Ser Gly Ser
 50                  55                  60

His Ala Pro Ala Ser Asp Asp Thr Pro Glu Phe Cys Ala Ala Leu Arg
 65                  70                  75                  80

Ser Tyr Ala Leu Cys Thr Arg Arg Thr Ala Arg Thr Cys Arg Gly Asp
                85                  90                  95

Leu Ala Tyr His Ser Ala Val His Gly Ile Glu Asp Leu Met Ser Gln
            100                 105                 110

His Asn Cys Ser Lys Asp Gly Pro Thr Ser Gln Pro Arg Leu Arg Thr
        115                 120                 125

Leu Pro Pro Ala Gly Asp Ser Gln Glu Arg Ser Asp Ser Pro Glu Ile
130                 135                 140

Cys His Tyr Glu Lys Ser Phe His Lys His Ser Ala Thr Pro Asn Tyr
145                 150                 155                 160

Thr His Cys Gly Leu Phe Gly Asp Pro His Leu Arg Thr Phe Thr Asp
                165                 170                 175

Arg Phe Gln Thr Cys Lys Val Gln Gly Ala Trp Pro Leu Ile Asp Asn
            180                 185                 190

Asn Tyr Leu Asn Val Gln Ala Thr Asn Thr Pro Val Leu Pro Gly Ser
        195                 200                 205

Ala Ala Thr Ala Thr Ser Lys Leu Thr Ile Ile Phe Lys Asn Phe Gln
210                 215                 220

Glu Cys Val Asp Gln Lys Val Tyr Gln Ala Glu Met Asp Glu Leu Pro
225                 230                 235                 240

Ala Ala Phe Val Asp Gly Ser Lys Asn Gly Gly Asp Lys His Gly Ala
                245                 250                 255

Asn Ser Leu Lys Ile Thr Glu Lys Val Ser Gly Gln His Val Glu Ile
            260                 265                 270

Gln Ala Lys Tyr Ile Gly Thr Thr Ile Val Val Arg Gln Val Gly Arg
        275                 280                 285

Tyr Leu Thr Phe Ala Val Arg Met Pro Glu Glu Val Val Asn Ala Val
290                 295                 300

Glu Asp Trp Asp Ser Gln Gly Leu Tyr Leu Cys Leu Arg Gly Cys Pro
305                 310                 315                 320

Leu Asn Gln Gln Ile Asp Phe Gln Ala Phe His Thr Asn Ala Glu Gly
                325                 330                 335

Thr Gly Ala Arg Arg Leu Ala Ala Ala Ser Pro Ala Pro Thr Ala Pro
            340                 345                 350

Glu Thr Phe Pro Tyr Glu Thr Ala Val Ala Lys Cys Lys Glu Lys Leu
        355                 360                 365

Pro Val Glu Asp Leu Tyr Tyr Gln Ala Cys Val Phe Asp Leu Leu Thr
370                 375                 380
```

-continued

```
Thr Gly Asp Val Asn Phe Thr Leu Ala Ala Tyr Tyr Ala Leu Glu Asp
385                 390                 395                 400

Val Lys Met Leu His Ser Asn Lys Asp Lys Leu His Leu Tyr Glu Arg
            405                 410                 415

Thr Arg Asp Leu Pro Gly Arg Ala Ala Ala Gly Leu Pro Leu Ala Pro
        420                 425                 430

Arg Pro Leu Leu Gly Ala Leu Val Pro Leu Leu Ala Leu Leu Pro Val
            435                 440                 445

Phe Cys
    450

<210> SEQ ID NO 3
<211> LENGTH: 1437
<212> TYPE: DNA
<213> ORGANISM: Homo sapiens
<220> FEATURE:
<221> NAME/KEY: CDS
<222> LOCATION: (1)..(1437)

<400> SEQUENCE: 3 atg ata agg aag aag agg aag cga agc gcg ccc ccc ggc cca tgc cgc      48
Met Ile Arg Lys Lys Arg Lys Arg Ser Ala Pro Pro Gly Pro Cys Arg
1               5                   10                  15 agc cac ggg ccc aga ccc gcc acg gcg ccc gcg ccg ccg ccc tcg ccg      96
Ser His Gly Pro Arg Pro Ala Thr Ala Pro Ala Pro Pro Pro Ser Pro
                20                  25                  30 gag ccc acg aga cct gca tgg acg ggc atg ggc ttg aga gca gca cct     144
Glu Pro Thr Arg Pro Ala Trp Thr Gly Met Gly Leu Arg Ala Ala Pro
            35                  40                  45 tcc agc gcc gcc gct gcc gcc gcc gag gtt gag cag cgc cgc cgc ccc     192
Ser Ser Ala Ala Ala Ala Ala Ala Glu Val Glu Gln Arg Arg Arg Pro
        50                  55                  60 ggg ctc tgc ccc ccg ccg ctg gag ctg ctg ctg ctg ctg ttc agc         240
Gly Leu Cys Pro Pro Pro Leu Glu Leu Leu Leu Leu Leu Leu Phe Ser
65                  70                  75                  80 ctc ggg ctg ctc cac gca ggt gac tgc caa cag cca gcc caa tgt cga     288
Leu Gly Leu Leu His Ala Gly Asp Cys Gln Gln Pro Ala Gln Cys Arg
                85                  90                  95 atc cag aaa tgc acc acg gac ttc gtg tcc ctg act tct cac ctg aac     336
Ile Gln Lys Cys Thr Thr Asp Phe Val Ser Leu Thr Ser His Leu Asn
                100                 105                 110 tct gcc gtt gac ggc ttt gac tct gag ttt tgc aag gcc ttg cgt gcc     384
Ser Ala Val Asp Gly Phe Asp Ser Glu Phe Cys Lys Ala Leu Arg Ala
            115                 120                 125 tat gct ggc tgc acc cag cga act tca aaa gcc tgc cgt ggc aac ctg     432
Tyr Ala Gly Cys Thr Gln Arg Thr Ser Lys Ala Cys Arg Gly Asn Leu
        130                 135                 140 gta tac cat tct gcc gtg ttg ggt atc agt gac ctc atg agc cag agg     480
Val Tyr His Ser Ala Val Leu Gly Ile Ser Asp Leu Met Ser Gln Arg
145                 150                 155                 160 aat tgt tcc aag gat gga ccc aca tcc tct acc aac ccc gaa gtg acc     528
Asn Cys Ser Lys Asp Gly Pro Thr Ser Ser Thr Asn Pro Glu Val Thr
                165                 170                 175 cat gat cct tgc aac tat cac agc cac gct gga gcc agg gaa cac agg     576
His Asp Pro Cys Asn Tyr His Ser His Ala Gly Ala Arg Glu His Arg
                180                 185                 190 aga ggg gac cag aac cct ccc agt tac ctt ttt tgt ggc ttg ttt gga     624
Arg Gly Asp Gln Asn Pro Pro Ser Tyr Leu Phe Cys Gly Leu Phe Gly
            195                 200                 205 gat cct cac ctc aga act ttc aag gat aac ttc caa aca tgc aaa gta     672
```

```
                Asp Pro His Leu Arg Thr Phe Lys Asp Asn Phe Gln Thr Cys Lys Val
                    210                 215                 220 gaa ggg gcc tgg cca ctc ata gat aat aat tat ctt tca gtt caa gtg        720
Glu Gly Ala Trp Pro Leu Ile Asp Asn Asn Tyr Leu Ser Val Gln Val
225                 230                 235                 240 aca aac gta cct gtg gtc cct gga tcc agt gct act gct aca aat aag        768
Thr Asn Val Pro Val Val Pro Gly Ser Ser Ala Thr Ala Thr Asn Lys
                245                 250                 255 atc act att atc ttc aaa gcc cac cat gag tgt aca gat cag aaa gtc        816
Ile Thr Ile Ile Phe Lys Ala His His Glu Cys Thr Asp Gln Lys Val
            260                 265                 270 tac caa gct gtg aca gat gac ctg ccg gcc gcc ttt gtg gat ggc acc        864
Tyr Gln Ala Val Thr Asp Asp Leu Pro Ala Ala Phe Val Asp Gly Thr
        275                 280                 285 acc agt ggt ggg gac agc gat gcc aag agc ctg cgt atc gtg gaa agg        912
Thr Ser Gly Gly Asp Ser Asp Ala Lys Ser Leu Arg Ile Val Glu Arg
    290                 295                 300 gag agt ggc cac tat gtg gag atg cac gcc cgc tat ata ggg acc aca        960
Glu Ser Gly His Tyr Val Glu Met His Ala Arg Tyr Ile Gly Thr Thr
305                 310                 315                 320 gtg ttt gtg cgg cag gtg ggt cgc tac ctg acc ctt gcc atc cgt atg       1008
Val Phe Val Arg Gln Val Gly Arg Tyr Leu Thr Leu Ala Ile Arg Met
                325                 330                 335 cct gaa gac ctg gcc atg tcc tac gag gag agc cag gac ctg cag ctg       1056
Pro Glu Asp Leu Ala Met Ser Tyr Glu Glu Ser Gln Asp Leu Gln Leu
                340                 345                 350 tgc gtg aac ggc tgc ccc ctg agt gaa cgc atc gat gac ggg cag ggc       1104
Cys Val Asn Gly Cys Pro Leu Ser Glu Arg Ile Asp Asp Gly Gln Gly
            355                 360                 365 cag gtg tct gcc atc ctg gga cac agc ctg cct cgc acc tcc ttg gtg       1152
Gln Val Ser Ala Ile Leu Gly His Ser Leu Pro Arg Thr Ser Leu Val
        370                 375                 380 cag gcc tgg cct ggc tac aca ctg gag act gcc aac act caa tgc cat       1200
Gln Ala Trp Pro Gly Tyr Thr Leu Glu Thr Ala Asn Thr Gln Cys His
    385                 390                 395                 400 gag aag atg cca gtg aag gac atc tat ttc cag tcc tgt gtc ttc gac       1248
Glu Lys Met Pro Val Lys Asp Ile Tyr Phe Gln Ser Cys Val Phe Asp
                405                 410                 415 ctg ctc acc act ggt gat gcc aac ttt act gcc gca gcc cac agt gcc       1296
Leu Leu Thr Thr Gly Asp Ala Asn Phe Thr Ala Ala Ala His Ser Ala
                420                 425                 430 ttg gag gat gtg gag gcc ctg cac cca agg aag gaa cgc tgg cac att       1344
Leu Glu Asp Val Glu Ala Leu His Pro Arg Lys Glu Arg Trp His Ile
            435                 440                 445 ttc ccc agc agt ggc aat ggg act ccc cgt gga ggc agt gat ttg tct       1392
Phe Pro Ser Ser Gly Asn Gly Thr Pro Arg Gly Gly Ser Asp Leu Ser
        450                 455                 460 gtc agt cta gga ctc acc tgc ttg atc ctt atc gtg ttt ttg tag          1437
Val Ser Leu Gly Leu Thr Cys Leu Ile Leu Ile Val Phe Leu
    465                 470                 475

<210> SEQ ID NO 4
<211> LENGTH: 478
<212> TYPE: PRT
<213> ORGANISM: Homo sapiens

<400> SEQUENCE: 4

Met Ile Arg Lys Lys Arg Lys Ser Ala Pro Pro Gly Pro Cys Arg
1               5                   10                  15

Ser His Gly Pro Arg Pro Ala Thr Ala Pro Ala Pro Pro Ser Pro
```

-continued

```
            20                  25                  30
Glu Pro Thr Arg Pro Ala Trp Thr Gly Met Gly Leu Arg Ala Ala Pro
                35                  40                  45
Ser Ser Ala Ala Ala Ala Ala Glu Val Glu Gln Arg Arg Arg Pro
    50                  55                  60
Gly Leu Cys Pro Pro Leu Glu Leu Leu Leu Leu Leu Leu Phe Ser
65                  70                  75                  80
Leu Gly Leu Leu His Ala Gly Asp Cys Gln Gln Pro Ala Gln Cys Arg
                85                  90                  95
Ile Gln Lys Cys Thr Thr Asp Phe Val Ser Leu Thr Ser His Leu Asn
                100                 105                 110
Ser Ala Val Asp Gly Phe Asp Ser Glu Phe Cys Lys Ala Leu Arg Ala
            115                 120                 125
Tyr Ala Gly Cys Thr Gln Arg Thr Ser Lys Ala Cys Arg Gly Asn Leu
            130                 135                 140
Val Tyr His Ser Ala Val Leu Gly Ile Ser Asp Leu Met Ser Gln Arg
145                 150                 155                 160
Asn Cys Ser Lys Asp Gly Pro Thr Ser Thr Asn Pro Glu Val Thr
                165                 170                 175
His Asp Pro Cys Asn Tyr His Ser His Ala Gly Ala Arg Glu His Arg
            180                 185                 190
Arg Gly Asp Gln Asn Pro Pro Ser Tyr Leu Phe Cys Gly Leu Phe Gly
            195                 200                 205
Asp Pro His Leu Arg Thr Phe Lys Asp Asn Phe Gln Thr Cys Lys Val
            210                 215                 220
Glu Gly Ala Trp Pro Leu Ile Asp Asn Asn Tyr Leu Ser Val Gln Val
225                 230                 235                 240
Thr Asn Val Pro Val Pro Gly Ser Ser Ala Thr Ala Thr Asn Lys
                245                 250                 255
Ile Thr Ile Ile Phe Lys Ala His His Glu Cys Thr Asp Gln Lys Val
            260                 265                 270
Tyr Gln Ala Val Thr Asp Asp Leu Pro Ala Ala Phe Val Asp Gly Thr
            275                 280                 285
Thr Ser Gly Gly Asp Ser Asp Ala Lys Ser Leu Arg Ile Val Glu Arg
290                 295                 300
Glu Ser Gly His Tyr Val Glu Met His Ala Arg Tyr Ile Gly Thr Thr
305                 310                 315                 320
Val Phe Val Arg Gln Val Gly Arg Tyr Leu Thr Leu Ala Ile Arg Met
            325                 330                 335
Pro Glu Asp Leu Ala Met Ser Tyr Glu Glu Ser Gln Asp Leu Gln Leu
            340                 345                 350
Cys Val Asn Gly Cys Pro Leu Ser Glu Arg Ile Asp Asp Gly Gln Gly
            355                 360                 365
Gln Val Ser Ala Ile Leu Gly His Ser Leu Pro Arg Thr Ser Leu Val
            370                 375                 380
Gln Ala Trp Pro Gly Tyr Thr Leu Glu Thr Ala Asn Thr Gln Cys His
385                 390                 395                 400
Glu Lys Met Pro Val Lys Asp Ile Tyr Phe Gln Ser Cys Val Phe Asp
                405                 410                 415
Leu Leu Thr Thr Gly Asp Ala Asn Phe Thr Ala Ala His Ser Ala
                420                 425                 430
Leu Glu Asp Val Glu Ala Leu His Pro Arg Lys Glu Arg Trp His Ile
            435                 440                 445
```

```
Phe Pro Ser Ser Gly Asn Gly Thr Pro Arg Gly Gly Ser Asp Leu Ser
    450                 455                 460

Val Ser Leu Gly Leu Thr Cys Leu Ile Leu Ile Val Phe Leu
465                 470                 475

<210> SEQ ID NO 5
<211> LENGTH: 1281
<212> TYPE: DNA
<213> ORGANISM: Homo sapiens
<220> FEATURE:
<221> NAME/KEY: CDS
<222> LOCATION: (1)..(1281)

<400> SEQUENCE: 5 atg ggg gag cca ggc cag tcc cct agt ccc agg tcc tcc cat ggc agt      48
Met Gly Glu Pro Gly Gln Ser Pro Ser Pro Arg Ser Ser His Gly Ser
1               5                   10                  15 ccc cca act cta agc act ctc act ctc ctg ctc ctc tgt gga cat          96
Pro Pro Thr Leu Ser Thr Leu Thr Leu Leu Leu Leu Leu Cys Gly His
                20                  25                  30 gct cat tct caa tgc aag atc ctc cgc tgc aat gct gag tac gta tcg    144
Ala His Ser Gln Cys Lys Ile Leu Arg Cys Asn Ala Glu Tyr Val Ser
            35                  40                  45 tcc act ctg agc ctt aga ggt ggg ggt tca tca gga gca ctt cga gga    192
Ser Thr Leu Ser Leu Arg Gly Gly Gly Ser Ser Gly Ala Leu Arg Gly
        50                  55                  60 gga gga gga gga ggc cgg ggt gga ggg gtg ggc tct ggc ggc ctc tgt    240
Gly Gly Gly Gly Gly Arg Gly Gly Val Gly Ser Gly Gly Leu Cys
65                  70                  75                  80 cga gcc ctc cgc tcc tat gcg ctc tgc act cgg cga acc gcc cgc acc    288
Arg Ala Leu Arg Ser Tyr Ala Leu Cys Thr Arg Arg Thr Ala Arg Thr
                85                  90                  95 tgc cgc ggg gac ctc gcc ttc cat tcg gcg gta cat ggc atc gaa gac    336
Cys Arg Gly Asp Leu Ala Phe His Ser Ala Val His Gly Ile Glu Asp
            100                 105                 110 ctg atg atc cag cac aac tgc tcc cgc cag ggc cct aca gcc cct ccc    384
Leu Met Ile Gln His Asn Cys Ser Arg Gln Gly Pro Thr Ala Pro Pro
        115                 120                 125 ccg ccc cgg ggc ccc gcc ctt cca ggc gcg ggc tcc ggc ctc cct gcc    432
Pro Pro Arg Gly Pro Ala Leu Pro Gly Ala Gly Ser Gly Leu Pro Ala
    130                 135                 140 ccg gac cct tgt gac tat gaa ggc cgg ttt tcc cgg ctg cat ggt cgt    480
Pro Asp Pro Cys Asp Tyr Glu Gly Arg Phe Ser Arg Leu His Gly Arg
145                 150                 155                 160 ccc ccg ggg ttc ttg cat tgc gct tcc ttc ggg gac ccc cat gtg cgc    528
Pro Pro Gly Phe Leu His Cys Ala Ser Phe Gly Asp Pro His Val Arg
                165                 170                 175 agc ttc cac cat cac ttt cac aca tgc cgt gtc caa gga gct tgg cct    576
Ser Phe His His His Phe His Thr Cys Arg Val Gln Gly Ala Trp Pro
            180                 185                 190 cta ctg gat aat gac ttc ctc ttt gtc caa gcc acc agc tcc ccc atg    624
Leu Leu Asp Asn Asp Phe Leu Phe Val Gln Ala Thr Ser Ser Pro Met
        195                 200                 205 gcg ttg ggg gcc aac gct acc gcc acc cgg aag ctc acc atc ata ttt    672
Ala Leu Gly Ala Asn Ala Thr Ala Thr Arg Lys Leu Thr Ile Ile Phe
    210                 215                 220 aag aac atg cag gaa tgc att gat cag aag gtg tat cag gct gag gtg    720
Lys Asn Met Gln Glu Cys Ile Asp Gln Lys Val Tyr Gln Ala Glu Val
225                 230                 235                 240 gat aat ctt cct gta gcc ttt gaa gat ggt tct atc aat gga ggt gac    768
Asp Asn Leu Pro Val Ala Phe Glu Asp Gly Ser Ile Asn Gly Gly Asp
```

```
                        Asp Asn Leu Pro Val Ala Phe Glu Asp Gly Ser Ile Asn Gly Gly Asp
                                        245                 250                 255 cga cct ggg gga tcc agt ttg tcg att caa act gct aac cct ggg aac             816
Arg Pro Gly Gly Ser Ser Leu Ser Ile Gln Thr Ala Asn Pro Gly Asn
                260                 265                 270 cat gtg gag atc caa gct gcc tac att ggc aca act ata atc att cgg             864
His Val Glu Ile Gln Ala Ala Tyr Ile Gly Thr Thr Ile Ile Ile Arg
            275                 280                 285 cag aca gct ggg cag ctc tcc ttc tcc atc aag gta gca gag gat gtg             912
Gln Thr Ala Gly Gln Leu Ser Phe Ser Ile Lys Val Ala Glu Asp Val
        290                 295                 300 gcc atg gcc ttc tca gct gaa cag gac ctg cag ctc tgt gtt ggg ggg             960
Ala Met Ala Phe Ser Ala Glu Gln Asp Leu Gln Leu Cys Val Gly Gly
305                 310                 315                 320 tgc cct cca agt cag cga ctc tct cga tca gag cgc aat cgt cgg gga            1008
Cys Pro Pro Ser Gln Arg Leu Ser Arg Ser Glu Arg Asn Arg Arg Gly
                325                 330                 335 gct ata acc att gat act gcc aga cgg ctg tgc aag gaa ggg ctt cca            1056
Ala Ile Thr Ile Asp Thr Ala Arg Arg Leu Cys Lys Glu Gly Leu Pro
            340                 345                 350 gtg gaa gat gct tac ttc cat tcc tgt gtc ttt gat gtt tta att tct            1104
Val Glu Asp Ala Tyr Phe His Ser Cys Val Phe Asp Val Leu Ile Ser
        355                 360                 365 ggt gat ccc aac ttt acc gtg gca gct cag gca gca ctg gag gat gcc            1152
Gly Asp Pro Asn Phe Thr Val Ala Ala Gln Ala Ala Leu Glu Asp Ala
370                 375                 380 cga gcc ttc ctg cca gac tta gag aag ctg cat ctc ttc ccc tca gat            1200
Arg Ala Phe Leu Pro Asp Leu Glu Lys Leu His Leu Phe Pro Ser Asp
385                 390                 395                 400 gct ggg gtt cct ctt tcc tca gca acc ctc tta gct cca ctc ctt tct            1248
Ala Gly Val Pro Leu Ser Ser Ala Thr Leu Leu Ala Pro Leu Leu Ser
                405                 410                 415 ggg ctc ttt gtt ctg tgg ctt tgc att cag taa                                1281
Gly Leu Phe Val Leu Trp Leu Cys Ile Gln
            420                 425

<210> SEQ ID NO 6
<211> LENGTH: 426
<212> TYPE: PRT
<213> ORGANISM: Homo sapiens

<400> SEQUENCE: 6

Met Gly Glu Pro Gly Gln Ser Pro Ser Pro Arg Ser Ser His Gly Ser
1               5                   10                  15

Pro Pro Thr Leu Ser Thr Leu Thr Leu Leu Leu Leu Cys Gly His
                20                  25                  30

Ala His Ser Gln Cys Lys Ile Leu Arg Cys Asn Ala Glu Tyr Val Ser
            35                  40                  45

Ser Thr Leu Ser Leu Arg Gly Gly Ser Ser Gly Ala Leu Arg Gly
        50                  55                  60

Gly Gly Gly Gly Arg Gly Gly Val Ser Gly Gly Leu Cys
65                  70                  75                  80

Arg Ala Leu Arg Ser Tyr Ala Leu Cys Thr Arg Thr Ala Arg Thr
                85                  90                  95

Cys Arg Gly Asp Leu Ala Phe His Ser Ala Val His Gly Ile Glu Asp
                100                 105                 110

Leu Met Ile Gln His Asn Cys Ser Arg Gln Gly Pro Thr Ala Pro Pro
            115                 120                 125
```

Pro Pro Arg Gly Pro Ala Leu Pro Gly Ala Gly Ser Gly Leu Pro Ala
        130                 135                 140

Pro Asp Pro Cys Asp Tyr Glu Gly Arg Phe Ser Arg Leu His Gly Arg
145                 150                 155                 160

Pro Pro Gly Phe Leu His Cys Ala Ser Phe Gly Asp Pro His Val Arg
                165                 170                 175

Ser Phe His His His Phe His Thr Cys Arg Val Gln Gly Ala Trp Pro
            180                 185                 190

Leu Leu Asp Asn Asp Phe Leu Phe Val Gln Ala Thr Ser Ser Pro Met
        195                 200                 205

Ala Leu Gly Ala Asn Ala Thr Ala Thr Arg Lys Leu Thr Ile Ile Phe
210                 215                 220

Lys Asn Met Gln Glu Cys Ile Asp Gln Lys Val Tyr Gln Ala Glu Val
225                 230                 235                 240

Asp Asn Leu Pro Val Ala Phe Glu Asp Gly Ser Ile Asn Gly Gly Asp
                245                 250                 255

Arg Pro Gly Gly Ser Ser Leu Ser Ile Gln Thr Ala Asn Pro Gly Asn
            260                 265                 270

His Val Glu Ile Gln Ala Tyr Ile Gly Thr Thr Ile Ile Ile Arg
        275                 280                 285

Gln Thr Ala Gly Gln Leu Ser Phe Ser Ile Lys Val Ala Glu Asp Val
290                 295                 300

Ala Met Ala Phe Ser Ala Glu Gln Asp Leu Gln Leu Cys Val Gly Gly
305                 310                 315                 320

Cys Pro Pro Ser Gln Arg Leu Ser Arg Ser Glu Arg Asn Arg Arg Gly
                325                 330                 335

Ala Ile Thr Ile Asp Thr Ala Arg Arg Leu Cys Lys Glu Gly Leu Pro
            340                 345                 350

Val Glu Asp Ala Tyr Phe His Ser Cys Val Phe Asp Val Leu Ile Ser
        355                 360                 365

Gly Asp Pro Asn Phe Thr Val Ala Ala Gln Ala Ala Leu Glu Asp Ala
370                 375                 380

Arg Ala Phe Leu Pro Asp Leu Glu Lys Leu His Leu Phe Pro Ser Asp
385                 390                 395                 400

Ala Gly Val Pro Leu Ser Ser Ala Thr Leu Leu Ala Pro Leu Leu Ser
                405                 410                 415

Gly Leu Phe Val Leu Trp Leu Cys Ile Gln
            420                 425

<210> SEQ ID NO 7
<211> LENGTH: 19
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (2)..(3)
<223> OTHER INFORMATION: Any amino acid
<220> FEATURE:
<221> NAME/KEY: MOD_RES
<222> LOCATION: (6)..(7)
<223> OTHER INFORMATION: Any amino acid
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES -continued
<222> LOCATION: (15)..(17)
<223> OTHER INFORMATION: Any amino acid

<400> SEQUENCE: 7

Gly Xaa Xaa Val Glu Xaa Xaa Ala Xaa Tyr Ile Gly Thr Thr Xaa Xaa
1               5                   10                  15

Xaa Arg Gln

<210> SEQ ID NO 8
<211> LENGTH: 19
<212> TYPE: PRT
<213> ORGANISM: Artificial Sequence
<220> FEATURE:
<223> OTHER INFORMATION: Description of Artificial Sequence: Synthetic
      binding domain peptide

<400> SEQUENCE: 8

Gly Gln His Val Glu Ile Gln Ala Lys Tyr Ile Gly Thr Thr Ile Val
1               5                   10                  15

Val Arg Gln

<210> SEQ ID NO 9
<211> LENGTH: 19
<212> TYPE: PRT
<213> ORGANISM: Artificial Sequence
<220> FEATURE:
<223> OTHER INFORMATION: Description of Artificial Sequence: Synthetic
      binding domain peptide

<400> SEQUENCE: 9

Gly His Tyr Val Glu Met His Ala Arg Tyr Ile Gly Thr Thr Val Phe
1               5                   10                  15

Val Arg Gln

<210> SEQ ID NO 10
<211> LENGTH: 19
<212> TYPE: PRT
<213> ORGANISM: Artificial Sequence
<220> FEATURE:
<223> OTHER INFORMATION: Description of Artificial Sequence: Synthetic
      binding domain peptide

<400> SEQUENCE: 10

Gly Asn His Val Glu Ile Gln Ala Ala Tyr Ile Gly Thr Thr Ile Ile
1               5                   10                  15

Ile Arg Gln

<210> SEQ ID NO 11
<211> LENGTH: 79
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ggggacaagt tgtacaaaa aagcaggctt tctggaagtt ctgttccagg ggcccccaca      60
cctcaggact tcaccgac                                                   79

<210> SEQ ID NO 12
<211> LENGTH: 55
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 12
ggggaccact ttgtacaaga aagctgggtg ctcgtccatc tcagcctggt acacc      55

<210> SEQ ID NO 13
<211> LENGTH: 83
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ggggacaagt ttgtacaaaa aagcaggctt tctggaagtt ctgttccagg ggcccatcat    60
cttcaagaac ttccaggagt gtg                                            83

<210> SEQ ID NO 14
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ggggaccact ttgtacaaga aagctgggtg gcgcaccacg atggtggtg              49

<210> SEQ ID NO 15
<211> LENGTH: 77
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ggggacaagt ttgtacaaaa aagcaggctt tctggaagtt ctgttccagg ggccctcagg    60
ccagcacgtg gagatcc                                                   77

<210> SEQ ID NO 16
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ggggaccact ttgtacaaga aagctgggtc ctcagcattg gtgtggaagg cc           52

<210> SEQ ID NO 17
<211> LENGTH: 73
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ggggacaagt ttgtacaaaa aagcaggctt tctggaagtt ctgttccagg ggcccctgcg    60
gggctgcccc ctc                                                       73

```
<210> SEQ ID NO 18
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ggggaccact ttgtacaaga aagctgggtc gcccgtggtg aggaggtcg                49

<210> SEQ ID NO 19
<211> LENGTH: 76
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ggggacaagt ttgtacaaaa aagcaggctt tctggaagtt ctgttccagg ggcccctgcc    60
ggtggaggac ctgtac                                                    76

<210> SEQ ID NO 20
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ggggaccact ttgtacaaga aagctgggtt gcctggcagg tcccgagtc                49

<210> SEQ ID NO 21
<211> LENGTH: 79
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ggggacaagt ttgtacaaaa aagcaggctt tctggaagtt ctgttccagg ggcccccaca    60
cctcaggact ttcaccgac                                                 79

<210> SEQ ID NO 22
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ggggaccact ttgtacaaga aagctgggtt gcctggcagg tcccgagtc                49

<210> SEQ ID NO 23
<211> LENGTH: 32
<212> TYPE: PRT
<213> ORGANISM: Artificial Sequence
<220> FEATURE:
<223> OTHER INFORMATION: Description of Artificial Sequence: Synthetic
      binding domain peptide

<400> SEQUENCE: 23
```

```
Lys Ile Thr Glu Lys Val Ser Gly Gln His Val Glu Ile Gln Ala Lys
1               5                   10                  15

Tyr Ile Gly Thr Thr Ile Val Val Arg Gln Val Gly Arg Tyr Leu Thr
            20                  25                  30
```

<210> SEQ ID NO 24
<211> LENGTH: 32
<212> TYPE: PRT
<213> ORGANISM: Artificial Sequence
<220> FEATURE:
<223> OTHER INFORMATION: Description of Artificial Sequence: Synthetic
      binding domain peptide

<400> SEQUENCE: 24

```
Arg Ile Val Glu Arg Glu Ser Gly His Tyr Val Glu Met His Ala Arg
1               5                   10                  15

Tyr Ile Gly Thr Thr Val Phe Val Arg Gln Val Gly Arg Tyr Leu Thr
            20                  25                  30
```

<210> SEQ ID NO 25
<211> LENGTH: 32
<212> TYPE: PRT
<213> ORGANISM: Artificial Sequence
<220> FEATURE:
<223> OTHER INFORMATION: Description of Artificial Sequence: Synthetic
      binding domain peptide

<400> SEQUENCE: 25

```
Ser Ile Gln Thr Ala Asn Pro Gly Asn His Val Glu Ile Gln Ala Ala
1               5                   10                  15

Tyr Ile Gly Thr Thr Ile Ile Ile Arg Gln Thr Ala Gly Gln Leu Ser
            20                  25                  30
```

<210> SEQ ID NO 26
<211> LENGTH: 16
<212> TYPE: PRT
<213> ORGANISM: Artificial Sequence
<220> FEATURE:
<223> OTHER INFORMATION: Description of Artificial Sequence: Synthetic
      binding domain peptide

<400> SEQUENCE: 26

```
Lys Ile Thr Glu Lys Val Ser Gly Gln His Val Glu Ile Gln Ala Lys
1               5                   10                  15
```

<210> SEQ ID NO 27
<211> LENGTH: 16
<212> TYPE: PRT
<213> ORGANISM: Artificial Sequence
<220> FEATURE:
<223> OTHER INFORMATION: Description of Artificial Sequence: Synthetic
      binding domain peptide

<400> SEQUENCE: 27

```
Tyr Ile Gly Thr Thr Ile Val Val Arg Gln Val Gly Arg Tyr Leu Thr
1               5                   10                  15
```

<210> SEQ ID NO 28
<211> LENGTH: 16
<212> TYPE: PRT
<213> ORGANISM: Artificial Sequence
<220> FEATURE:
<223> OTHER INFORMATION: Description of Artificial Sequence: Synthetic
      binding domain peptide

```
<400> SEQUENCE: 28

Val Val Asn Ala Val Glu Asp Trp Asp Ser Gln Gly Leu Tyr Leu Cys
1               5                   10                  15

<210> SEQ ID NO 29
<211> LENGTH: 18
<212> TYPE: PRT
<213> ORGANISM: Artificial Sequence
<220> FEATURE:
<223> OTHER INFORMATION: Description of Artificial Sequence: Synthetic
      binding domain peptide

<400> SEQUENCE: 29

Thr Ile Ile Phe Lys Asn Phe Gln Glu Cys Val Asp Gln Lys Val Tyr
1               5                   10                  15

Gln Ala

<210> SEQ ID NO 30
<211> LENGTH: 18
<212> TYPE: PRT
<213> ORGANISM: Artificial Sequence
<220> FEATURE:
<223> OTHER INFORMATION: Description of Artificial Sequence: Synthetic
      binding domain peptide

<400> SEQUENCE: 30

Ala Phe Val Asp Gly Ser Lys Asn Gly Gly Asp Lys His Gly Ala Asn
1               5                   10                  15

Ser Leu

<210> SEQ ID NO 31
<211> LENGTH: 16
<212> TYPE: PRT
<213> ORGANISM: Artificial Sequence
<220> FEATURE:
<223> OTHER INFORMATION: Description of Artificial Sequence: Synthetic
      binding domain peptide

<400> SEQUENCE: 31

Arg Ile Val Glu Arg Glu Ser Gly His Tyr Val Glu Met His Ala Arg
1               5                   10                  15

<210> SEQ ID NO 32
<211> LENGTH: 16
<212> TYPE: PRT
<213> ORGANISM: Artificial sequence
<220> FEATURE:
<223> OTHER INFORMATION: Description of Artificial Sequence: Synthetic
      binding domain peptide

<400> SEQUENCE: 32

Tyr Ile Gly Thr Thr Val Phe Val Arg Gln Val Gly Arg Tyr Leu Thr
1               5                   10                  15

<210> SEQ ID NO 33
<211> LENGTH: 16
<212> TYPE: PRT
<213> ORGANISM: Artificial Sequence
<220> FEATURE:
<223> OTHER INFORMATION: Description of Artificial Sequence: Synthetic
      binding domain peptide

<400> SEQUENCE: 33

Ser Ile Gln Thr Ala Asn Pro Gly Asn His Val Glu Ile Gln Ala Ala
1               5                   10                  15
```

```
<210> SEQ ID NO 34
<211> LENGTH: 16
<212> TYPE: PRT
<213> ORGANISM: Artificial Sequence
<220> FE